United States Patent
Smith

(10) Patent No.: US 12,247,984 B2
(45) Date of Patent: Mar. 11, 2025

(54) GENERATION OF HUMAN ALLERGEN- AND HELMINTH-SPECIFIC IGE MONOCLONAL ANTIBODIES FOR DIAGNOSTIC AND THERAPEUTIC USE

(71) Applicant: Vanderbilt University, Nashville, TN (US)

(72) Inventor: Scott A. Smith, White Bluff, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 989 days.

(21) Appl. No.: 17/127,953

(22) Filed: Dec. 18, 2020

(65) Prior Publication Data

US 2021/0382064 A1 Dec. 9, 2021

Related U.S. Application Data

(63) Continuation of application No. 16/481,165, filed as application No. PCT/US2018/015870 on Jan. 30, 2018, now Pat. No. 10,908,168.

(60) Provisional application No. 62/452,603, filed on Jan. 31, 2017.

(51) Int. Cl.
| | |
|---|---|
| *A61K 39/395* | (2006.01) |
| *A61K 39/35* | (2006.01) |
| *A61K 45/06* | (2006.01) |
| *C07K 16/16* | (2006.01) |
| *C07K 16/18* | (2006.01) |
| *G01N 33/53* | (2006.01) |
| *G01N 33/68* | (2006.01) |

(52) U.S. Cl.
CPC ......... *G01N 33/686* (2013.01); *A61K 39/35* (2013.01); *A61K 45/06* (2013.01); *C07K 16/16* (2013.01); *C07K 16/18* (2013.01); *G01N 33/5308* (2013.01); *C07K 2317/21* (2013.01); *G01N 2333/43526* (2013.01); *G01N 2333/43582* (2013.01)

(58) Field of Classification Search
None
See application file for complete search history.

(56) References Cited

U.S. PATENT DOCUMENTS

| | | |
|---|---|---|
| 8,697,079 B2 | 4/2014 | Penichet et al. |
| 8,802,375 B2 | 8/2014 | Sampson et al. |
| 9,127,251 B2 | 9/2015 | Spits et al. |
| 9,238,062 B2 | 1/2016 | Chen et al. |
| 2013/0243750 A1 | 9/2013 | Scheerens et al. |
| 2014/0275492 A1 | 9/2014 | Sutkowski |
| 2014/0315252 A1 | 10/2014 | Endl et al. |
| 2016/0157468 A1 | 6/2016 | Cogne et al. |

FOREIGN PATENT DOCUMENTS

| | | |
|---|---|---|
| WO | WO 2012/072678 | 6/2012 |
| WO | WO 2016/149137 | 9/2016 |

OTHER PUBLICATIONS

Rudikoff et al. (1982). PNAS. 79:1979-1983.*
Achatz, Gernot, Lars Nitschke, and Marinus C. Lamers. "Effect of transmembrane and cytoplasmic domains of IgE on the IgE response." *Science* 276.5311 (1997): 409-411.
Avery, Danielle T., et al. "STAT3 is required for IL-21-induced secretion of IgE from human naive B cells." *Blood* 112.5 (2008): 1784-1793.
Fitzsimmons, Colin Matthew, Franco Harald Falcone, and David W. Dunne. "Helminth allergens, parasite-specific IgE, and its protective role in human immunity." *Frontiers in immunology* 5 (2014): 61.
International Preliminary Report on Patentability issued in International Application No. PCT/US2018/015870, mailed Aug. 15, 2019.
International Search Report and Written Opinion issued in International Application No. PCT/US2018/015870, mailed Jun. 20, 2018.
Invitation to pay additional fees issued in International Application No. PCT/US2018/015870, mailed Apr. 10, 2018.
Karnowski, Alexander, et al. "Inefficient processing of mRNA for the membraneform of IgE is a genetic mechanism to limit recruitment of IgE-secreting cells." *European journal of immunology* 36.7 (2006): 1917-1925.
Pomés et al., "First Naturally Occurring Human IgE Antibody Against Mite Allergen Der p 2", Abstract from AAAAI Annual Meeting, Mar. 2017.
Pomés et al., "Human IgE monoclonal antibodies with natural heavy and light chain pairing and specificity for asthma-associated allergens", Abstract from EAACI Annual Meeting, Jun. 2017.
Renz, H. A. R. A. L. D., Bruce D. Mazer, and Erwin W. Gelfand. "Differential inhibition of T and B cell function in IL-4-dependent IgE production by cyclosporin A and methylprednisolone." *The Journal of Immunology* 145.11 (1990): 3641-3646.
Shade Kai-Ting C, et al. "Sialylation of Immunoglobulin E Is a Determinant of Allergic Pathogenicity" *Nature* 582(2020):265-270.
Smith, "Antigenic Landscape of the Human Helminth IgE Antibody Response", NIH report for Project No. 5R01AI130459-04, dated 2020.
Smith, "Generation and Characterization of Full-Length Naturally Occurring Allergen-Specific Human IgE MABs", NIH report for Project No. 1R21AI123307-01A1, dated 2017.
Zone, John J., et al. "IgE basement membrane zone antibodies induce eosinophil infiltration and histological blisters in engrafted human skin on SCID mice." *Journal of Investigative Dermatology* 127.5 (2007): 1167-1174.
Chen, Kuan-Wei, et al. "Reduction of the in vivo allergenicity of Der p 2, the major house-dust mite allergen, by genetic engineering." *Molecular immunology* 45.9 (2008): 2486-2498.

(Continued)

*Primary Examiner* — Christine J Saoud
*Assistant Examiner* — Jon M Lockard
(74) *Attorney, Agent, or Firm* — Parker Highlander PLLC

(57) ABSTRACT

The present disclosure is directed to human monoclonal IgE antibodies, and IgG antibodies engineered therefrom. Such engineered antibodies can be used to blunt pathologic IgE responses in subjects, such as in the treatment or prevention of allergies.

Figure 1:
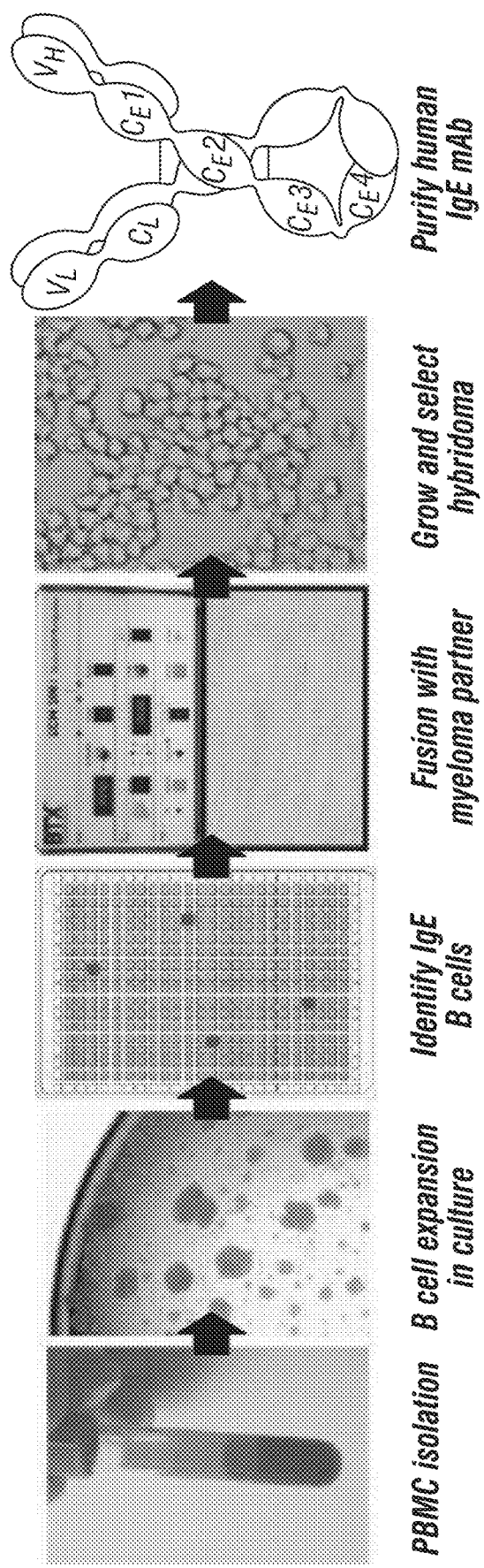

11 Claims, 7 Drawing Sheets
Specification includes a Sequence Listing.

(56) References Cited

OTHER PUBLICATIONS

Extended European Search Report issued in European Application No. 18748576.8, mailed Nov. 5, 2020.
Braren, Ingke, et al. "Generation of human monoclonal allergen-specific IgE and IgG antibodies from synthetic antibody libraries." *Clinical chemistry* 53.5 (2007): 837-844.
De Pascalis, Roberto, et al. "Grafting of "abbreviated" complementarity-determining regions containing specificity-determining residues essential for ligand contact to engineer a less immunogenic humanized monoclonal antibody." *the Journal of Immunology* 169.6 (2002): 3076-3084.
Goel, Manisha, et al. "Plasticity within the antigen-combining site may manifest as molecular mimicry in the humoral immune response." *The Journal of Immunology* 173.12 (2004): 7358-7367.
Khan, Tarique, and Dinakar M. Salunke. "Adjustable locks and flexible keys: plasticity of epitope-paratope interactions in germline antibodies." *The Journal of Immunology* 192.11 (2014): 5398-5405.
MacCallum, Robert M., Andrew CR Martin, and Janet M. Thornton. "Antibody-antigen interactions: contact analysis and binding site topography." *Journal of Molecular Biology* 262.5 (1996): 732-745.
Mariuzza, R. A., S. E. Phillips, and R. J. Poljak, "The structural basis of antigen-antibody recognition." *Annual Review of Biophysics and Biophysical Chemistry* 16 (1987): 139-159.
Piche-Nicholas, Nicole M., et al. "Changes in complementarity-determining regions significantly alter IgG binding to the neonatal Fc receptor (FcRn) and pharmacokinetics." *MAbs*. vol. 10. No. 1. Taylor & Francis, 2018.
Poosarla, Venkata Giridhar, et al. "Computational de novo design of antibodies binding to a peptide with high affinity," *Biotechnology and Bioengineering* 114.6 (2017): 1331-1342.
Rader, Christoph, David A. Cheresh, and Carlos P. Barbas III. "A phage display approach for rapid antibody humanization: designed combinatorial V gene libraries." *Proceedings of the National Academy of Sciences* 95.15 (1998): 8910-8915.
Uhlemann, L., W-M. Becker, and M. Schlaak. "Food allergy: Identification and characterization of peanut allergens with patients' sera and monoclonal antibodies." *Zeitschrift für Ernährungswissenschaft* 32 (1993): 139-151. Title and Summary.
Caldas, Cristina, et al. "Humanization of the anti-CD18 antibody 6.7: an unexpected effect of a framework residue in binding to antigen." *Molecular immunology* 39.15 (2003): 941-952.
Casadevall, Arturo, and Alena Janda. "Immunoglobulin isotype influences affinity and specificity." *Proceedings of the national academy of sciences* 109.31 (2012): 12272-12273.
Du, Jiamu, et al. "Molecular basis of recognition of human osteopontin by 23C3, a potential therapeutic antibody for treatment of rheumatoid arthritis." *Journal of molecular biology* 382.4 (2008): 835-842.
Kunik, Vered, Bjoern Peters, and Yanay Ofran. "Structural consensus among antibodies defines the antigen binding site." *PLOS computational biology* 8.2 (2012): e1002388.
Office Communication issued in European Application No. 18748576.8, dated Oct. 17, 2024.
Sela-Culang, Inbal, Vered Kunik, and Yanay Ofran. "The structural basis of antibody-antigen recognition." *Frontiers in immunology* 4 (2013): 302.
Winkler, Karsten, et al. "Changing the antigen binding specificity by single point mutations of an anti-p24 (HIV-1) antibody." *The Journal of Immunology* 165.8 (2000): 4505-4514.

\* cited by examiner

Figure 3A:
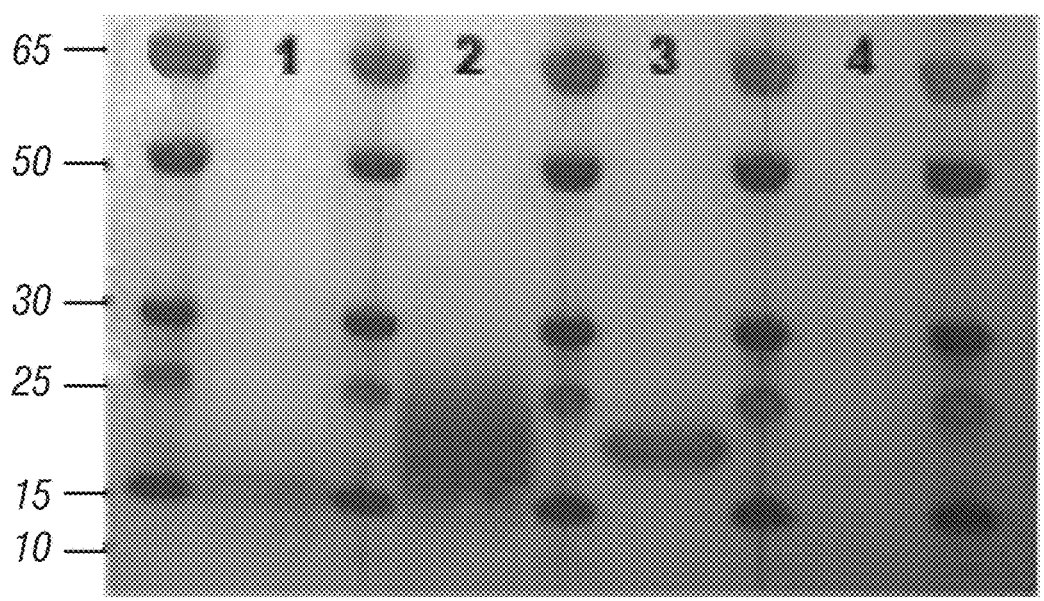

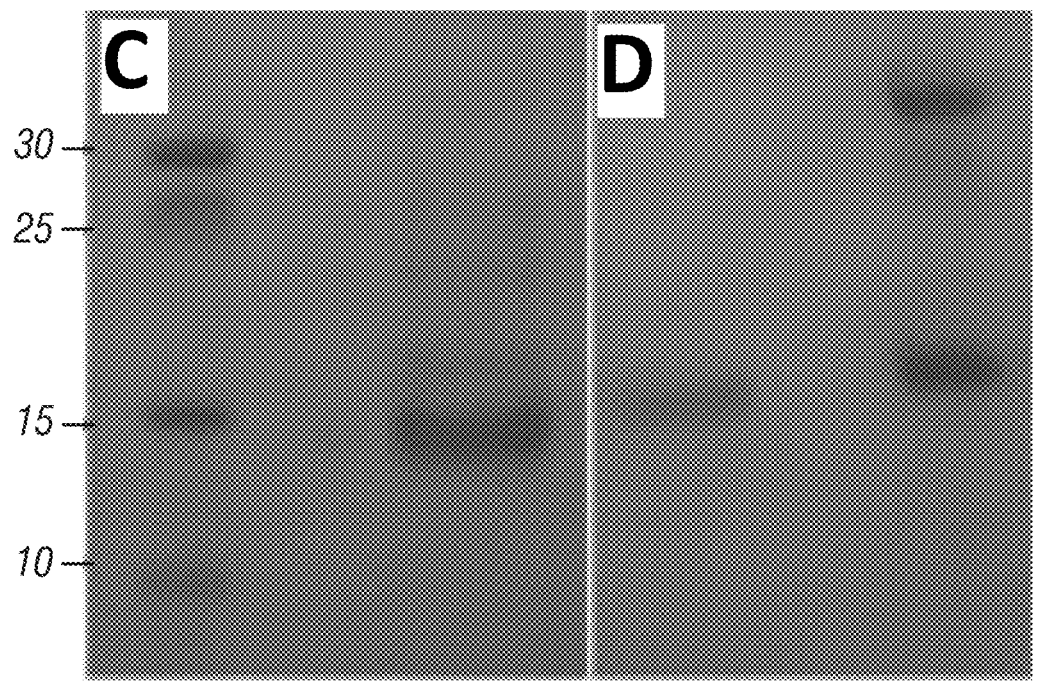
FIGS. 3C-D

**2G1 Binding to *Der p2***

$EC_{50}$ = 7.1 ng/mL

FIG. 4

Human anti-Ara h 2 IgE mAb induced anaphylaxis

- 5C5 & 13D9 (n=4)
- 13D9 & 15A4 (n=2)
- 5C5 & 15A4 (n=2)

% Survival vs Minutes after challenge

Human anti-Ara h 6 IgE mAb induced anaphylaxis

- 1H9 & 8F3 (n=4)
- 8F3 & 1A8 (n=1)
- 1H9 & 1A8 (n=2)

% Survival vs Minutes after challenge

FIG. 6

GENERATION OF HUMAN ALLERGEN- AND HELMINTH-SPECIFIC IGE MONOCLONAL ANTIBODIES FOR DIAGNOSTIC AND THERAPEUTIC USE

This application is a continuation of U.S. application Ser. No. 16/481,165, filed Jul. 26, 2019, which is a national phase application under 35 U.S.C. § 371 of International Application No. PCT/US2018/015870, filed Jan. 30, 2018, which claims benefit of priority to U.S. Provisional Application Ser. No. 62/452,603, filed Jan. 31, 2017, the entire contents of each of which are hereby incorporated by reference This invention was made with government support under grant nos. K08AI103038 and R21AI123307 awarded by the National Institutes of Health. The government has certain rights in the invention.

BACKGROUND

1. Field of the Disclosure

The present disclosure relates generally to the fields of medicine, allergies, and immunology. More particular, the disclosure relates to human IgE monoclonal antibodies binding to allergic targets such as dust mite antigens.

2. Background

The WHO estimates that there are 2 billion people (>25% of the total population) living with a soil-transmitted helminth infection world-wide (Food Allergy Among U.S. Children: Trends in Prevalence and Hospitalizations). Anti-helminth medications are highly effective and inexpensive, but reinfection occurs rapidly. A strategy that could prevent the initial acquisition or reinfection would prevent tremendous morbidity and mortality (Sicherer et al., 1999). Anti-helminth vaccines have been proposed to be the solution. Many groups and vaccine developers have taken on this challenge. However, there is a fundamental question regarding the human immune response to helminth infection that needs to be answered first. That question is whether the adaptive immune response, specifically the IgE antibody response, can naturally prevent infection or reduce worm bourdon in humans. As opposed to the allergen proteins driving allergic disease, the protein targets of the human anti-helminth IgE antibody response are almost completely unknown. To begin to answer this question, and a larger one regarding the overall role of IgE in human immune defense and disease, one must first understand what proteins are naturally supposed to be driving this branch of the antibody response.

The adaptive aspect of the human anti-helminth immune response is directed through the generation of specific IgE. This brings innate effecter cells, basophils and eosinophils, to the site of infection by FcɛRI receptors on the cell surface (Sicherer et al., 1999). However, there is very limited evidence that IgE plays any beneficial role in the process. It is difficult, if not impossible, to study IgE using human immune serum, given the complexity and exceedingly low concentration of antigenic protein-specific IgE. The best way to study whether IgE plays a beneficial role in the human anti-helminth immune response is to study naturally-occurring IgE at the molecular level. To do this, IgE monoclonal antibodies are needed, since monoclonal antibodies can be titrated with dose-dependency determined.

Parasitic worms are large, multi-cellular organisms that have coevolved within their human host for millions of years. It is not surprising that this relationship is maintained at a close equilibrium, where the worm is not always destroyed by the host, and the host is not killed by the worm. It is therefore also not surprising that studies of the human immune response often fail to demonstrate a protective effect. However, these studies are of vast mixtures of the antibody response and likely are confounded by features influenced by the worm. To study the affect that the adaptive arm of the human anti-helminth immune response plays in this complicated relationship, one must study each molecule and not the mixture. By performing studies on mAbs obtained from subjects infected with parasitic worms, one could develop a tremendous understanding of this system. The complexity of the response can even be dissected down to its singular components.

To have the ability to use naturally-occurring human IgE mAbs to study the pathogenesis of human helminth infection at the molecular level has been desired for many decades. There are three principle reasons why these antibodies have not been made and studied. The first reason is that techniques for efficiently making full-length (including the naturally-occurring Fc) human mAbs were not in place until several years ago. Advancements in electrical cytofusion protocols, stability of myeloma fusion partners, and improvements in commercially available hybridoma growth medium, have now made human hybridoma generation achievable.

The second reason is that the frequency of IgE-producing B cells in peripheral blood in most cases is exceedingly low. Techniques to make full-length naturally occurring human mAbs rely on the availability of peripheral blood B cells that encode the IgE antibody of interest. Because these cells are rare, the numbers that can be captured with a single blood draw are not sufficient for standard recombinant mAb technologies.

The third reason why naturally-occurring human IgE mAbs have not been studied is the difficulty in identifying and growing IgE-producing B cells in primary culture. There is strict regulation of IgE B cell receptor expression and soluble antibody secretion, suspected to involve CD23 (FcɛRII). This results in great difficulty when attempting to identify IgE B cells within PBMC samples by fluorescent labeling the B cell receptor (Achatz et al., 1997 and Karnowski et al., 2006). Most studies describing the identification of these cells use methods that destroy them—staining intracellular IgE by fixation and permeabilization of cell membranes. Also, primary cultures containing one clone of a B cell secreting IgE does so at levels below detection, even the most sensitive ELISA. For this reason, studies of IgE-expressing B cells in culture have only involved artificially class-switched polyclonal cultures using the cytokine IL4 (Avery et al., 2008 and Renz et al., 1990). Moreover, IgE generated using IL4 has no value for studying the target-specific human IgE antibody response since it causes class switching in a seemingly random way, and would theoretically result in antibodies that may never occur in nature (anti-measles virus IgE antibodies generated by artificially class-switching memory cells from the MMR vaccine).

For these reasons, it would be extremely advantageous to develop reliable methods for the production and isolated of IgE-producing hybridomas, thereby facilitation the production of an reserach with IgE monoclonal antibodies.

SUMMARY

Thus, in accordance with the present disclosure, there is provided a method of detecting a IgE antibody with binding affinity/specificity for a dust mite antigen in a subject comprising (a) providing a test antibody or fragment thereof having (i) heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251; (b) contacting the test antibody or fragment thereof with an antibody-containing sample from said subject in the presence of a dust mite antigen; and (c) detecting IgE antibody with binding affinity for dust mite antigen in said sample by measuring the reduction of binding to dust mite antigen by the test antibody or fragment thereof as compared to the binding of the test antibody or fragment thereof in the absence of said sample. The test antibody or fragment thereof may be an IgE antibody or IgG antibody, and the antibody fragment is a recombinant scFv (single chain fragment variable) antibody, Fab fragment, F(ab')$_2$ fragment, or Fv fragment.

The sample may a body fluid, such as blood, sputum, tears, saliva, mucous or serum, urine, exudate, transudate, tissue scrapings or feces. Detection may comprises ELISA, RIA or Western blot, and/or said detection may be quantitative. The method may further comprising performing steps (a) and (b) a second time and determining a change in antibody levels as compared to the first assay. The test antibody or fragment thereof may encoded by heavy and light chain variable sequences as set forth in (i) SEQ ID NOS: 13 and 14, or (ii) SEQ ID NOS: 15 and 16, or (iii) SEQ ID NOS: 47 and 48; may be encoded by heavy and light chain variable sequences having 70%, 80%, or 90% identity to heavy and light chain variable sequences as set forth in (i) SEQ ID NOS: 13 and 14, or (ii) SEQ ID NOS: 15 and 16, or (iii) SEQ ID NOS: 47 and 48; or may be encoded by heavy and light chain variable sequences having 95% identity to heavy and light chain variable sequences as set forth in (i) SEQ ID NOS: 13 and 14, or (ii) SEQ ID NOS: 15 and 16, or (iii) SEQ ID NOS: 47 and 48. The test antibody or fragment thereof may comprise heavy and light chain variable sequences as set forth in (i) SEQ ID NOS: 65 and 66, or (ii) SEQ ID NOS: 67 and 68, or (iii) SEQ ID NOS: 99 and 100, or may comprise heavy and light chain variable sequences having 70%, 80% or 90% identity to heavy and light chain variable sequences as set forth in (i) SEQ ID NOS: 65 and 66, or (ii) SEQ ID NOS: 67 and 68, or (iii) SEQ ID NOS: 99 and 100, or may comprise heavy and light chain variable sequences having 95% identity to heavy and light chain variable sequences as set forth in (i) SEQ ID NOS: 65 and 66, or (ii) SEQ ID NOS: 67 and 68, or (iii) SEQ ID NOS: 99 and 100.

In another embodiment, there is provided A method of detecting a IgE antibody with binding affinity/specificity for a helminth antigen in a subject comprising (a) providing a test antibody or fragment thereof having clone paired heavy and light chain CDRs from Tables C and D; (b) contacting the test antibody or fragment thereof with an antibody-containing sample from said subject in the presence of a helminth antigen; and (c) detecting IgE antibody with binding affinity for helminth antigen in said sample by measuring the reduction of binding to helminth antigen by the test antibody or fragment thereof as compared to the binding of the test antibody or fragment thereof in the absence of said sample. The sample may a body fluid, such as blood, sputum, tears, saliva, mucous or serum, urine, exudate, transudate, tissue scrapings or feces. Detection may comprise ELISA, RIA or Western blot, and/or said detection may be quantitative. The method may further comprising performing steps (a) and (b) a second time and determining a change in antibody levels as compared to the first assay. The test antibody or fragment thereof may be an IgE antibody or IgG antibody, and the antibody fragment is a recombinant scFv (single chain fragment variable) antibody, Fab fragment, F(ab')$_2$ fragment, or Fv fragment.

The test antibody or fragment thereof may be encoded by clone paired heavy and light chain variable sequences as set forth in Table A; may be encoded by heavy and light chain variable sequences having 70%, 80%, or 90% identity to clone paired heavy and light chain variable sequences as set forth in Table A, or may be encoded by heavy and light chain variable sequences having 95% identity to clone paired heavy and light chain variable sequences as set forth in Table A. The test antibody or fragment thereof may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B.

In yet another embodiment, there is provided a method of detecting an allergen or antigen in a sample comprising (a) providing a test antibody or fragment thereof having heavy chain CDR1-CDR3 and light chain CDR4-CDR6 from an IgE antibody produced in a subject in response to allergen or antigen stimulation; (b) contacting the test antibody or fragment thereof with a sample suspect of containing an allergen or antigen; and (c) detecting allergen or antigen in said sample by binding of the test antibody or fragment. The sample may be an environmental sample, or a food stuff. Detection may comprise ELISA, RIA or Western blot. Detection of said allergen or antigen may be quantitative.

The allergen may be a peanut allergen and the test antibody or fragment thereof may have (i) heavy chain CDR1 SEQ ID NO: 105, heavy chain CDR2 SEQ ID NO: 106, heavy chain CDR3 SEQ ID NO: 107, light chain CDR1 SEQ ID NO: 183, light chain CDR2 SEQ ID NO: 184 and light chain CDR3 SEQ ID NO: 185, or (ii) heavy chain CDR1 SEQ ID NO: 106, heavy chain CDR2 SEQ ID NO: 107, heavy chain CDR3 SEQ ID NO: 108, light chain CDR1 SEQ ID NO: 186, light chain CDR2 SEQ ID NO: 187 and light chain CDR3 SEQ ID NO: 188, or (iii) heavy chain CDR1 SEQ ID NO: 165, heavy chain CDR2 SEQ ID NO: 166, heavy chain CDR3 SEQ ID NO: 167, light chain CDR1 SEQ ID NO: 240, light chain CDR2 SEQ ID NO: 241 and light chain CDR3 SEQ ID NO: 242, or (iv) heavy chain CDR1 SEQ ID NO: 168, heavy chain CDR2 SEQ ID NO: 169, heavy chain CDR3 SEQ ID NO: 170, light chain CDR1 SEQ ID NO: 243, light chain CDR2 SEQ ID NO: 244 and light chain CDR3 SEQ ID NO: 245, or (v) heavy chain CDR1 SEQ ID NO: 171, heavy chain CDR2 SEQ ID NO: 172, heavy chain CDR3 SEQ ID NO: 173, light chain CDR1 SEQ ID NO: 246, light chain CDR2 SEQ ID NO: 247 and light chain CDR3 SEQ ID NO: 248.

The allergen may be a dust mite allergen and the test antibody or fragment thereof may have (i) heavy chain CDR1 SEQ ID NO: 123, heavy chain CDR2 SEQ ID NO:

124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251.

The antigen may be a helminth antigen and the test antibody or fragment thereof may be clone paired heavy and light chain CDRs from Tables C and D. The test antibody or fragment thereof may comprise clone paired heavy and light chain variable sequences as set forth in Table B, or heavy and light chain variable sequences having 70%, 80% or 90% of clone paired heavy and light chain variable sequences of Table B. The test antibody or fragment thereof may be an IgE antibody or IgG antibody, and the antibody fragment may be a recombinant scFv (single chain fragment variable) antibody, Fab fragment, F(ab')$_2$ fragment, or Fv fragment.

In still another embodiment, there is provided a method of preventing or treating a dust mite-related allergic reaction in a subject comprising delivering to said subject an IgG antibody or antibody fragment, wherein said antibody or antibody fragment has (i) heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202 and light chain CDR3 SEQ ID NO: 203, or (ii) heavy chain CDR1 SEQ ID NO: 126, heavy chain CDR2 SEQ ID NO: 127, heavy chain CDR3 SEQ ID NO: 128, light chain CDR1 SEQ ID NO: 204, light chain CDR2 SEQ ID NO: 205 and light chain CDR3 SEQ ID NO: 206, or (iii) heavy chain CDR1 SEQ ID NO: 174, heavy chain CDR2 SEQ ID NO: 175, heavy chain CDR3 SEQ ID NO: 176, light chain CDR1 SEQ ID NO: 249, light chain CDR2 SEQ ID NO: 250 and light chain CDR3 SEQ ID NO: 251. The antibody fragment may be a recombinant scFv (single chain fragment variable) antibody, Fab fragment, F(ab')$_2$ fragment, or Fv fragment, a chimeric antibody. The method may further comprise treating said subject with an anti-inflammatory agent, such as a steroid, an anti-histamine, and anti-leukotriene. The anti-inflammatory agent may be administered chronically. Delivering may comprise antibody or antibody fragment administration. Delivering may comprise genetic delivery with an RNA or DNA sequence or vector encoding the antibody or antibody fragment.

The antibody or antibody fragment may be encoded by heavy and light chain variable sequences as set forth in (i) SEQ ID NOS: 13 and 14, or (ii) SEQ ID NOS: 15 and 16, or (iii) SEQ ID NOS: 47 and 48; may be encoded by heavy and light chain variable sequences having 70%, 80%, or 90% identity to heavy and light chain variable sequences as set forth in (i) SEQ ID NOS: 13 and 14, or (ii) SEQ ID NOS: 15 and 16, or (iii) SEQ ID NOS: 47 and 48; or may be encoded by heavy and light chain variable sequences having 95% identity to heavy and light chain variable sequences as set forth in (i) SEQ ID NOS: 13 and 14, or (ii) SEQ ID NOS: 15 and 16, or (iii) SEQ ID NOS: 47 and 48. The antibody or antibody fragment may comprise heavy and light chain variable sequences as set forth in (i) SEQ ID NOS: 65 and 66 or (ii) SEQ ID NOS: 67 and 68, or (iii) SEQ ID NOS: 99 and 100; may comprise heavy and light chain variable sequences having 70%, 80% or 90% identity to heavy and light chain variable sequences as set forth in (i) SEQ ID NOS: 65 and 66 or (ii) SEQ ID NOS: 67 and 68, or (iii) SEQ ID NOS: 99 and 100; or may comprise heavy and light chain variable sequences having 95% identity to heavy and light chain variable sequences as set forth in (i) SEQ ID NOS: 65 and 66 or (ii) SEQ ID NOS: 67 and 68, or (iii) SEQ ID NOS: 99 and 100.

Also provided is a monoclonal antibody or antibody fragment comprises clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Another embodiment is a hybridoma or engineered cell encoding an antibody or antibody fragment wherein the antibody or antibody fragment is characterized by clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Still another embodiment involves a vaccine formulation comprising one or more IgG antibodies or antibody fragments characterized by clone paired heavy and light chain CDRs from Tables C and D. The antibody or antibody fragment may be encoded by clone paired heavy and light chain variable sequences from Table A, encoded by heavy and light chain variable sequences having 70%, 80%, or 90% identity to clone paired heavy and light chain variable sequences as set forth in Table A, or encoded by heavy and light chain variable sequences having 95% identity to clone paired heavy and light chain variable sequences as set forth in Table A. The antibody or antibody fragment may comprise clone paired heavy and light chain variable sequences as set forth in Table B, may comprise heavy and light chain variable sequences having 70%, 80% or 90% identity to clone paired heavy and light chain variable sequences as set forth in Table B, or may comprise heavy and light chain variable sequences having 95% identity to clone paired heavy and light chain variable sequences as set forth in Table B. The antibody fragment may be a recombinant scFv (single chain fragment variable) antibody, Fab fragment, F(ab')$_2$ fragment, or Fv fragment, or is a chimeric antibody, a bispecific antibody. The antibody may be an IgE, or is an IgG comprising grafted IgE CDRs or variable regions. The antibody or antibody fragment may further comprise a cell penetrating peptide and/or is an intrabody.

Still yet another embodiment is a method of generating a hydridoma that produces an IgE antibody comprising (a) activating one or more peripheral blood mononuclear cells (PBMC's) with rh-IL-21, CD40L and BAFF; (b) screening the activated cell or cells of step (a) for IgE expression; (c) fusing one or more IgE-expressing PMBCs identified in step (b) with an immortal cell; (d) subjecting a fused cell or cells of step (c) to selection for a fusion event; (e) screening one or more selected fused cells of step (d) binding to an antigen; (f) cloning one or more selected fused cells positive for antigen binding; and (g) propagating one or more cloned cells of step (f). The method may further comprise obtaining IgE antibody produced from the one or more cloned cells of step (g). The method may further comprise obtaining a PMBC-containing sample from a subject prior to step (a). The method may further comprise isolating one or more PMBCs from a blood sample prior to step (a). Step (d) may comprise an ELISA. Cloning may comprise limiting dilution and/or flow cytometry. The antigen may be a parastic worm antigen, such as *Wuchereria bancrofti* or *Stronglyoides stercoralis*. The antigen may be an allergen, such as a mold antigen, a dust mite antigen, an insect venom, an antibiotic, a food antigen, or an animal antigen.

A still further embodiment comprises a method of desensitizing a subject to an allergen comprising (a) administering to said subject an allergen; and (b) administering to said subject an IgG antibody that has a binding specificity to said allergen obtained from an IgE antibody. The allergen and IgG antibody may be mixed together prior to administering, or maybe administered to said subject separately. The allergen and IgG antibody may be administered to said subject multiple times. The subject may be a human or a non-human mammal. The allergen maybe administered with an adjuvant.

Additionally, there is provided a method of producing an IgG immune response to an allergen comprising (a) identifying an IgE epitope in an allergen by mapping the binding of an IgE antibody binding site; (b) modifying one or more residues in said IgE antibody binding site to reduce or eliminate IgE antibody binding to said binding site, thereby producing a hypoallergenic allergen; (c) immunizing a subject with said hypoallergenic allergen to produce and IgG resopnse to said hypoallegenic allergen, while producing a reduced or no IgE response as compared to the allergen of step (a). The allergen may be a mold allergen, a dust mite allergen, an insect venom, an antibiotic, a food allergen, or an animal allergen. The IgE antibody binding to said binding site may be reduced by at least 90%. The IgE antibody binding to said binding site may be eliminated. The hypoallergenic allergen may be administered to said subject with an adjuvant and/or is administered multiple times.

Another embodiment comprises a method of identifying an IgE antigen comprising (a) obtaining an IgE-producing B cell; (b) immortalizing said IgE-producing B cell; (c) obtaining monoclonal IgE from the immortalized B cell of step (b); (d) identifying an antigen that binds to said monoclonal IgE. The antigen may be an allergen, such as a mold allergen, a dust mite allergen, an insect venom, an antibiotic, a food allergen, or an animal allergen. The antigen may be a parastitic worm antigen. The method may further comprise producing a vaccine that lacks said IgE epitope.

In still a further embodiment, there is provided a method for quantifying an allergen in an extract used for allergen vaccination. Human IgE mAbs, or IgG mAbs produced therefrom, can be used to accurately quantify the amount of the specific allergen(s) in each lot of extract so that one can adjust the concentration, thus standardizing the extract. This would permit the practitioner to inject a patient with a specific known amount of allergen rather than an unknown amount that given that quantities change with every lot manufactured. In general, the method would comprise (a) providing a test antibody or fragment thereof having heavy chain CDR1-CDR3 and light chain CDR4-CDR6 with binding specificity for an allergen, or a mixture of antibodies with varying allergen specificity; (b) contacting the test antibody or fragment thereof or mixture with a vaccine extract; and (c) quantifying the allergen or allergens in said sample by binding of the test antibody or fragment thereof or mixture. The sample may be an environmental sample, or a food stuff. Detection may comprise ELISA, RIA or Western blot.

Still an additional embodiment comprises a method of determining the antigenic integrity of an antigen comprising (a) contacting a sample comprising said antigen with a first antibody or antibody fragment having clone-paired heavy and light chain CDR sequences from Tables C and D, respectively; and (b) determining antigenic integrity of said antigen by detectable binding of said antibody or antibody fragment to said antigen. The sample may comprise recombinantly produced antigen, or a vaccine formulation or vaccine production batch. The detection may comprise ELISA, RIA, western blot, a biosensor using surface plasmon resonance or biolayer interferometry, or flow cytometric staining. The first antibody or antibody fragment may be encoded by clone-paired variable sequences as set forth in Table A, may be encoded by light and heavy chain variable sequences having 70%, 80%, or 90% identity to clone-paired variable sequences as set forth in Table A, or may be encoded by light and heavy chain variable sequences having 95% identity to clone-paired sequences as set forth in Table A. The first antibody or antibody fragment may comprise light and heavy chain variable sequences according to clone-paired sequences from Table B, or may comprise light and heavy chain variable sequences having 70%, 80% or 90% identity to clone-paired sequences from Table B, or may comprise light and heavy chain variable sequences having 95% identity to clone-paired sequences from Table B. The first antibody fragment may be a recombinant ScFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen with an antibody or antibody fragment having clone-paired heavy and light chain CDR sequences from Tables C and D, respectively; and (d)

determining antigenic integrity of said antigen by detectable binding of said antibody or antibody fragment to said antigen. The second antibody or antibody fragment may be encoded by clone-paired variable sequences as set forth in Table A, may be encoded by light and heavy chain variable sequences having 70%, 80%, or 90% identity to clone-paired variable sequences as set forth in Table A, or may be encoded by light and heavy chain variable sequences having 95% identity to clone-paired sequences as set forth in Table A. The second antibody or antibody fragment may comprise light and heavy chain variable sequences according to clone-paired sequences from Table B, may comprise light and heavy chain variable sequences having 70%, 80% or 90% identity to clone-paired sequences from Table B, or may comprise light and heavy chain variable sequences having 95% identity to clone-paired sequences from Table B. The second antibody fragment may be a recombinant ScFv (single chain fragment variable) antibody, Fab fragment, F(ab')$_2$ fragment, or Fv fragment. The method may further comprise performing steps (c) and (d) a second time to determine the antigenic stability of the antigen over time.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present disclosure. The disclosure may be better understood by reference to one or more of these drawings in combination with the detailed description of specific embodiments presented herein.

FIG. 1. Human IgE hybridoma generation scheme. After PBMCs are isolated from patient blood, cells are grown in 96 well tissue culture plates for 7 days before primary screening by ELISA. Cells within wells containing IgE are then fused to a myeloma partner by electrical cytofusion. Human hybridomas are selected for in HAT medium and biologically cloned using flow cytometric single cell sorting. Finally, IgE secreting hybridomas are grown in serum free medium before monoclonal IgE antibody purified by Omalizumab chromatography.

FIG. 2. Purification of human anti-helminth IgE mAbs Human IgE mAb 10H9 was purified using Omalizumab immunoaffinity chromatography. A 4-12% Bis-Tris SDS-PAGE was run under reducing-denaturing conditions, stained with Coomassie brilliant blue. Lane 1: molecular weight marker, lanes 4 (5 mg), 5 (10 mg), and 6 (15 mg) show IgE mAb 10H9 heavy and light chains, seen around 70 kDa and 25 kDa, respectively. Isotype control mAbs Omalizumab (IgG), lane 2, and U266 (IgE), lane 3, are shown for comparison.

FIGS. 3A-D. Western blot and identification of the helminth protein targets. (FIG. 3A) Helminth lysate Western blotted with IgE mAbs 1A5 (lane 1), 14B2 (lane 2), 11H12 (lane 3), and 7G12 (lane 4). (FIG. 3B) MAb 1A5 was amine coupled to NHS activated HiTRAP column. (FIGS. 3C-D) Chromatography performed using *Wuchereria bancrofti* lysate. The eluted helminth protein target used for mass spectrometry is shown on SDS-PAGE in panel C (20 μL) and Western blot in panel D (1 μL).

Figure 4:
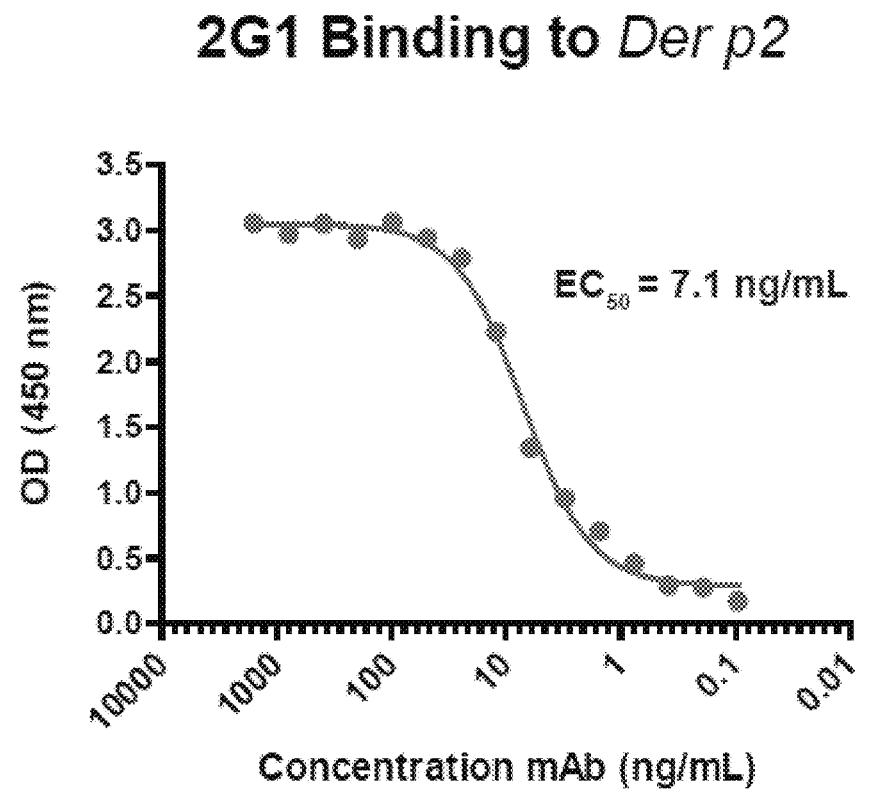

FIG. 4. Human IgE mAb 2G1 binding to allergen Der p2. Purified natural dust mite allergen Der p2 (Indoor Biotech; NA-DF2-1) was used at 5 μg/mL to coat plates overnight. Human IgE mAb 2G1 was added in a two-fold dilution series. Murine anti-human IgE secondary antibody (Southern Biotech; 9160-05) then was added. TMB-Ultra substrate (Thermo; 34029) was used (OD 450 nm). All dilutions done in duplicate. Half maximal effective concentration ($EC_{50}$) calculated and found to be 7.1 ng/mL.

FIG. 5. Anaphylaxis induced by human anti-Asp f 1 IgE mAbs. Transgenic mouse line expressing FcεRIα were sensitized by IP injection of 100 μg total human anti-Asp f 1 IgE mAbs. Mice were challenged 72 h later by IP injection with predetermined maximal tolerated doses of *Aspergillus fumigatus* allergen extract. Change in temperature from baseline was monitored using implanted temperature probes.

FIG. 6. Anaphylaxis induced by human anti-peanut IgE mAbs. Transgenic mouse line expressing FcεRIα were sensitized by IP injection of 100 μg total human anti-peanut IgE mAbs. Mice were challenged 72 h later by IP injection with predetermined maximal tolerated doses of ALK peanut allergen extract. Time till death from anaphylactic shock was determined and recorded when the animal stopped moving and had no heartbeat.

DESCRIPTION OF ILLUSTRATIVE EMBODIMENTS

As discussed above, there is little known about the role of IgE in immunity and disease. This is in part due to the fact that the ability to study IgE antibodies is hampered by the inability to product monoclonal IgE antibodies using traditional hybridoma technology. The advancements described in this application now allow, for the very first time, the identification, amplification, and ultimately the generation of stable cell lines, human IgE-producting hybridomas, from this very rare population of helminth specific B cells in peripheral blood of infected subjects.

With the ability to generate full-length naturally occurring human anti-helminth IgE mAbs, it is possible to proceed with studies of the most basic, and critical, molecular interactions that make up the human anti-helminth antibody response. Having these tools will set in motion a new field of study and provide many insights that will allow for the design and development of new helminth vaccines and a better understanding of allergy.

These and other aspects of the disclosure are described in detail below.

I. IGE ANTIBODIES

A. Biology

Immunoglobulin E (IgE), first discovered in 1966, is a kind of antibody (or immunoglobulin (Ig) "isotype") that has only been found in mammals. IgE is synthesised by plasma cells. Monomers of IgE consist of two heavy chains (ε chain) and two light chains, with the ε chain containing 4 Ig-like constant domains (Cε1-Cε4). IgE's main function is immunity to parasites such as helminths like *Schistosoma mansoni, Trichinella spiralis*, and *Fasciola hepatica*. IgE is utilized during immune defense against certain protozoan parasites such as *Plasmodium falciparum*.

IgE also has an essential role in type I hypersensitivity, which manifests in various allergic diseases, such as allergic asthma, most types of sinusitis, allergic rhinitis, food allergies, and specific types of chronic urticaria and atopic dermatitis. IgE also plays a pivotal role in responses to allergens, such as: anaphylactic drugs, bee stings, and antigen preparations used in desensitization immunotherapy.

Although IgE is typically the least abundant isotype—blood serum IgE levels in a normal ("non-atopic") individual are only 0.05% of the Ig concentration, compared to 75% for the IgGs at 10 mg/ml, which are the isotypes responsible for most of the classical adaptive immune response—it is capable of triggering the most powerful inflammatory reactions.

IgE primes the IgE-mediated allergic response by binding to Fc receptors found on the surface of mast cells and basophils. Fc receptors are also found on eosinophils, monocytes, macrophages and platelets in humans. There are two types of Fcε receptors, FcεRI (type I Fcε receptor), the high-affinity IgE receptor, and FcεRII (type II Fcε receptor), also known as CD23, the low-affinity IgE receptor. IgE can upregulate the expression of both types of Fcε receptors. FcεRI is expressed on mast cells, basophils, and the antigen-presenting dendritic cells in both mice and humans. Binding of antigens to IgE already bound by the FcεRI on mast cells causes cross-linking of the bound IgE and the aggregation of the underlying FcεRI, leading to the degranulation and the release of mediators from the cells. Basophils, upon the cross-linking of their surface IgE by antigens, release type 2 cytokines like interleukin-4 (IL-4) and interleukin-13 (IL-13) and other inflammatory mediators. The low-affinity receptor (FcεRII) is always expressed on B cells; but IL-4 can induce its expression on the surfaces of macrophages, eosinophils, platelets, and some T cells.

There is much speculation into what physiological benefits IgE contributes, and, so far, circumstantial evidence in animal models and statistical population trends have hinted that IgE may be beneficial in fighting gut parasites such as *Schistosoma mansoni*, but this has not been conclusively proven in humans. Epidemiological research shows that IgE level is increased when infected by *Schistosoma mansoni, Necator americanus*, and nematodes in human. It is most likely beneficial in removal of hookworms from the lung.

Although it is not yet well understood, IgE may play an important role in the immune system's recognition of cancer, in which the stimulation of a strong cytotoxic response against cells displaying only small amounts of early cancer markers would be beneficial. If this were the case, anti-IgE treatments such as omalizumab (for allergies) might have some undesirable side effects. However, a recent study, which was performed based on pooled analysis using comprehensive data from 67 phase I to IV clinical trials of omalizumab in various indications, concluded that a causal relationship between omalizumab therapy and malignancy is unlikely.

Atopic individuals can have up to 10 times the normal level of IgE in their blood (as do sufferers of hyper-IgE syndrome). However, this may not be a requirement for symptoms to occur as has been seen in asthmatics with normal IgE levels in their blood—recent research has shown that IgE production can occur locally in the nasal mucosa.

IgE that can specifically recognize an "allergen" (typically this is a protein, such as dust mite Der p 1, cat Fel d 1, grass or ragweed pollen, etc.) has a unique long-lived interaction with its high-affinity receptor FcεRI so that basophils and mast cells, capable of mediating inflammatory reactions, become "primed", ready to release chemicals like histamine, leukotrienes, and certain interleukins. These chemicals cause many of the symptoms are associated with allergy, such as airway constriction in asthma, local inflammation in eczema, increased mucus secretion in allergic rhinitis, and increased vascular permeability, it is presumed, to allow other immune cells to gain access to tissues, but which can lead to a potentially fatal drop in blood pressure as in anaphylaxis. IgE is known to be elevated in various autoimmune disorders such as lupus (SLE), rheumatoid arthritis (RA) and psoriasis, and is theorized to be of pathogenetic importance in RA and SLE by eliciting a hypersensitivity reaction.

Regulation of IgE levels through control of B cell differentiation to antibody-secreting plasma cells is thought to involve the "low-affinity" receptor FcεRII, or CD23. CD23 may also allow facilitated antigen presentation, an IgE-dependent mechanism whereby B cells expressing CD23 are able to present allergen to (and stimulate) specific T helper cells, causing the perpetuation of a Th2 response, one of the hallmarks of which is the production of more antibodies.

Diagnosis of allergy is most often done by reviewing a person's medical history and finds a positive result for the presence of allergen specific IgE when conducting a skin or blood test. Specific IgE testing is the proven test for allergy detection; evidence does not show that indiscriminate IgE testing or testing for immunoglobulin G (IgG) can support allergy diagnosis.

B. IgE and its Role in Helminthic Immunity

A major branch of the mammalian immune system has evolved to deal with helminth infections, known as type-2 immunity. Both the innate (basophils and eosinophils) and adaptive (CD4+ T cells and B cells) arms are heavily involved. Studies, primarily using murine animal model systems, have shown that this host immune response plays a critical role in trying to kill and expel the adult parasite as well as reducing survival of parasites during secondary infection (Finkelman, et al., 2004; Voehringer et al., 2006; Herbert et al., 2004; Abraham et al., 2004; Gurish et al., 2004 and King et al., 1997). Massive epidemiologic studies have conclusively demonstrated a clear link between helminth infection and eosinophilia and elevated levels of IgE. Thus it is clear that this branch of human immunity is induced, but what benefits are provided, if any, by IgE is not known. There is only sparse data that link the levels of IgE directed toward the helminth and infection rates or worm burden in humans (McSharry et al., 1999; Turner et al., 2005 and Turner et al., 2003). Therefore the role of IgE in protective immunity against helminth parasites is not clear, but it may be contributing to aspects of host immunity such as life-cycle stages, re-infection, or a specific helminth parasite (Hagan et al., 1991). A randomized controlled trial tested the effect of anti-IgE therapy (Omalizumab) in populations at risk of helminth infection. Although numbers were small, treatment did not appear to be associated with increased morbidity attributable to helminth infection (Cruz et al., 2007).

One group of helminth proteins, which are known targets of the human immune response, studied by several groups as potential vaccine candidate proteins, are the nematode polyprotein allergens (NPAs). NPAs are unusual lipid-binding proteins found only in nematodes that are felt to play roles in nutrient scavenging, immunomodulation, and IgE antibody responses to infection. NPAs are the target of strong immune responses, often associated with hypersensitivities. The most extensively studied of these is ABA-1, which is the most abundant protein in the body fluid of *Ascaris lumbricoides*. Epidemiological data using patient serum suggest that IgE antibody responses to ABA-1 are associated with the development of resistance to the infection (McSharry et al., 1999).

Nearly all of the field's understanding of the natural anti-helminth IgE antibody has come from the very low concentration present in infected patients' serum. Serum contains an immeasurable mixture of antibodies, which have many protein specificities, target untold numbers of epitopes, and have different affinities. This results in the inability to accurately study the molecular interaction of IgE with its target antigen. Since there are no natural antigen-specific human IgE mAbs, there are no controls to determine the accuracy/inaccuracy of any study that uses serum. Since there are no IgE mAbs that represent the molecules being tested in human serum, there are no means to verify/calibrate any assay with any degree of certainty. Serum has been used to study the helminth-specific IgE antibody response (Nutman et al., 1989; Lee et al., 1990; McCarthy et al. 1994 and Mitre et al., 2004). Several longitudinal studies aimed at measuring parasite-specific IgE levels during helminth infection have been performed (Chapa-Ruiz et al., and Steel, 1991).

The persistence of B cell memory was evaluated for antigen-specific IgE responses years after treatment of human filarial infections (Mitre and Nutman, 2006). Interestingly, frequencies of *Wuchereria bancrofti* antigen-specific IgE serum levels decreased significantly over time, but remained detectable in the majority of patients years after definitive treatment. More importantly they showed presence of circulating memory B cells producing helminth-specific IgE antibodies—using B cell ELISPOT analysis. Lastly, using affinity-purified serum IgE from a patient with a filarial parasitic infection, a major allergen y-glutamyl transpeptidase was identified (Lobos et al., 1996). These studies provide evidence that helminth-specific circulating memory B cells remain following elimination of the infection and will be available for us to culture and study.

The hygiene hypothesis suggests that helminth infection might modulate the host immune response and decrease responsiveness to innocuous environmental proteins (Strachan, 1989 and Liu and Leung, 2006). Indeed, helminth-infected individuals have been found to have an overall lower prevalence of allergic disease in several studies (Cooper et al., 2003; Rodrigues et al., 2008 and van den Biggelaar et al., 2000). However, many other studies have demonstrated an increase in allergic disease in helminth-infected individuals, particularly when looking at asthma (Hagel et al., 2007; Wordemann et al., 2008 and Leonardi-Bee et al., 2006). This discrepancy may be explained by the phenomenon of cross-sensitization (phenomena often seen with allergens). Homology exists between some helminth proteins and allergens, and theoretically could be bound by the same IgE molecule. In fact, cross-sensitization due to homology between helminth proteins and allergen proteins has been shown using serum. The two most studied of these are the tropomyosin and glutathione-S-transferase proteins found in dust mite, *Dermatophagoides pteronyssinus*. Using allergic patient serum, the human IgE-binding components in *Ascaris* extract were identified using mass spectroscopy, confirming the IgE cross-reactivity between these parasitic worm proteins and dust mite allergens (Acevedo et al., 2009). More recently cross-reactivity was also shown between a major glutathione-S transferase allergen of cockroach and the protein homolog found in *Wuchereria bancrofti* (Santiago et al., 2012; Santiago et al., 2012 and Santiago et al., 2015). Since all of these studies use polyclonal serum, the epitopes, affinity toward helminth versus crossreactive allergen protein, and the functional significance of this cross-sensitization phenomenon cannot be studied further. Having natural human helminth protein specific IgE mAbs will allow us to study the molecular mechanisms underlying this effect.

C. IgE-Mediated Allergic Diseases

The allergic response itself offers no evident advantage and is instead understood to be a side effect of the primary function of the IgE class of antibodies: to prevent infection by helminth worms (such as hookworm and schistosomes). Through mechanisms that are yet to be elucidated, allergens appear to be innocuous antigens that inappropriately produce an IgE antibody response that is typically specific for helminths.

For more than 50 years, the prevalence of allergic diseases has risen steadily in the industrialized world (Food Allergy Among U.S. Children: Trends in Prevalence and Hospitalizations. In the US, allergy is the fifth leading chronic disease in people of all ages and the third most common chronic disease in children (Sicherer et al., 1999 and American Academy of Allergy Asthma and Immunology: Food Allergy). IgE-mediated allergic diseases include: asthma, atopic dermatitis, allergic rhinitis, allergic conjunctivitis, anaphylaxis, drug allergies, insect venom allergies, etc. These diseases are invoked and perpetuated by proteins contained in an array of plant and animal species that humans are exposed to on a daily basis. These allergen proteins exist in things like: foods, venoms, drugs, trees, molds, mites, cockroaches, dogs, cats, latex, etc. Although allergy is among our country's most common diseases, it is often overlooked. New diagnostics and therapeutics are needed. Gaining a basic understanding of the molecular interactions at the heart of the pathogenesis of allergic diseases will open up new strategies for developing allergy diagnostics and therapeutics.

Asthma affects nearly 300 million individuals worldwide, about 25 million people in the U.S. alone. It affects all age groups, but it is children that are at the highest risk, with a prevalence that is rapidly growing. Asthma is the most prevalent cause of childhood disability in the U.S., and affects the poor disproportionately. Despite the prevalence, significant morbidity, and cost of this disease, little progress has been made with regard to understanding the pathogenesis or development of new strategies for treatment or prevention. Many of the allergens responsible for asthma are also associated with allergic rhinitis, affects between 10 and 30 percent of the population in developed countries. The most common indoor/outdoor triggers are: dust mites, cockroaches, and cat, dog and rodent dander. Also of great importance, particularly in the case of allergic rhinitis, are: trees, grasses, weed pollens, and mold spores.

Skin allergies are also very common and are one of the most important groups of allergic diseases that include eczema, hives, chronic hives and contact allergies. In the U.S., 8.8 million children have skin allergies, affecting the very young (age 0-4) disproportionately. Primary allergen culprits again include contact with dust mites and cockroaches, foods or even latex.

The most recent estimates suggest that up to 15 million Americans have allergies to food, and this number is rapidly rising. The Centers for Disease Control and Prevention reported that food allergies among children increased about 50% between 1997 and 2011, but there is no clear answer as to why (Food Allergy Among U.S. Children: Trends in Prevalence and Hospitalizations). The Centers for Disease Control also reported that food allergies result in more than 300,000 ambulatory-care and more than 200,000 emergency department visits a year among children (Sicherer et al., 1999). The economic cost of food allergies in children has reached nearly $25 billion per year. Food allergy is the leading cause of anaphylaxis outside the hospital setting. Eight foods account for 90 percent of all reactions: milk, eggs, peanuts, tree nuts, soy, wheat, fish and shellfish. Peanut and tree nut allergies, which tend to develop in childhood, are usually life-long, whereas cow's milk, egg and soy allergies are eventually outgrown. Approximately 3 million people report allergies to peanuts and tree nuts (Sicherer et al., 1999). The number of children living with peanut allergy has tripled between 1997 and 2008. There is no cure for food allergies. Strict avoidance of food allergens and early recognition and management of allergic reactions is the current strategy applied in clinical practices around the world. Unfortunately, even trace amounts of a food allergen can cause a reaction.

Despite the fact that IgE causes so much human suffering in the form of allergic disease, it was not until 1967 before the "reagin" molecule was discovered (Johansson and Bennich, 1967). This is due to its very low serum concentration relative to other antibody isotypes—over one hundred thousand fold less than IgG in healthy individuals. Only one IgE secreting cell line (U266), or its derivatives (SKO-007), has been available to study—the atypical multiple myeloma described in the original paper (Johansson and Bennich, 1967 and Olsson and Kaplan, 1980). This IgE molecule has been of integral importance, used in thousands of studies as a reagent or for the generation of reagents. However, its target has never been identified, thus forcing investigators who wish to study the naturally-occurring IgE antibody response to use polyclonal serum.

II. MONOCLONAL ANTIBODIES AND PRODUCTION THEREOF

A. General Methods

It will be understood that IgE monoclonal antibodies will have several applications. These include the production of diagnostic kits for use in detecting and diagnosing parasitic worm infections and environmental allergens, as well as for treating the same. In these contexts, one may link such antibodies to diagnostic or therapeutic agents, use them as capture agents or competitors in competitive assays, or use them individually without additional agents being attached thereto. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

In the case of human antibodies against natural pathogens, a suitable approach is to identify subjects that have been exposed to the pathogens, such as those who have been diagnosed as having contracted the disease, or those who have been vaccinated to generate protective immunity against the pathogen. Circulating anti-pathogen antibodies can be detected, and antibody producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens or lymph nodes, or from circulating blood. The antibody-producing B lymphocytes from the immunized animal are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984).

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986).

Fusion procedures usually produce viable hybrids at low frequencies, about $1\times10^{-6}$ to $1\times10^{-8}$. However, this does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine. Ouabain is added if the B cell source is an Epstein Barr virus (EBV) transformed human B cell line, in order to eliminate EBV transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection. When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonals. For this, RNA can be isolated from the hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using viral antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. Antibodies of the Present Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. Here, antibodies with specificity for dust mite antigens are provided.

House dust mites are globally ubiquitous and possess a number of allergen proteins associated with important allergic diseases such as allergic asthma and allergic rhinitis. Dust mite allergen sensitization occurs in the first few years of life and is ultimately associated with poor long-term respiratory health. In fact, house dust mite allergens appear to play an important role in the childhood progression (often called the allergic march) from allergic rhinitis to asthma. In the U.S., studies of all ages have shown the highest prevalence of sensitization to the dust mites *Dermatophagoides pteronyssinus* (37%) and *Dermatophagoides farinae* (34%). These mites can coexist in most geographical areas; *D. pteronyssinus* prefers a temperate climate while *D. farinae* can tolerant drier climates. There are approximately 24 known allergens present in the dust mite that have been shown to evoke IgE antibody responses in humans. However, the major allergen proteins Der p1 and Der f1 (group 1 allergens), Der p2 and Der f2 (group 2 allergens) are found to have the highest IgE binding frequencies, approximating 80% of sensitized humans. Both Der p1 and Der p2 products of a single gene, however, the proteins exist as a number of isoforms. Allergen extracts prepared from *Dermatophagoides* Spp. contain high concentrations of the Group 1 and 2 allergens, between 20 and 100 µg/ml. The major group 1 mite allergens, Der p1 and Der f1 exhibit protease activity, which is felt to contribute to their strong allergenicity, stimulating innate immunity. Both group 1 and group 2 proteins are very small, approximately 24 and 14 kDa respectively, and their structures have been solved by x-ray crystallography. Genetic engineering of dust mite allergens to reduce their human IgE reactivity, but retaining T cell reactivity, is a goal of the allergy field. Generating hypoallergenic allergen proteins offers a novel therapeutic approach to improving the safety and efficacy of allergen immunotherapy.

In another aspect, there are provided monoclonal antibodies having clone-paired CDR's from the heavy and light chains as illustrated in Tables 3 and 4, respectively. Such antibodies may be produced by the clones discussed below in the Examples section using methods described herein. These antibodies bind to dust mite antigens that are discussed above.

In yet another aspect, the antibodies may be defined by their variable sequence, which include additional "framework" regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table A and the amino acid sequences of Table B.

C. Engineering of Antibody Sequences

In various embodiments, one may choose to engineer sequences of the identified antibodies for a variety of reasons, such as improved expression, improved cross-reactivity or diminished off-target binding. A particularly useful engineering of the disclosed IgE antibodies will be those converted into IgG's. The following is a general discussion of relevant techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full length IgG antibodies were generated by subcloning heavy and light chain Fv DNAs from the cloning vector into an IgG plasmid vector, transfected into 293 Freestyle cells or CHO cells, and antibodies were collected an purified from the 293 or CHO cell supernatant.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. Such antibody derivatives are monovalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (–0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (–0.4), sulfur containing amino acids: cysteine (–1.0) and methionine (–1.3); hydrophobic, nonaromatic amino acids: valine (–1.5), leucine (–1.8), isoleucine (–1.8), proline (–0.5±1), alanine (–0.5), and glycine (0); hydrophobic, aromatic amino acids: tryptophan (–3.4), phenylalanine (–2.5), and tyrosine (–2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated fucntions such as complement activation, antibody dependent cellular cytotoxicity (ADCC), and FcR-mediated phagocytosis.

Of central importance to the present disclosure is isotype modification involving changing a naturally occurring human IgE isotype variable sequence to an IgG isotype. By making this unnatural modification of the IgE antibody, a pathogenic molecule can be made to possess therapeutic functions. Aside from the theoretical benefit that IgE isotype antibodies may have in control of helminth infections, IgE antibodies are necessary for causing IgE-mediated allergy. The function of an IgE antibody is conveyed through its Fc region, which directs binding of the antibody to specific Fc receptors on various cells. By changing a natural human IgE to an IgG, one completely alters the Fc receptors that can be engaged—this has never been shown to occur naturally in humans since the IgG isotypes are deleted from the B cell DNA when it class-switched to IgE. It is the IgE antibody's ability to bind the Fc receptors, FcεRI and FcεRII, which endow its pathogenic function. By engineering a human IgE variable sequence into an IgG antibody isotype, the pathogenic molecule can no longer perform its harmful functions. Additionally, the engineered IgG antibody can then provide new, therapeutic functions through engagement with various Fcγ receptors, such as those found on the mast cell, including FcγRIIB IgG antibodies that bind FcγRIIB on the surface of mast cells result in inhibitory signaling and inhibition of mediator release. For example, an allergen specific IgE antibody bound to FcεRI on mast cells will signal the release of inflammatory mediators upon binding its specific allergen—resulting in the diseases associated with allergy. However, an IgG made from the allergen-specific IgE variable sequences would bind FcγRIIB on mast cells and inhibit mediator release upon binding the specific disease inciting allergen.

Other types of modifications include residue modification designed to reduce oxidation, aggregation, deamidation, and immunogenicity in humans. Other changes can lead to an increase in manufacturability or yield, or reduced tissue cross-reactivity in humans.

Modified antibodies may be made by any technique known to those of skill in the art, including expression through standard molecular biological techniques, or the chemical synthesis of polypeptides. Methods for recombinant expression are addressed elsewhere in this document.

D. Single Chain Antibodies

A Single Chain Variable Fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alaine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5\times10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stablizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

E. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage diplay and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

F. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies is bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

G. IgE Antibody Generation Protocols

The following are a series of exemplary protocols for use in practicing the disclosed methods and producing the disclosed compositions.

(i) Hybridoma Process Outline
1. Growth and maintenance of rh-IL-21, CD40L, BAFF-NIH3T3 cells (NIH3T3)
2. Growth and maintenance of HMMAs (HMMA2.5)
3. Isolation of subject PBMCs from blood
4. NIH3T3 activation of B-cells from subject PBMCs (96-well-plates)
5. ELISA screening of NIH3T3 activated B-cell cultures (384-well format)
6. HMMA cytofusion and plating in growth medium (cells in 384-well-plates)
7. HAT selection medium is added
8. ELISA screening of hybridomas (384-well format)
9. Limiting dilution/enrichment dilution and flow cytometric sorting (384-well format)
10. ELISA screening of limiting dilution products
11. Transfer IgE positive hybridomas to a 48-well plate
12. Freeze back an aliquot then do an ELISA on 48-well plates (96-well format)
13. Transfer IgE positive hybridomas to a 12-well plate
14. Transfer IgE positive hybridomas to a T-75 flask
15. Grow final clonal hybridoma in 1L SFM in 4×T-225 flasks
16. Grow the residual hybridoma cells in T-75 flask for RNA production (freeze back three aliquot pellets)
17. Harvest SFM and purify mAb by chromatography (ii) Polyclonal Activation of Human B Cells with rh-IL-21, CD40L, BAFF-NIH3T3 Feeder Cells Materials 1. Subject sample
   a. PBMCs: 1×10$^6$ cells per plate
   b. Subject Tonsils/Adenoids: 1×10$^6$ cells per plate
2. Medium A (Stemcell Technologies, 03801)
3. Trypan blue (Gibco 15250-061)
4. CpG
   a. Order the oligonucleotide ZOEZOEZZZZZOE-EZOEZZZT (SEQ ID NO: 275) from invitrogen at the 10 mole scale (desalted)
   b. Dissolve in nuclease free water at a concentration of 2.5 mg/ml
   c. Aliquot and store at −20° C.
5. Irradiated rh-IL-21, CD40L, BAFF-NIH3T3 cell line
   a. rh-IL-21, CD40L, BAFF-NIH3T3 cells grown in Medium A are trypsinized, washed, and resuspended in Medium A
   b. Irradiate cells for 15-20 minutes using Cesium 137 irradiator
6. Filtered conditioned media from rh-IL-21, CD40L, BAFF-NIH3T3 cell line (containing rh-IL-21 and BAFF)
   a. Harvest supernatant of nearly confluent rh-IL-21, CD40L, BAFF-NIH3T3 cells grown in Medium A.
   b. Centrifuge supernatant at 2500 RPM to pellet cellular debris.
   c. Sterile filter supernatant through 0.22 μm filter and store at 4° C.
7. Goat anti-human Kappa unlabeled antibody (Southern Biotech; 1 mg/ml; Cat No: 2060-01)
8. Goat anti-human Lambda unlabeled antibody (Southern Biotech; 1 mg/ml; Cat No: 2070-01)
9. rh-IL-21, CD40L, BAFF-NIH3T3 growth media (prepares en+ough for one 96 well plate at 300 μl/well)
   a. Add cells to solution containing the following components:
      i. 20 ml of Medium A
      ii. 12 ml of rh-IL-21, CD40L, BAFF-NIH3T3 conditioned media
      iii. 20 μl CpG stock
      iv. 1 μl of Goat anti-human Kappa unlabeled antibody (1 mg/ml)
      v. 1 μl of Goat anti-human Lambda unlabeled antibody (1 mg/ml)
      vi. 5×10$^5$ irradiated rh-IL-21, CD40L, BAFF-NIH3T3 cells
         1. Add 250 μl of Pen/Strep/Glutamine (100×) and 250 μl of Amphotericin B (250 μg/ml) per plate of Tonsil/Adenoids
10. 96-well plates (Corning: 3997)
11. Matrix electronic Pipette 850 μl (Thermo Scientific 2014)
12. Matrix tips (Thermo Scientific 8042)
13. 500 ml Rapid Flow filter unit, 0.22 μm (Fisher 09-741-05)
14. Hyclone Pen/Strep/Glutamine solution (Thermo SV30082.01)
15. Amphotericin B; 250 μg/ml solution (Fisher MT-30-003-CF)

Protocol

1. When using a frozen stock of Subject PBMCs or Tonsils/Adenoids (TAs), thaw samples rapidly in 37° C. water bath. Remove stock from the water bath as soon as it has thawed. When using freshly isolated PBMCs or TAs, skip steps 1-3.
2. Drop wise, add 1 ml of warmed Medium A to the cells
3. Resuspend the cells in 10 ml warmed Medium A
4. Centrifuge the cell suspension at 1,100 RPM for 5 min
5. Discard the supernatant and resuspend cells in 1 ml warmed Medium A
6. Count cells and assess viability with trypan blue staining 7. Add the cells to rh-IL-21, CD40L, BAFF-NIH3T3 growth media and plate them out into a 96-well plate. One plate for every 1 million viable PBMCs. Using an electronic multichannel pipette, dispense 300 µl/well of mixture containing PBMCs/TAs into a 96-well plate
8. Incubate plates at 37° C. with 5% $CO_2$ for 7-8 days
   a. Monitor cells closely as different cells grow at different rates
   b. Fresh TAs grow much more readily than frozen PBMCs or PBMCs from Red Cross filters
9. Screen plates by ELISA (see the Standard Human IgE Fluorescent ELISA protocol) after 7-8 days of incubation; check plates daily for growth of B cells.
10. Wells that are determined by ELISA to be producing desired IgE antibodies then are used for electrical cytofusion with HMMA cells (see B-cell/HMMA fusion protocol).

(iii) Growth and Maintenance of HMMA 2.5 Cells

Materials

1. HMMA 2.5 cells
2. 50 ml conical tubes (Falcon 352070)
3. Medium A (Stemcell Technologies, 03801)
4. Canted-neck tissue culture flasks (Falcon)
   a. T-25 (Falcon 353109)
   b. T-75 (Falcon 353136)
   c. T-150 (Falcon 355001)
   d. T-225 (Falcon 353139)
5. Cell scraper (Falcon 353087) or (Techno Plastic Products 99003)

Protocol

1. If starting with a frozen stock of HMMA cells, thaw an aliquot of the cells rapidly at 37° C. Remove the stock from the water bath as soon as it has thawed
2. Gently transfer the cells to a 50 ml conical tube
3. Drop wise, add 1 ml of warmed Medium A to the cells
4. Resuspend the cells in 10 ml of warmed Medium A
5. Centrifuge the cells for 5 minutes at 1100 RPM in a swinging bucket centrifuge
6. Discard the supernatant
7. Resuspend the cells in 25-30 ml of warmed Medium A and transfer to a T-75 flask
8. Incubate at 37° C. with 5% $CO_2$
9. Split cells just before they become confluent and/or the medium starts to turn yellow
   a. Aspirate off the old media
   b. Add back fresh, warm Medium A
   c. Scrape the cells off the bottom of the flask
   d. Transfer the cells to a bigger flask, or split them amongst flasks of the same size
10. Split cells 3-5 days prior to performing fusions.
11. Cells should be about 80-90% confluent, and as close to 100% viable as possible, prior to harvesting for use in electrofusion. Do not replace culture medium less than 12 hours prior to fusion (iv) B-Cell/HMMA Fusion Materials 1. BTX cytofusion media [gram amounts are for 500 ml of cytofusion media]
   a. 300 mM Sorbitol (Fisher, #BP439-500) [27.3 g]
   b. 0.1 mM Calcium Acetate (Fisher, #AC21105-2500) [0.008 g or 8 mg]
   c. 0.5 mM Magnesium Acetate (Fisher, #AC42387-0050) [0.0536 g or 53.6 mg]
   d. 1.0 mg/ml BSA (Sigma, #A2153) [0.5 g]
   e. Filter sterilize and store at 4° C.
2. BTX cytofusion cuvettes (BTX620: 2 mm gap width; 400 µl)
3. Cytofusion device:
   a. BTX ECM 2001
   b. BTX cuvette holder (BTX Safety Stand, Model 630B)
4. 384-well cell culture plates (Nunc, #164688)
5. 50× HAT (Sigma, #H0262)
6. Medium A (Stemcell Technologies, #03801)
7. Medium E (Stemcell Technologies, #03805)
8. HAT media
   a. 400 ml Medium A
   b. 100 ml Medium E
   c. One vial 50× HAT
9. Matrix electronic Pipette 850 µl (Thermo Scientific 2014)
10. Matrix tips (Thermo Scientific 8042)
11. Histopaque-1077 (Sigma-Aldrich; REF: 10771-6X100ML)

Protocol

1. Perform Histopaque-1077 gradient on HMMAs as described in Isolation of Peripheral blood mononuclear cells from human blood protocol.
2. Count HMMA cells and resuspend them in warmed BTX cytofusion media at 5 million cells/ml. You will need 120 µl of $5×10^6$ cells/ml for each fusion; transfer them to a 1.5 ml microcentrifuge tube that contains 1 ml of warmed BTX cytofusion media; you may need several tubes depending on the desired number of fusions.
3. Gently resuspend the contents of an IgE positive B cell culture well (as determined by ELISA, see the Standard Human IgE Fluorescent ELISA protocol) and transfer them to a 1.5 ml microcentrifuge tube that contains 1 ml of warmed BTX cytofusion media.
4. Centrifuge the microcentrifuge tubes containing the HMMA cells and the microcentrifuge tubes containing the IgE positive B-cells (they remain in separate tubes at this point) at 3,000 RPM for 3 min in a tabletop centrifuge
5. Decant the supernatant
6. Resuspend the cell pellets in 1 ml of warmed BTX cytofusion media
7. Repeat the centrifugation, disposal of the supernatant, and resuspension of the pellet in cytofusion media two times (resulting in a total of 3 centrifugations). After the last centrifugation, DO NOT resuspend the pellot. Simply decant the supernatant and wait until step 9 to resuspend the cells
8. Resuspend the HMMA cell pellet in 1 ml of BTX cytofusion media (so that the concentration remains at 5 million cells/ml)
9. Use 120 µl of the HMMA cell solution at 5 million cells/ml to resuspend the positive B-cells in each microcentrifuge tube prior to transfer to a cytofusion cuvette
10. Transfer the mixture of HMMA and B-cells (volume approximately 200-250 µl) to a cytofusion cuvette
11. Place the cuvette(s) (device holds one or two cuvettes) into the cytofusion device, using a BTX cuvette holder. Run the program with the following settings:

a. Pre: 40 v×30 sec AC current
b. Pulse: 300 v×0.04 msec DC current
c. Post: 40 v×7 sec AC current
12. After the fusion, incubate the cuvettes at 37° C. with 5% $CO_2$ for 20-30 minutes
13. Add the contents of cuvettes to 20 ml of HAT medium.
14. Use an electronic Matrix pipette to plate the fusion products at 50 μl/well into a 384-well cell culture plate
15. Incubate the plates at 37° C. with 5% $CO_2$ for 13-15 days prior to screening hybridomas for antibody production (see the Standard Human IgE Fluorescent ELISA protocol)

(v) Subcloning of Hybridomas by Limiting Dilution

Materials

1. Medium E (Stemcell Technologies, #03805)
2. 384-well cell culture plates (Nunc, 164688)
3. 48-well cell culture plates (Corning Inc. 3548)
4. Matrix electronic pipette 850 μl (Thermo Scientific 2014)
5. Matrix tips (Thermo Scientific 8042)

Protocol

1. Enrichment dilution of the ELISA hits (option 1)
   a. Gently resuspend hits from a 384-well plate
   b. Place one drop of the cell suspension into a basin containing 21.5 ml of Medium E. Mix well
   c. Put the remainder of the cell suspension into one well of a 48-well plate containing 1 ml of Medium E
   d. Repeat for up to 5 hits; add the single drop of cells to the same basin and make individual cultures in the 48-well plate
   e. Plate 50 μl per well using an electronic Matrix pipette onto a 384-well plate
2. Enrichment dilution of the ELISA hits (option 2: a more stringent method of limiting dilution)
   a. Gently resuspend hits from a 384-well plate
   b. Place 1 μl of the cell suspension into a basin containing 20 ml of Medium E. Mix well
   c. Place 5 μl of the cell suspension into a separate basin containing 20 ml of Medium E. Mix well
   d. Place 10 μl of the cell suspension into a third basin containing 20 ml of Medium E. Mix well
   e. Plate the contents of each basin onto a separate 384-well plate at 50 μl per well
   f. Put the rest of the cell suspension into one well of a 48-well cell culture plate containing 750 μl of Medium E
3. Incubate the plates for 13-15 days at 37° C. with 5% $CO_2$, then recheck the 48-well plate and 384-well plates by ELISA
4. If no hits are found on the 384-well plate, repeat the enrichment dilution and plating of a 384-well plate if one or more of the 48-well cultures are active (vi) Subcloning Hybridomas by Flow Cytometry Materials 1. Medium E (Stemcell Technologies, #03805)
2. Flow cytometry tubes (Falcon 352235)
3. 48-well cell culture plates (Corning Inc. 3548)
4. 384-well cell culture plates (Nunc, 164688)
5. Hybridoma culture growing in a 384-well plate
6. Propidium iodide (Molecular Probes P-3566)

Protocol

1. Gently resuspend a hit from a 48-well plate and place into a flow tube containing 1 ml of Medium E
2. Dispense 50 μl/well of Medium E onto on 384-well plate per hybridoma
3. Add 1 μl of propidium iodide to each tube of hybridomas
4. The flow core staff will process the samples, sorting 1 viable cell per well into 384-well plate
5. Incubate the plates at 37° C. with 5% $CO_2$ for 13-15 days
6. Screen the plates by ELISA or functional assay
7. If no hits are found on the 384-well plate, repeat the limiting dilution and plating of the 48-well culture hits or thaw frozen aliquot of that hybridoma line and repeat cloning procedure (vii) Thawing Hybridomas by Limiting Dilution Cloning Materials 1. 50 ml conical tubes (Falcon, 352070)
2. Medium A (Stemcell Technologies, #03801)
3. 384-well cell culture plates (Nunc, 164688)
4. Matrix electronic Pipette 850 μl (Thermo Scientific 2014)
5. Matrix tips (Thermo Scientific 8042)

Protocol

1. Thaw an aliquot of the cells rapidly at 37° C. Remove stock from the water bath as soon as it has thawed
2. Drop wise, add 1 ml of warmed Medium A to the cells then gently transfer the cells to a 50 ml conical tube containing 10 ml of warmed Medium A
3. Centrifuge the cells for 5 minutes at 1100 RPM in a swinging bucket centrifuge
4. Discard the supernatant
5. Resuspend the cell pellet in 900 μl of Medium A
6. Prepare 5 different basins each containing 20 ml of Medium E
7. Into the 5 basins place 1 μl, 5 μl, 25 μl, 100 μl, and the remainder of the washed cells (one for each basin)
5. Plate the contents of each basin onto a separate plate at 50 μl per well using an electronic Matrix pipette (viii) Expanding Hybridomas Materials 1. 12 well cell culture plates (Falcon 353043)
2. Medium E (Stemcell Technologies, #03805)
3. T-75 Flasks (Falcon 353136)
4. T-225 Flasks (Falcon 353139)
5. Hybridoma Serum Free Media (Gibco 12045)
6. DMSO (Sigma D2650)
7. Cryovial tubes (Sarstedt 72.694.996)
8. Cell scrapers (Falcon 353087) or (Techno Plastic Products 99003)

Protocol

1. Grow hybridoma culture in a 48-well plate in an incubator at 37° C. with 5% $CO_2$ until cells are 25% confluent
2. Check antibody production by ELISA (see the Standard Human IgE Fluorescent ELISA protocol)
3. Gently resuspend cells, and take an aliquot of cells for freezing (see the Freezing cells protocol)
4. Transfer the remainder of the cells to a 12 well plate containing 2 ml of Medium E 5. Grow 12 well plates in an incubator at 37° C. with 5% $CO_2$ until cells are 25% confluent
6. Check antibody production by ELISA (see Standard Human IgE Fluorescent ELISA protocol)
7. Freeze back an aliquot that represents 25% of the culture (see Freezing cells protocol)
8. Transfer the remainder of the cells in the 12 well plate to a T-75 flask and add Medium E to 30 ml
9. Every 3-5 days, feed the cells by aspirating off the old media and adding back fresh, warm media. Feed the cells every 3-5 days until the cells are 80% confluent
10. Mark 250 ml on four Corning T-225 flasks
11. Scrape cells off of the bottom of the T-75 flask using a cell scraper
12. Add the cell suspension to 1 L of Serum Free Media and divide equally to each of the four T-225 flasks
13. Freeze back an aliquot of the cells (see the Freezing cells protocol)
14. Add 30 ml of Medium E to the cells which remain in the T-75 Flask
15. Grow hybridomas in an incubator at 37° C. with 5% $CO_2$ in T-225 flasks for mAb production (see the chromatographic purification of full-length antibodies protocol) and T-75 flasks for RNA production
16. Freeze back 3 aliquot pellets of cells from the T-75 flasks for RNA production (see the Freezing cells protocol)
17. Grow the hybridomas in an incubator at 37° C. with 5% $CO_2$ in the T-225 flasks until cells are <10% viable using visual inspection
18. Harvest the medium for antibody purification by first centrifuging medium for 10 min at 2500 RPM followed by sterile filtration via 0.22 μm filter. Before purifying, perform an ELISA on the supernatant (ix) Freezing Hybridoma Cells Materials 1. Freezing Media
   a. 90% FBS (Sigma F-2442) or Medium E (Stemcell Technologies, #03805)
   b. 10% DMSO (Sigma D2650)
   c. Filter sterilize
2. 0.45 μm filter (Nalgene 167-0045)
3. Sarstedt cryovial tubes (Sarstedt 72.694.996)
4. Mr. Frosty freezing controlled freezing chamber Protocol 1. Label cryovials
2. Gently pipette the culture to resuspend any cells that have adhered to the bottom. When aspirating the cells, make sure to pipette up and down multiple times in a clockwise fashion around the side of the well, to ensure you really get the cells (even after doing this a few times, there are still some cells in the wells
3. Transfer cells to a cryovial tube and centrifuge in a tabletop centrifuge at 3000 RPM for 5 minutes
4. Discard supernatant and
   a. Option 1: slowly resuspend cells using 1 ml of freezing media
   b. Option 2: resuspend cells in 900 μl of FBS or Medium E and then slowly add 100 μl of DMSO
5. Place in a Mr. Frosty and put in the −80° C. freezer for at least 100 minutes (1 degree cooling per minute)
6. Store in liquid nitrogen (x) Isolation of Peripheral Blood Mononuclear Cells from Human Blood Materials 1. Na heparin green top blood collection tubes (BD Vacutainer 367874)
2. Serum red top blood collection tubes with clot activator (BD Vacutainer 367820)
3. 1× Sterile D-PBS (cellgro, 21-031-CM)
4. 50 ml conical tubes (Falcon, 352070)
5. Ficoll 1077 (Sigma 10771, Histopaque-1077)
6. Medium A (Stemcell Technologies, 03801)
7. Trypan blue (Gibco 15250-061)
8. DMSO (Sigma D2650)
9. Sarstedt cryovial tubes (Sarstedt 72.694.996)
10. Mr. Frosty controlled freezing chambers Protocol 1. Obtain peripheral blood from the subject by venipuncture. Have blood drawn into a Na heparin green top tube. If desired, have another aliquot drawn into a red top tube in order to freeze away an aliquot of subject sera (you may also save subject plasma in step 6). The approximate yield of peripheral blood mononuclear cells (PBMCs) is 1-2E6 cells/ml of peripheral blood
2. Add 15 ml of warmed 1× D-PBS to a 50 ml conical tube. One conical tube is needed for every 10 ml of blood drawn
3. Add 10 ml of blood to each 50 ml conical tube containing 1× D-PBS
4. Underlay the 25 ml of blood and D-PBS with 14 ml of warmed Ficoll
5. Centrifuge in a swinging bucket centrifuge for 25 minutes at 2500 RPM, with the brake and acceleration set to zero, or as low as possible
6. Remove and discard most of the plasma on top, down to about 2-3 mm from the buffy layer. Save 1 ml for testing, if desired (freeze plasma at −80° C.). Alternatively, blood can be collected into a red top tube
7. Remove buffy coat by tilting tube and removing cells until middle of liquid in tube starts to clear then pipette the material into a new 50 ml conical tube. Be sure to move the pipette around the sides of the tube in order to collect all PBMCs.
8. Add up to 50 ml of warmed Medium A to tube containing buffy coat layers
9. Centrifuge at 1800 rpm for 18 min in a swinging bucket centrifuge
10. Remove supernatant and resuspend cells in 2 ml of warmed Medium A for every initial 10 ml of blood
11. Add 10 μl of cells to 390 μl of trypan blue and count 2 quadrants
12. When continuing on to perform B cell cultures from the PBMCs without freezing see the B-cells from subject PBMCs protocol
13. For freezing PBMCs, resuspend cells at 5-10E6 cells per 900 μl in Medium A, then add ⅒ final volume of DMSO 14. Freeze PBMCs in 1 ml aliquots in Cryovial tubes.
15. Place tubes in a Mr. Frosty freezing chamber and put in the −80° C. freezer for at least 100 minutes (1 degree cooling per minute)
16. Move samples to liquid nitrogen for storage (xi) Standard Human IgE Fluorescent ELISA Materials 1. Capture antibodies:
   Omalizumab (Xolair); 2.0 mg/ml
2. Secondary antibody
   Mouse anti-human IgE FC-HRP; Clone B3102E8-HRP; Southern Biotech; Cat No: 9160-05
3. Carbonate buffer
   Dissolve the following in 1 L of distilled water:
   i. 1.59 g $Na_2CO_3$
   ii. 2.93 g NaHCO
   iii. Adjust pH to 9.6
   iv. Filter solution at 0.22 μm
   v. Store at room temperature
4. 384 well; black, w/o lid; non-treated, non-sterile; Thermo Scientific No. 262260
5. ELx405 Plate Washer (Biotek)
6. Matrix Pipette (Thermo)
7. 64-channel multipipette (CappAero C10-64) or standard 12 channel pipette
8. QuantaBlu Fluorogenic Peroxidase Substrate Kits; Thermo Prod #15169
   QuantaBlu Substrate Solution, 250 ml
   QuantaBlu Stable Peroxide Solution, 30 ml
   QuantaBlu Stable Stop Solution, 275 ml
9. PBS 10× Molecular Biology Grade; Cellgro REF 46-013CM
10. Block (1 L)
    100 ml of 10× PBS Molecular Biology Grade (Cellgro REF 46-013-CM)
    12-15 g of powdered milk (Great Value Instant Nonfat Dry Milk from Walmart)
    20 ml goat serum (Gibco 16210-072)
    Fill up to 1 L with $dH_2O$
    Add 500 μl of Tween 20 (Sigma P7949)
    Store at 4° C.
11. 1× Wash buffer (1 L)
    100 ml of 10× PBS Molecular Biology Grade (Cellgro REF 46-013-CM)
    1 ml of Tween 20 (Sigma P7949)
    900 ml water
    Store at room temperature
12. Medium A (Stemcell Technologies, 03801)
13. Molecular Devices Spectramax M3 (or equivalent fluorescence plate reader)

Protocol

1. Dilute capture antibody in carbonate buffer for the number of plates you want to coat (make 10.5 ml per plate; there will be extra).
   a. Omalizumab (2 mg/ml); 1:1000
2. Coat plates overnight at 4° C.:
   a. Use 25 μl/well for a 384-well plate (10.5 ml)
   b. Note: If you forget to coat plates overnight, you can coat plates the same day at 37° C. for 3 hours
3. Wash each plate(s) 5 times with 1× wash buffer (or water) by running program 8 (384-5) on the 405.
   a. Alternatively, you can simply dump the contents into the sink and tap the surface of the ELISA plate on paper towels
4. Fill all wells with block:
   a. Use 115 μl/well for a 384-well plate (49 ml)
   b. Incubate at room temperature for at least 1 hour
      i. Don't shortcut this step
      ii. Block entire plate even if you aren't using every well
      iii. Start block first thing in the morning after the wash step
   c. Wash each plate(s) 5 times with 1× wash buffer (or water) by running program 8 (384-5) on the 405.
   d. Add block to all wells:
      i. Use 25 μl/well for a 384 well plate (10.5 ml)
5. Transfer 25 to 75 μl of rh-IL-21, CD40L, BAFF-NIH3T3 B-cell or hybridoma supernatant using a 12 channel pipette (if source pate is 96-well) or 64-channel multipipette (if source plate is 384-well)
   a. Perform this step in the laminar flow hood.
   b. Be careful not to suck up the rh-IL-21, CD40L, BAFF-NIH3T3 or B-cells using the pipette (don't pull supernatant when in contact with the bottom of the well)
6. Incubate plates for at least 30 minutes and up to one hour
   a. Always be sure to incubate the supernatants longer than the incubation time used for the secondary antibody
7. Wash each plate(s) 5 times with 1× wash buffer (or water) by running program 8 (384-5) on the 405.
8. Dilute the secondary antibody in block solution:
   a. Mouse anti-human IgE FC-HRP; Clone B3102E8-HRP
      i. Use 1:1000 dilution in block (1 μg/ml final)
      ii. Add 25 μl/well for 384 well plate (10.5 ml)
      iii. Add 100 μl/well for 96 well plate (10.5 ml)
   b. Incubate for 30 minutes at room temperature
      i. Note: Secondary antibodies conjugated to HRP are extremely difficult to get rid of
         1. Discard reservoir and tips that have come into contact with 2° HRP
9. Wash each plate(s) 7 times with 1× wash buffer by running program 9 (384-7) on the 405. Flip plate to opposite orientation and repeat for another 7 washes with 1× wash buffer.
10. Prepare fresh QuantaBlu Working Solution (WS) (WS is stable for 24 hrs at room temperature)
    a. Mix 9 parts of QuantaBlu Substrate Solution to 1 part of QuantaBlue Stable Peroxide Solution. Note: To reduce variability, equilibriate WS to RT before adding to the wells
    b. Prepare 10.5 ml of WS per plate:
       i. Add 9.45 ml QuantaBlu Substrate
       ii. Add 1.05 ml of QuantaBlu Stable Peroxide Solution
11. Add QuantaBlu Working Solution (WS) to each well and incubate at room temperature for 20-30 minutes
    a. Add 25 μl/well for 384 well plate (10.5 ml)
    b. Add 100 μl/well for 96 well plate (10.5 ml)
12. Stop peroxidase activity by adding 50 μl of QuantaBlu Stop Solution to each well
    a. Add 25 μl/well for 384 well plate (10.5 ml)
    b. Add 100 μl/well for 96 well plate (10.5 ml)

13. Measure relative fluorescence units (RFU) of each well with Molecular Devices Spectramax M3 (or equivalent fluorescence plate reader)
    a. The excitation and emission maxima for QuantaBlu Substrate are 325 nm and 420 nm respectively.
    b. Select Corning 384 well plate black as plate type
14. Transfer positive wells from the original culture plate to:
    a. If you were screening rh-IL-21, CD40L, BAFF-NIH3T3 activated B-cells, gently resuspend the positives cells and transfer each hit to microcentrafuge tube to prepare for cytofusion (see B-cell/HMMA fusion protocol)
    b. If you were screening hybridomas, transfer each hit to the next biggest well or flask containing Medium E (the order is 384-well plates to 48-well plates to 12-well plates to a T-75 flask to a T-225 flask)

III. ACTIVE/PASSIVE IMMUNIZATION AND TREATMENT/PREVENTION OF ALLERGIC DISEASE

A. Formulation and Administration

The present disclosure provides pharmaceutical compositions comprising engineered IgG antibodies and for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, or delivered by mechanical ventilation.

Active vaccines are also envisioned where antibodies like those disclosed are produced in vivo in a subject at risk of parasitic worm infections. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, or by nebulizer. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

IV. ANTIBODY CONJUGATES

Antibodies of the present disclosure may be linked to at least one agent to from an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase. Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as SNCl$_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Another type of antibody conjugates contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939,350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting antigens, such as allergy-related antigens and Helminth antigens.

Some immunodetection methods include enzyme linked immunosorbent assay (ELISA), radioimmunoas say (RIA), immunoradiometric assay, fluoroimmunoassay, chemiluminescent assay, bioluminescent assay, and Western blot to mention a few. In particular, a competitive assay for the detection and quantitation of antibodies directed to specific epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing parasitic worms or allergens, and contacting the sample with a first antibody in accordance with the present disclosure, as the case may be, under conditions effective to allow the formation of immunocomplexes.

These methods include methods for purifying allergens or parasitic worm antigens from a sample. The antibody will preferably be linked to a solid support, such as in the form of a column matrix, and the sample suspected of containing the allergen or antigen will be applied to the immobilized antibody. The unwanted components will be washed from the column, leaving the allergen antigen immunocomplexed to the immobilized antibody, which is then collected by removing the allergen or antigen from the column.

The immunobinding methods also include methods for detecting and quantifying the amount of allergen or antigen in a sample and the detection and quantification of any immune complexes formed during the binding process. Here, one would obtain a sample suspected of containing allergen or antigen, and contact the sample with an antibody that binds the allergen or antigen, followed by detecting and quantifying the amount of immune complexes formed under the specific conditions. In terms of antigen detection, the biological sample analyzed may be any sample that is suspected of containing allergen or antiben, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to allergen or antigen present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (RIA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the allergen antigen is added to the wells. After binding and washing to remove non-specifically bound immune complexes, the bound antigen may be detected. Detection may be achieved by the addition of another anti-allergen/antigen antibody that is linked to a detectable label. This type of ELISA is a simple "sandwich ELISA." Detection may also be achieved by the addition of a second anti-allergen/antigen antibody, followed by the addition of a third antibody that has binding affinity for the second antibody, with the third antibody being linked to a detectable label.

In another exemplary ELISA, the samples suspected of containing the allergen or antigen are immobilized onto the well surface and then contacted with the anti-allergen/antigen antibodies of the disclosure. After binding and washing to remove non-specifically bound immune complexes, the bound anti-allergen/antigen antibodies are detected. Where the initial anti-allergen/antigen antibodies are linked to a detectable label, the immune complexes may be detected directly. Again, the immune complexes may be detected using a second antibody that has binding affinity for the first anti-allergen/antigen antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of anti-parasitic worm or anti-allergen antibodies in sample. In competition based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventors propose the use of labeled anti-parasitic worm or anti-allergen antibodies to determine the amount of anti-parasitic worm or anti-allergen antibodies in a sample. The basic format would include contacting a known amount of anti-parasitic worm or anti-allergen monoclonal antibody (linked to a detectable label) with parasitic worm antigen or allergen. The antigen or allergen is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins in a given sample of tissue homogenate or extract. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that bacteria, virus or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF, but are far more fragile and do not stand up well to repeated probing. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors, and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

D. Immunodetection Kits

In still further embodiments, the present disclosure concerns immunodetection kits for use with the immunodetection methods described above. As the antibodies may be used to detect Allergy or helminth antigens, or antibodies binding thereto, may be included in the kit. The immunodetection kits will thus comprise, in suitable container means, a first antibody that binds to an antigen, and optionally an immunodetection reagent.

In certain embodiments, the antibody may be pre-bound to a solid support, such as a column matrix and/or well of a microtitre plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

E. Vaccine and Antigen Quality Control Assays

The present disclosure also contemplates the use of antibodies and antibody fragments as described herein for use in assessing the antigenic integrity of an antigen in a sample. Biological medicinal products like vaccines differ from chemical drugs in that they cannot normally be characterized molecularly; antibodies are large molecules of significant complexity, and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns, but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and there is great pressure on manufacturers, regulatory authorities, and the wider medical community to ensure that products continue to meet the highest standards of quality attainable.

Thus, one may obtain an antigen or vaccine from any source or at any point during a manufacturing process. The quality control processes may therefore begin with preparing a sample for an immunoassay that identifies binding of an antibody or fragment disclosed herein to a viral antigen. Such immunoassays are disclosed elsewhere in this document, and any of these may be used to assess the structural/antigenic integrity of the antigen. Standards for finding the sample to contain acceptable amounts of antigenically intact antigen may be established by regulatory agencies.

Another important embodiment where antigen integrity is assessed is in determining shelf-life and storage stability. Most medicines, including vaccines, can deteriorate over time. Therefore, it is critical to determine whether, over time, the degree to which an antigen, such as in a vaccine, degrades or destabilizes such that is it no longer antigenic and/or capable of generating an immune response when administered to a subject. Again, standards for finding the sample to contain acceptable amounts of antigenically intact antigen may be established by regulatory agencies.

In certain embodiments, viral antigens may contain more than one protective epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen. By examining the integrity of multiple epitopes, a more complete picture of the antigen's overall integrity, and hence ability to generate a protective immune response, may be determined.

VI. EXAMPLES

The following examples are included to demonstrate preferred embodiments. It should be appreciated by those of skill in the art that the techniques disclosed in the examples that follow represent techniques discovered by the inventors to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Generation of naturally occurring human IgE mAbs. Historically it has been easy to make murine mAbs using hybridoma technologies, but extremely difficult to make hybridomas to selected targets using human peripheral blood cells. The inventors' lab has worked diligently on improving the efficiency and versatility of human hybridoma generation for use as a tool to dissect the humoral immune response following natural infection or vaccination. They have generated hundreds of naturally-occurring human mAbs using hybridoma technologies (48-51). These advances resulted in the ability to move this technology to a different field and successfully generate for the very first time natural human allergen and helminth-specific IgE mAbs.

Aside from technological innovations in electrical cytofusion protocols that have allowed us to make hundreds of human IgG secreting hybridomas, several specific advancements have been made which permit us to now accomplish the Aims in this proposal (see FIG. 1). First, and most importantly, the inventors are able to expand IgE encoding B cells in primary culture. This has been achieved through the use of the NIH3T3 fibroblast line genetically engineered to constitutively express cell-surface human CD154 (CD40 ligand), secreted human B cell activating factor (BAFF) and human IL-21 (provided by Dr. Deepta Bhattacharya; Washington University, St. Louis). This is required as IgE encoding memory B cells do not expand sufficiently using Epstein Barr Virus (EBV) transformation. Helminth-infected patient PBMCs are grown in the presence of gamma-irradiated NIH3T3 fibroblasts and their B cell receptors are globally cross-linked with a mixture of murine anti-human light chain mAbs. The kinetics and efficiency of human B cell activation and expansion is improved with TLR9 stimulation by CpG oligodeoxynucleotides. The second breakthrough that makes it possible to generate human IgE mAbs is having the ability to accurately detect B cells secreting IgE in primary culture (ng/mL concentrations).

Identification of wells containing IgE is achieved by using a mAb sandwich ELISA, where both capture and detection mAbs are human IgE-specific. Using commercially available mAbs, and those provided by Robert Hamilton (Johns Hopkins University School of Medicine), the inventors tried dozens of sandwich ELISA iterations before settling on one with both exceptional sensitivity and specificity. Adequate sensitivity is only achieved by using a secondary antibody conjugated to horseradish peroxidase (HRP) and a fluorescent substrate offered by Pierce Biotechnology. Finally, with this robust technique in place, the inventors are able to begin to dissect the human antibody response to helminth infection. In these initial experiments, the inventors have generated the first naturally occurring human helminth specific IgE secreting hybridomas and began characterizing these in detail.

Characterization of the human IgE memory B cell response. The estimated minimum circulating memory B cell frequencies can be determined using the data obtained by primary culture screening (see Table 1). Because of the reasons noted previously, to the inventors' knowledge, no one has been able to successfully grow, expand and detect IgE memory B cells in primary culture. Therefore, information regarding the frequencies of this population of cells, and how they relate to the total and specific IgE concentrations in the serum, is needed. This will shed a tremendous amount of light on this very important but difficult to study IgE memory B cell population. This information can also be used to estimate the hybridoma yield from a particular subject and to make comparisons between subjects.

Identification and characterization of rare helminth-specific human IgE mAbs. PBMCs obtained from helminth-infected subjects are be the starting material used in primary cultures. These cultures will initially be screened to identify memory B cells secreting IgE antibody. The inventors will then screen the IgE positive cultures for reactivity to specific helminth proteins or concentrated helminth lysate. The goal is to avoid bias towards any given helminth protein specificity, and thus care will be taken to avoid focusing on the strongest reacting cultures. Since helminth lysate contains many proteins, each having a different concentration, there are differences in the sensitivity to detect different antigen-specific IgE mAbs, resulting in a range of relative fluorescence units (RFU). Therefore, this secondary screening assay will be interpreted as positive or negative and not quantitative. For example, two of the purified IgE mAbs bind lysate in direct ELISA with very different maximum binding intensities (likely due to differences in the concentration of their target proteins).

Figure 2:
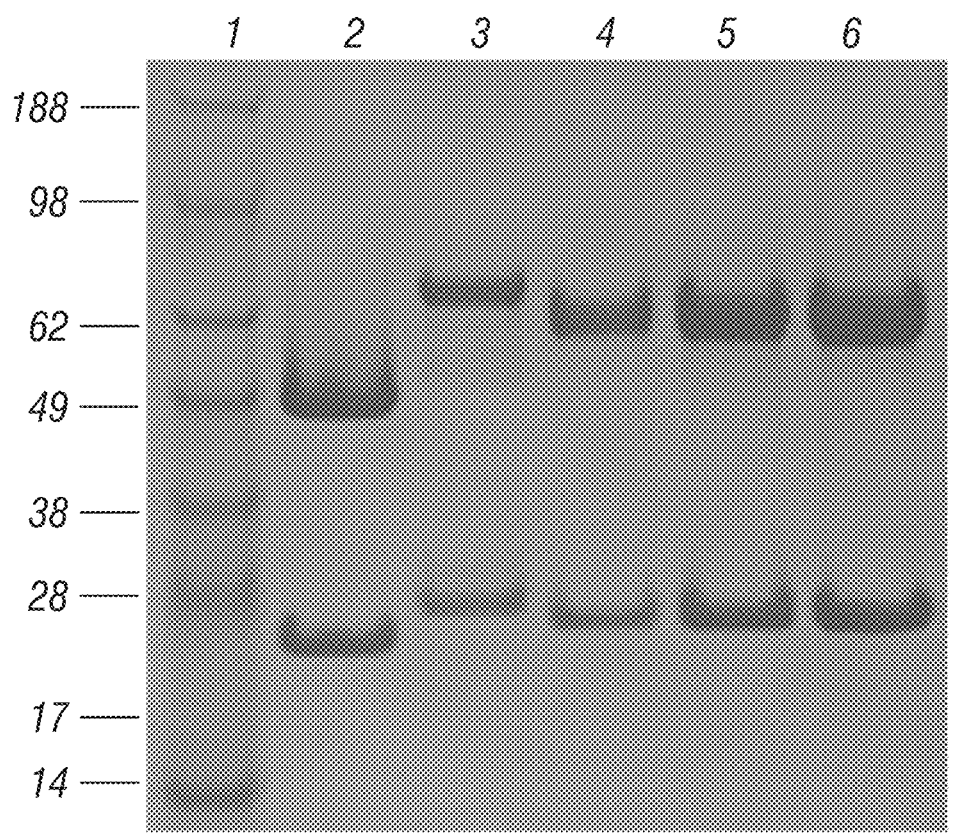

At the same concentration, human mAb 7G12 binds with an RFU of 40,000, while 11H12 binds at only ten times background, about 1,000 RFU. The inventors plan to massively expand their initial panels of helminth-specific IgE mAbs, generating and purifying (see FIG. 2) at least one hundred mAbs against both *Wuchereria bancrofti* and *Strongyloides stercoralis*. Fortunately, the inventors have in place a cheap, reliable, and reusable chromatography method to purify IgE mAb from serum free medium to nearly 100% purity.

Identification of the helminth protein targets of human IgE mAbs. The protein targets of purified IgE mAbs will be identified if they do not bind the inventors' panel of recombinant helminth proteins, generated and characterized previously. First, the inventors will test each antibody for protein binding in Western blot analysis. Western blotting will be performed using concentrated helminth lysate. This will provide a tremendous amount of information about the protein target of the mAbs if binding is detected. However, the lack of binding in Western blot does not imply that the mAb does not target a helminth protein. More likely, since they bind lysate in ELISA, this means that the mAb requires a protein in its native form, which is often absent given the conditions used for SDS-PAGE, even without reducing agent.

Figure 3B:
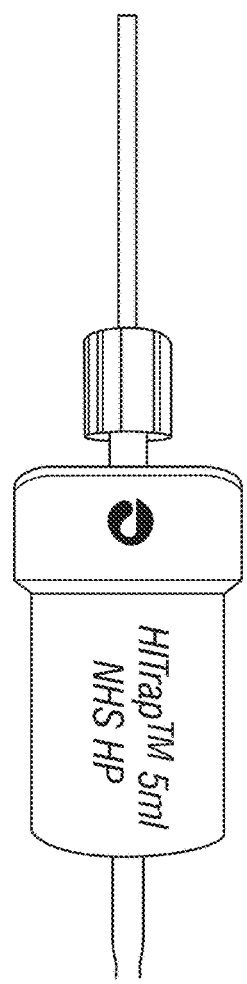

Having a purified mAb creates a unique situation, given the high affinity of this interaction, in which the target can be identified using immunoprecipitation. The inventors have developed anti-IgE chromatography columns that are principally use for IgE mAb purification. This technology can be used to capture the IgE mAb and immunopurify the target protein from helminth lysate. Mass spectroscopy is then used to identify the specific helminth protein target present in the eluent (see FIGS. 3A-B). Fortunately, many of the most clinically important helminths genomes and transcriptomes have been published.

Once it is identified, there are two strategies to produce helminth protein needed for all of the studies to follow. The target protein can either be purified from extract using immunoaffinity purification, using the helminth IgE coupled to columns or the genomic sequence can be cloned and expressed to make recombinant protein. Each of these methods has its advantages and disadvantages. The inventors have used anti-IgE mAb Healthcare NHS activated HiTRAP chromatography columns. These columns are very effective, easy to use, and inexpensive. The inventors have purified over fifty IgE mAbs using one of the inventors' anti-IgE mAb Omalizumab columns without any loss in yield (recently purifying 30 mg of mAb 10H9 shown in FIG. 1). This strategy will produce native helminth protein, but will require production of large amounts of helminth lysate to use as starting material (this same material is used multiple times with different mAbs). A second method to make large amounts of helminth protein will take advantage of the genomic sequence data that is now available. The advantage of this method is that large amounts of recombinant protein can be expressed in bacteria and purified using polyhistidine-tag technology. Vary large quantities of recombinant protein can be made easily using this strategy. However, there is always the possibility that the protein will not achieve the native structure required for a particular IgE mAb epitope.

Mapping the antigenic sites of novel human helminth-specific IgE mAbs. A very important concept at the heart of effector cell mediator release is the antigenic site (a non-overlapping antigenic region). In order for cross-linking of Fcε receptors to occur with native monovalent proteins, two different IgE antibodies must bind simultaneously—this is not the case for some multivalent proteins. This implies that the two antibodies must be directed toward different antigenic sites. Antigenic sites can be easily defined using antibody competition assays. The inventors have developed quantitative competition assays using biolayer interferometry. This is a label-free technology for measuring biomolecular interactions in real-time. Purified helminth protein and human IgE will be used to assign antigenic groups to each of the mAbs in a panel directed toward a particular helminth protein target.

The kinetics of antibody binding to helminth proteins are also of great interest, as antibodies with higher affinities could possess more functional potency. Biosensor technology will be used to assess binding at the biochemical level (kon, koff, KD). The inventors have found that by capturing purified biotinylated IgE mAb to avidin biosensors and using purified helminth protein in solution, the inventors can avoid issues with avidity. An alternative strategy if this fails is to bind purified helminth protein to the biosensor tip and use helminth-specific FAb in solution.

Assess the cross-reactivity of helminth-specific human IgE mAbs for allergens. The inventors will use Phadia technology to determine if there is cross-reactivity of the IgE mAbs with clinically important allergens. This technology is principally used to assay patient serum to assist clinicians with diagnoses and treatment of allergic diseases. Using multiplexing chip technology (ISAC), the inventors will assess IgE mAb binding to 112 of the most common and clinically relevant allergen protein components. Several studies have suggested that cross-reactive IgE antibodies may exist, connecting allergic disease with immunity to helminth infection.

The most notable are protein homologs found in dust mites and parasitic worms. This will allow both for very broad unbiased cross-reactivity surveys of the natural helminth specific IgE immune response, and more targeted homologous allergen protein screens based off sequence data. If helminth-specific IgE mAbs are found to react strongly to an allergen protein, the inventors will further study this in several ways. First, they will investigate sequence and functional homology, if this is known, using the information obtained by identifying the helminth protein target. Next, they will employ biosensor technology to characterize the affinity of the IgE mAb interaction with the cross-reacting allergen, so that it can be compared to that of its native target interaction. Lastly, they will test whether there is evidence of functional activity using basophil mediator release assay with the helminth-specific IgE mAb and the cross-reacting allergen protein.

Testing functional activity of helminth-specific human IgE mAbs. IgE mAbs, found to target the same helminth protein but fall into different competition groups, or those that bind multivalent proteins, will be studied for functional activity using a primary human basophil cell mediator release assay. Graded dose response curves can be created and half maximal effective concentration (EC$_{50}$) calculated. Inhibition of mediator release will be used to assess the ability of isotype switch variant IgG4 mAbs to antagonize this process using helminth infected patient serum and purified helminth proteins. Half-maximal inhibitory concentration (IC$_{50}$) can be calculated and used to compare functional potency of each mAb. This will allow the inventor to determine the molecular basis (differences in affinity, protein specificity, epitope availability, etc.) for variation in functional activity of human IgE mAbs and their target helminth proteins.

Identification and characterization of rare allergen-specific human IgE mAbs. PBMCs obtained from allergic subjects where grown in primary cultures as described above. These cultures were screened to identify memory B cells secreting IgE antibody. Cells were immortalized using electrical cytofusion with myeloma partner and hybridomas selected for in HAT medium. Purified IgE mAb was then used to determine target antigen specificity. As shown in Table 7, human IgE mAbs were generated with specificity to important human foods and aeroallergens, such as: peanut, cashew, walnut, dust mite, cat, and *Aspergillus fumigatus*. These mAbs were found to target the most important food and aeroallergen proteins that cause allergic disease in humans. Key peanut proteins (Ara h 2, Ara h 6), their homologues in walnut and cashew (Jug r 1, Ana o 3) and important aeroallergen proteins for cat (Fel d 1), dust mite (Der p 1, Der p 2), and *Aspergillus fumigatus* (Asp f 1). These proteins were further characterized in in vivo functional assays, as demonstrated below, to determine their ability to incite effector cell mediator release and ultimately cause anaphylactic shock in mice.

Testing functional activity of human anti-allergen IgE mAbs by anaphylaxis. Human FcεRI transgenic mice B6.Cg-Fcεr1a$^{tm1Knt}$ Tg(FCER1A) 1Bhk/J were purchased from The Jackson Laboratory (stock #010506), brought out of cryogenic storage, bred and genotyped. These double mutant mice express the human Fc fragment of IgE, high affinity I, receptor for alpha polypeptide, (FCER1A), under the control of the human FCER1A promoter and carry the FcεR1a$^{tm1Knt}$ targeted mutation. Mice that are hemizygous for the transgene and homozygous for the targeted deletion of the mouse FcεRI respond to experimental induction of anaphylaxis with human IgE.

Figure 5:
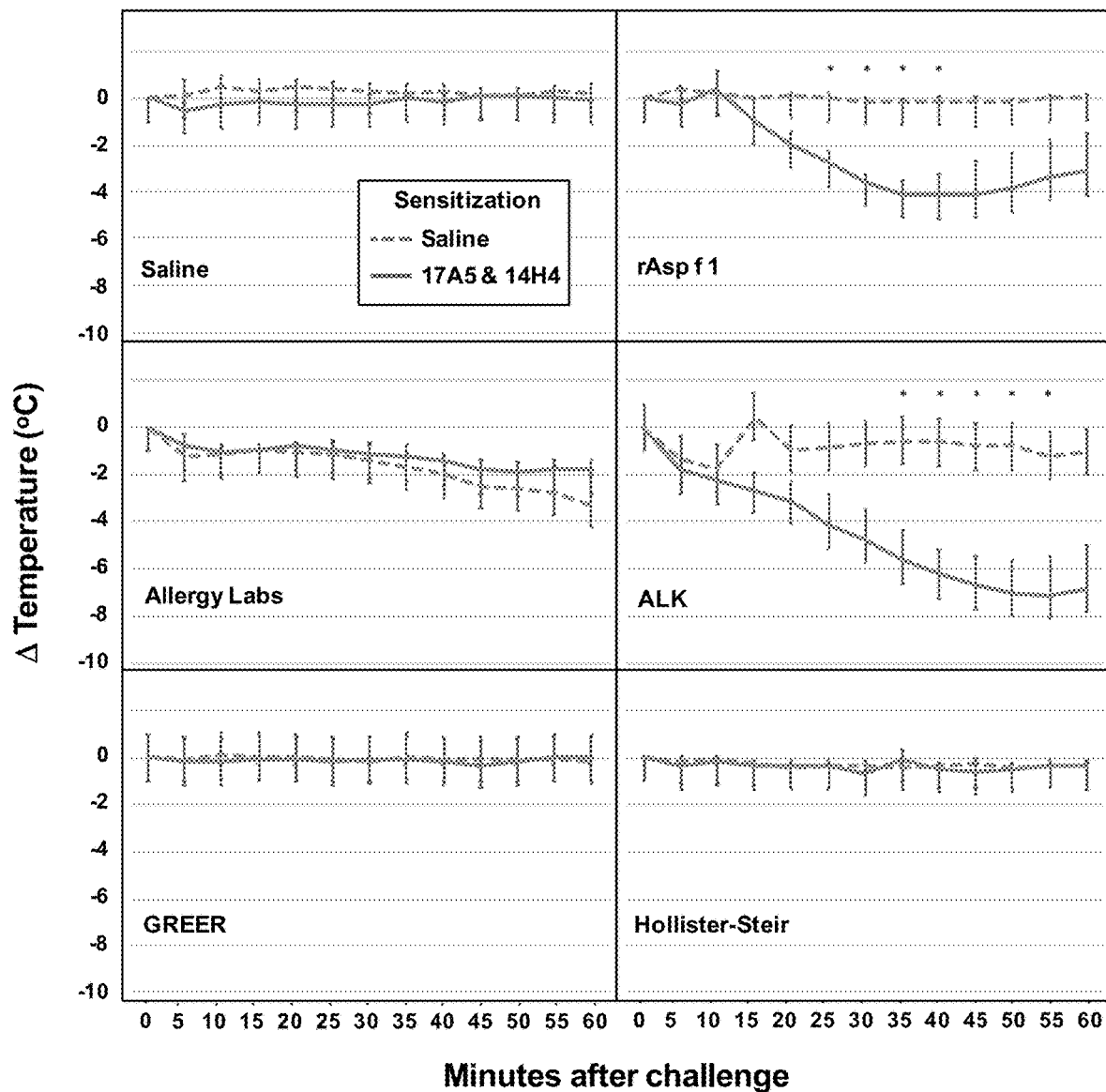

Transgenic mouse lines expressing FcεRIα were sensitized by IP injection of 100 µg total human anti-allergen protein IgE mAbs. Mice were challenged 72 h later by IP injection with predetermined maximal tolerated doses of allergen extract and the change in temperature from baseline was monitored using implanted temperature probes. As can be seen in FIG. 5, mice receiving challenge with purified Asp f 1, or ALK extract, underwent anaphylaxis as indicated in a drop in body temperature. Animals challenged with other manufacturer's extracts, found to contain no Asp f 1, did not induce anaphylaxis when sensitized with human anti-Asp f 1 monoclonal IgE antibodies.

To test the disease inciting ability of these human anti-peanut allergen specific IgE monoclonal antibodies, the inventor sensitized mice with either 100 µg total of Ara h 2-specific or 100 µg total of Ara h 6-specific IgE mAbs as shown in FIG. 6. Mice receiving functional antibody pairings, that is two human IgE mAbs which target different epitopes on the same allergen protein, underwent severe anaphylactic shock, culminating in death. Thus, these human peanut-specific IgE mAbs are so potent at inducing anaphylaxis in this mouse model that the inventor is unable to measure temperature drop in many cases due to the rapid death of the animal. Some animals begin having seizure and die within 10 min of the challenge dose.

TABLE A

NUCLEOTIDE SEQUENCES FOR IgE ANTIBODY VARIABLE REGIONS

| Clone | Variable Sequence Region | SEQ ID NO: |
|---|---|---|
| 1H9 heavy | GAATTCCAGTTGGTGCAATCTGGGTCTGAGTTGAGGAAGCCTGGGGCCTCAGTGAAGGT TTCCTGCAAGGCTTCCGGATACACCTTCACTAAGTATGGTATGAATTGGGTGCGACAGGC CCCTGGACAAGGACTGGAGTGGATGGGATGGATTAACACGAACACTGCAAAGCCAACG TATGCCCAGGACTTCACAGGACGATTTGTCTTCTCTTTGGACACCTCTGTCAACACGGCAT ATCTGGAGATCAGCGGCCTAAAGGCTGAAGACACCGCCGTCTATTACTGTGCGACAGAT GGTAGTGAGGGCTCCTGGGGCCAGGGAACCACGGTCACCGTCTCCGCAAGCTTC | 1 |
| 1H9 light | AGATCTGACATCCAGATGACCCAGTCTCCTTCCACCCTGTTTGCATCTGTAGGAGACAGA GTCACCATCACTTGCCGGGCCAGTCAGAGTATTGGTACCTGGTTGGCCTGGCATCAGCA GAAACCAGGGACAGCCCCTAAGGTCCTGATCTATAAGGCGTCTAATTTAAAAAGTGGGG TCCCATCTAGATTTAGCGGCAGTGGATCTGGGACAGACTTCACTCTCACCATCAGCAGCC TGCAGCCTGATGATGTTGCAACTTATTACTGTCAACAATATAATACTTACTTGGGGACGTT CGGCCAAGGGACCCGGGTGGAGATCAAAACTGCGGCCGCA | 2 |
| 5C5 heavy | GAATTCCAGTTGTTGGAGTCAGGGGGAGGCTTGGTACAGCCGGGGGGGTCCCTGAGAC TCTCCTGTGCAGCCTCTGGATTCACCTTTAGCAACCATGCCATGAGCTGGGTCCGCCAGA CTCCAGGGGAGGGGCTGCAGTGGGTCTCAGCTCTTACTTATAGTGGTAAGACCACATAC TACGCAGACTCCGTGAAGGGCCGGTTCACCATCTCCAGAGACAATTCCAAGAATTTACTA TTTCTGCAAATGAACAGCCTGAGAGCCGGGGACACGGCCATATATTACTGTGCGAAGGA GGACTACGATGACCGGGGCTTCTTTGACTTCTGGGGCCAAGGGACAAGGGTCACCGTCT CCTCAGCAAGCTTC | 3 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 5C5 light | AGATCTGACATCCAGATGACCCAGTCTCCATCCTCCCTGTCTGCGTCTGTGGGAGACAGA GTCACCATCACTTGCCGGGCAAGTCAGACCATTAGTACTTATTTACATTGGTATCAACAAA AACCAGGCAAAGCCCCTAACCTCCTCATCTATGCTGCATCCACTTTGCAAAGTGGGGTCC CATCAAGGTTCAGTGGCAGTGGATCTGGGACAGATTTCAGTCTCACCATCAGTAGTCTGC GTCCTGAAGATTTTGCAATTTACTACTGTCAACAGGGTTACAATAACCCGTACACTTTTGG CCAGGGGACCAAAGTGGATATCAAAACTGCGGCCGCA | 4 |
| 1E7 heavy | GAATTCCAGTTGGTGGAGACTGGGGGAGGCGTGGTCCAGCCTGGGAGGTCCCTGAGAC TCTCGTGTGCAGCGTCTGGATTCATCTTCAGTAGTTACGGAATGCACTGGGTCCGCCAGG CTCCAGGCAAGGGGCTGGAGTGGGTGGCAGTTATATATTATGATGAAAATAATAAATAT TATGCAGACTCCGTGAAGGGCCGATTCACCATCTCCAGAGACAATTCCAAGAACACGCTC TCTCTGCAAATGAACAGCCTGAGAGCCGACGACACGGCTGTATATTACTGTGCGAGAGA TGTAGTAGTAGCTGCTTTTGACTTCTCCTACGGTATGGACGTCTGGGGCCAAGGGACCAC GGTCACCGTCTCCGCAAGCTTC | 5 |
| 1E7 light | GAATTCTCCTATGACCTGACTCAGCCACCCTCAGTGTCCGTGTCCCCAGGACAGACAGCC AACATCACCTGCTCTGGCAATAAACTGGAAAAATTTGGTTGCTGGTATCAGCAGAAGCCG GGCCAGTCCCCTCTTCTGGTCATCTATCAAGATAACAAGCGGCCCTCAGGGATCCCTGAG CGATTCTCTGGCTCCAACTCTGAGAACACAGCCACTCTGACCATCAGCGGGACCCAGGCT CTGGATGAGGCTGACTATTACTGTCAGGCGTGGGACGGCAGCTTCGGCGGAGGGACCA AGCTGACAGTCCTAAGCTTGCCC | 6 |
| 11B6 heavy | GAATTCCAGCTGTTGGAGTCTGGGGGAGGCTTGGTACAGCCCGGAGGGTCCCTGAGACT CTCCTGTGCAGCCTCTGGATTCACCTTTAGCACTTATGCCATGAGCTGGGTCCGCCAGGC TCCAGGGAAGGGGCTGGAGTGGGTCTCAACTATTAGTGGTAGCGGGAGCAGCACATAC GACGCAGACTCCGTGAAGGGCCGGTTCACCATCTCCAGAGACAAATTCAAAAGCACGGT GTATTTGCAAATGAATAGCCTGAGAGCCGAGGACACGGCCGTATATTACTGTGCGAGAG ATGTTCTCTACTCGGGGAGTTACTTTGACTACTGGGCCAGGAACACAATGGTCACCGTCT CTTCAGCAAGCTTC | 7 |
| 11B6 light | AGATCTCAGATGACCCAGTCTCCATCGTCCCTGTCTGCATCTATAGGAGACAGAGTCACC ATCACTTGCCGGGCAAGTCAGGGCATTAGAAATAATTTAGGCTGGTATCAGCAGACACC AGGGAAAGCCCCTAGGCTCCTGATCTATGCTGCATCCAGTTTACAAAGTGACGTCCCATC AAGGTTCAGCGGCAGTGGGTCTGGCACAGATTTCACTCTCACCATCAGCGCCCTGCAGCC TGAAGATTTTGCAACTTATTACTGTCTACAAGACTACAATTACCCTCGGACGTTCGGCCAA GGGACCAAGGTGGAAATCAAAACTGCGGCCGCA | 8 |
| 17A5 heavy | GAAGNGCANNTGGTGGAGTNTGGGGGAGGGTTGGTCAAGCCTGGGGGGTCCCTGAGA CTCTCCTGTGCAGCCTCTGGATTCCCCTTCAGTGATTATCACATGACCTGGATCCGCCAGG CTCCGGGGAAGGGGCTGGAATGGATTTCACACATCAGTAGTGCTGGCAATAAGATACAT TACGCAGAGTCTGTGAAGGGCCGGTTCACCATATCCAGGGACAACGCCAAGAATTCTTT GTTTTTGCACATGAACAGCCTGAGAGCCGAGGACACGGCCATGTATTACTGTGCCAGAG ATCCGGGATATTATCATGGTTCGGGGAATAAGCAA | 9 |
| 17A5 light | CAGTCTGTGTTGACGCAGCCGCCCTCAGTGTCTGCGGCCCCAGGACAGAGGGTCACCAT CTCCTGCTCTGGCGGCAGTTCCAACATTGGTTATAATTATGTGGCCTGGTACCAGCAATTC CCAGGAACAGCCCCCAAACTCCTCCTCTATGACGATGATGAGCGGCCCTCTGNCCTTCAC AAACAAGTTNNNCACCATCGCCTGGAGGATGCTTCTTCTCACCCTCCTCATTCAGGCCAC AGGGTCCTGGGCCCAGTCTGCCCTGACTCAACCTG | 10 |
| 12C8 heavy | GAAGTGCAGCTGGTGGAGTCTGGGGGAGGCTTGGTCCAGCCGGGGGGTCCCTGAAAC TCTCCTGTGCAGTCTCTGGGTTCAGCGTCAGTGACTCTGCTATACACTGGGTCCGCCAGG CTTCCGGGAAAGGACTGGAGTGGGTAGGCCACATGCGAAGTCAGGCGAACAGTTACGC GACAGCCTATGGTGCGTCGGTGAGAGGCAGGTTCAACATCTCCAGAGATGACTCAAAGA ACACGGCATATCTGCAAATGAACAGCCTGAACATCGATGACACGGCCGTATATTATTGTA CTAGAAAGGTGGATAATCGACACGGAATGGACGTCTGGGCCAAGGACCACGTC | 11 |
| 12C8 light | TCCTATGTGTTGACGCAGCCTCCCTCTGTGTCAGTGGCCCCAGGACAGACGGCCAGGATT CCCTGTGGGGGAAACAGCATTGGGAGTAGAAGTGTGCACTGGTACCAGCAGAAGCCAG GCCGGGCCCCTGTGTTGGTCATCTATTATGATAGGGACCGGCCCTCGGGGATCCCTGAG CGATTCTCTGGCTCCAACTCTGGGAACACGGCCACCCTGACCATCAGCAGGGTCGAGGC CGGGGATGAGGCCGACTACTACTGTCAGGTGTGGGATGGTAGTAGCGACCAATATGTCT TCGGAATTGGGACCAAGGTCACCGTCCTA | 12 |
| 2G1 heavy | GAATTCCAGCTGGTGGAGTCTGGAGGAGGCTTGATCCAGCCTGGGGGGTCCCTGAGACT CTCCTGTGCAGGCTCTGGGTTCACCGTCACTACCAACTACATGGCCTGGGTCCGCCAGGC TCCAGGGAAGGGGCTGGAGTGGGTCTCAACTATTTATAGCGCTGGTAGCACATTTTATG CGGACTCCGTGAAGGGCCGATTCACCATCTCCGGAGACAATTCCAAGAACACGCTGTATC TTCAAATGGGTAGCCTGAGAGCCGAGGACACGGCCGTCTATTACTGTGCGAGAGAAAAC CCTGCCCAGGATGCTTTTGATATCTGGGCCAAGGACACAATGGTCACCGTCTCTTCAGCA AGCTTC | 13 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 2G1 light | GAATTCTCCTATGAGTTGACTCAGCCACTCTCAGTGTCAGTGGCCCTGGGACAGACGGCC AGGATTACCTGTGGGGGAAACAACATTGGAAGTAAAAATGTTCACTGGTACCAGCAAAA GCCAGGCCTGGCCCCTGTGCTGGTCATCTATAGGGATAGCAACCGGCCCTCTGGGATCC CTGCGCGATTCTCTGGCTCCAGCTCGGGGAACACGGCCACCCTGACCATCAGCAGCGCCC AAGCCGGGGATGAGGCTGACTATTACTGTCATGTGTGGGACACCAGCACTGTGGTATTC GGCGGAGGGACTAAACTGACAGTCCTAAGCTTGCCCAAAGCCGCTCCTTCCGTGACTCTG TTTCCCCCTAGTTCAGAGGAACTGCAGGCCAACAAGGCTACACTGGTCTGTCTGATTTCT GACTTCTATCCTGGGGCCGTGACTGTCGCATGGAAGGCCGATAGCTCCCCAGTGAAAGC TGGCGTCGAGACCACAACTCCCTCTAAGCAGAGTAACAACAAGTATGCAGCCTCTAGTTA CCTGTCTCTGACCCCAGAACAGTGGAAGAGTCACAAAAGCTACTCCTGTCAGGTCACCCA CGAAGGCAGCACCGTCGAGAAAACAGTCGCACCCACCGAGTGTAGCTGACTCGAG | 14 |
| 5D10 heavy | CAGGTGCAGCTGCAGGAGTCGGGCCCAGGACTGGTGAAGCCTTCGGAGACCCTGTCCCT CACCTGCACTGTCTCTGGTGGCTCCATCAGTAGTGACTACTGGAGCTGGATTCGGCAGCC CCCAGGGAAGGGACTGGAGTGGATTGGGTACATCTATTATAGTGGGAGGACCTACTACA ACCCCTCTTTCAAGAGTCGAGTCGCCATATCACTAGACACGTCCAAGATCCAGTTTTCCCT GAACCCTGACCTCTGTGACCGCTGCGGACACGGCCGTTTATTACTGTGCGAGAGAGCGCC TAGACGCTTTTGATATGTGGGGCCAGGGGACAGTGGTCTTCGTCTCTTCAG | 15 |
| 5D10 light | CAGTCTGTGCTGACTCAGCCACCCTCAGCGTCTGGGACCCCCGGGCAGAGGGTCACCAT CTCTTGTTCTGGAGGCAGCTCCAACATCGGAAGTAATTATATGTATACTGGTACCAGCGGCT CCCAGGAACGGCCCCCAAACTCCTCATCTATAGGAATAATCAGCGGCCCTCAGGGGTCCC TGACCGATTCTCTGGCTCCAAGTCTGGCACCTCAGCCTCCCCGGCCATCAGTGGGCTCCG GTCCGAGGATGAGGCTGATTATTTCTGTGCAGCATGGGATGACAGGTTGAGTAGTTGGG TTTTCGGCGAAGGGACCAAGCTGACCGTCCTAG | 16 |
| 1E18 heavy | GTCCTGTGTCAGGTGCAGCTGGTGCAGTCGGGGGGAGGCTTGGTACAGCCTGGCAGGT CCCTGAGACTCTCCTGTGCAGCCTCTGGATTCACCTTTGATGATTATGCCATGCACTGGGT CCGGCAAGCTCCAGGGAAGGGCCTGGAGTGGGTCTCAGGTATTAGTTGGAATAGTGAT AGTATAGCCTATGCGGACTCTGTGAAGGGCCGATTCACCATCTCCAGAGACAACACCAA GAACTCCTTGTATCTGGAAATGAACAGTCTGAGACCTGAGGACACGGCCTTGTATTACTG CGCAAAAGTTCGTCTGGATTTTTGGACTGGTCCGATGGGGTACTTCCAGCACTGGGGCC GGGGCACCCTGGTCACCGTCTCCTCAGCAAGCTTC | 17 |
| 1E18 light | GAAATTGTGTTGACGCAGTCTCCAGGCACCCTGTCTTTGTCTCCAGGGGAAAGAGCCACC CTCTCCTGCAGGGCCAGTCAGACTATTACCAGCAACTATTTAGCCTGGTACCAGCAGAAA CCTGGCCAGGCTCCCAGGCTCCTCATCTATGGTGCCTCCACCAGGGCCACTGGCATCCCA GACAGGTTCAGTGGCAGTGGGTCTGGGACAGACTTCACTCTCACCATCAACAGACTGGA GCCTGAAGATTTTGCACTGTATTACTGTCAGCAGTATGGTAGCTACCGGGGGGTATTCAC TTTCGGCCCTGGGACCAAAGTGGATATCAAACGAACTGCGGCCGCACCATCTGTCTTCAT CTTCCCGCCA | 18 |
| 11A12 heavy | GAATTCCAGCTGGTGGAGTCTGGGGGAGGCTTCGTCCAGCCTGGGGGGTCCCTGAGACT CTCCTGTGCCGCCTCTGGATTCAGCGTCATTACCAATTACATGTCCTGGGTCCGCCAGGCT CCAGGAAAGGGGCTGGAGTGGGTCTCACTTATTTATAGCGGTGGTAGCACATACTACGC AGACTCCGTGAAGGGCCGATTCACCCTCTCCAGAGACAATTCCAAGAATACGCTAAATCT TCAAATGAACAGCCTGAGAGCTGAGGACACGGCTGTCTACTACTGTGCGAGAGTTGATA TAACAGCAACTGGTACGGGTGGTTTTGATATCTGGGCCAAGGACACAATGGTCACCGTC TCTTCAGCAAGCTTC | 19 |
| 11A12 light | GAATTCCAGTCTGCCCTGACTCAACCTGCCTCCGTGTCTGGGTCTCCTGGCCAGTCGATCA CCCTCTCCTGCACTGGAACCAGCAGTGATGTTGGGAGTTATAACCTTGTCTCATGGTACC AACAACACCCAGGCAAAGCCCCCAAACTCATGATTTATGAGGTCACTAAGCGGCCCTCAG GGGTTTCTAATCGCTTCTCTGGCTCCAAGTCTGGCAACACGGCCTCCCTGACAATCTCTGG GCTCCAGGCTGAGGACGAGGCTGATTATTACTGTTGCTCATATGCAGGTAGTAGCATTTC CTTTGTCTTCGGAACTGGGACCAAGGTCACAGTCCTAAGCTTG | 20 |
| 1J11 heavy | GAATTCCAGCTGGTGGAGTCTGGGGGAGGCGTGGTCCAGCCTGGGAGTTCCCTGAGAC TCTCCTGTGCAGTGTCTGGATTCACCGTCAGAAGCTATGGCATGCACTGGGTCCGCCAGG CTCCAGGCAAGGGGCTGGAGTGGGTGGCACTTATTTTGTTTGATGGAACTACAAAACAC TATGCAGACTCCGTGAAGGGCCGGTTCACCATCTCCAGAGACAATTCCAAGGACACTCTG TATCTGCAAATGACCAGCCTGGGAGCCGAGGACACGGCTATGTATTATTGTGTGAGAGA TTTCAACCAATTCGTTAAACGATTTGTGGATGGACCGGCTTTTGATCTCTGGGGCCAAGG GACAAGGGTCACCGTCTCCTCAGCAAGCTTC | 21 |
| 1J11 light | | 22 |
| 1A5 heavy | GAAGTGCAGCTGGTGGAGTCTGGGGGAGGCGTGGTCCAGCCTGGGAGGTCCCTGAGAC TCTCCTGTGCAGGCTCTGGATTCACCTTCAGTACCTATGTCATGCACTGGGTCCGCCAGG CTCCAGGCAAGGGGCTGGAGTGGGTGGCAGTTATATCATATGATGGAACTAATAAATAC TATGCAGACTCCATGAAGGGCCGATTCACCATCTCCAGAGACAATTCCAAGAACACGCTG TATCTGCAACTGAACCGCCTGAGAGCTGAGGACACGGCTGTGTATTACTGTGCGAAAAC AATGGATGATAGTAGTGGTTATTATTGTCCTGATTACTGG | 23 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 1A5 light | TCTTCTGAGCTGACTCAGGACCCTGCTGTGTCTGTGGCCTTGGGACAGACAGTCAAGATC<br>ACATGCCAAGGAGACAGCCTCAGAAACTATTTTGCAAACTGGTACCAGCAGAAGCCAGG<br>ACAGGCCCCTGTTCTTGTCATCTATGGTCAAAACAACCGGCCCTCAGGGATCCCAGACCG<br>ATTCTCTGGCTCCACCTCAGGAAACACAGGTTCCTTGACCATCACTGGGGCTCAGGCGGA<br>AGATGAGGCTGACTATTACTGTAACTCCCGGGACAGCAGTGGTAACCATCTTTATGTCTT<br>CGGAAC | 24 |
| 11H12 heavy | CAGGTCCAACTGGTGGAGTCTGGGGGAGACTTGGTCACGCCTGGAGGGTCCCTGAGAC<br>TGTCGTGTGCAGCCTCGGGATTCGCCTTTAGCGGCTACTACATGAGTTGGATCCGCCAGG<br>CTCCAGGGAAGGGGCTGGAATGGATCTCATACATTAATAGTAACGGTCTTACCATCTCCT<br>ACGCGGACTCTGTGAAGGGCCGATTCACCGTCTCCAGGGACAATGCCAAGAACTCACTG<br>TTTCTGCAAATGAGCTCCCTGAGAGCCGAGGACACGGCCATATATTACTGTGCGCGAGAT<br>TGGGGGACAACATTGGTAACTTTTGACCTCTGGGGCCAGGGAACCCTGGTCACCGTCTC<br>CTCA | 25 |
| 11H12 light | CAGCCTGTGCTGACTCAATCATCCTCTGCCTCTGCTTCCATGGGATCCTCGGCCAAGCTCA<br>CCTGTACTCTGAGTAGTGGCCACAGAGGCTACAACATCGCTTGGCTTCAGCAGCATCCAG<br>GGAAGGCCCCTCTCTATTTGACGAATCTTGAGGGTAGTGACTCCTACAAGAACGATCGCC<br>TCACAGTCTCCAGCTCTGGGGCTGACCGCTACCTCACCATCTCCAACCTCCAGCCTGAAG<br>ATGAGGCTACCTATTACTGCTTCACCTGGGACAGCGACTCCCGCGTCTTCGGCGGGGGG<br>ACGCACCTGACCGTCCTG | 26 |
| 7G12 heavy | CAGGTTCACTTGGTGCAGTCTGGAGTTGACGTGAAGAAGCCTGGGGCCTCAGTGAAACT<br>CTCCTGCAAGACTTCTGGTTACACCTTTACTAATTATGGTATTACTTGGGTGCGACAGGCC<br>CCTGGACAAGGGCTTGAGTGGATGGGCTGGATCAGCACTTACGATGGTGCCACAAACTA<br>TAGCCAGAATCTCCAGGGCAGAATCATCATGACCACTGACACATCCAAGAGGACAGCCT<br>ATCTGCAGATGAGGAGTCTGAGATCTGACGACACGGCCGTCTATTACTGTGCGAGGGGA<br>CGAGATAGTCCGGACCACTGGGGCCAGGGAACCCTGGTCACCGTCTCCTCA | 27 |
| 7G12 light | GACATCCAGATGACCCAGTCTCCTTCCACCCTGTCTGCATCTGTAGGAGACAGAGTCACC<br>ATCACTTGCCGGGCCAGTCAGAGTATTAATAGGTGGTTGGCCTGGTATCAGCAGAAACC<br>AGGGACAGCCCCTAAACTCCTCATCTTTAAGGCGTCTACTCTAGACAGTGGTGTCCCAGC<br>GAGGTTCAGCGGCACTGGATCTGAGACAGAATTCTCTCTGACCATCAACAGCCTGCAGCC<br>TGATGATTTTGCAACTTATTACTGCCAACAGTATGATCATTTTCCGCACACTTTTGGCCCG<br>GGGACCAAACTGGACATCAAA | 28 |
| 10H9 heavy | CAGGTGCAGCTGGTACAGTCTGGAACTGAGGTGAAAAAGCCTGGGGCCTCAGTGAAGG<br>TCTCCTGCAAGACTTCTGGTTACACCTTTATCAGTTATGGTGTCACCTGGGTGCGACAGG<br>CCCCTGGACAAGGGCTTGAGTGGATGGGATGGATCAGCGGTTACAATGGTAACCCAAAA<br>TATGCAGAGAAGTTCCACGACAGAATAACCATGACCACAGACAGATCGACGAACACAGT<br>CTACTTGGAATTGAGGAGCCTGAGATCTGACGACACGGCCGTGTATTACTGTGCGAGAT<br>GGATGGTGGGAAATATTAACCCCTTTGACCACTGGGCC | 29 |
| 10H9 light | TCAGAAACTCATTTGGAACTGGTACAAGCAGACGCCANGACNAGTTCCTGTTCTNNNTN<br>NTNTATGGTCAAAACANCCGGCCCNCAGTGATCCCAGACCGATTCTCTGGCTCCACCTCA<br>GGAAACACCGGNTCCTTGACCATCACTGGGGNTCAGGCGGAAGATGAGGATGATTATT<br>ACTGTAACTCCCGGGACAGCAGTGGTAACCATTTTTATGTCTTCGGAACTGGGACCAAGG<br>TCACCGTCCTAG | 30 |
| 11G1 heavy | GGAGGTGCAGGTGGGCCAGTCTGGACCAGTGCTAAAAAAGCCGGGGGAGTCTATGAAG<br>ATCTCCGGTAGGGGGTCGGGATACAGGTTCAACACTTATTGGGTCGCCTGGGTGCGCCA<br>GATGCCCGGGAAAGGTCTGGAGTGGATGGGAATGATCTATCCGGGTGACTTGGATACG<br>AAATATAGTCCGTCCTTCCAAGGCCAAGTCACCATTTCAGCCGACAAGTCCAGCAATACC<br>GCCTACCTACAGTGGAGTAGTCTGAAGGCCTCGGACACCGCCATGTATTATTGTGCGAG<br>AGAAGTATATGTGGCTTCGACTGATAGTGACTATTACGGTATGGACGTCTGGGCCTAGG<br>ACCA | 31 |
| 11G1 light | CAGTCTGCCCTGACTCAGCCTGCCTCCGTGTCTGGGTCTCCTGGACAGTCGATCACCATCT<br>CCTGCACTGGAACCAGCAATGATGTTGGGCGTTCTGACCTTGTCGCCTGGTACCAACAAC<br>ACCCCGACAAGGCCCCCAGACTCATTATTTATGAGTCCAGTAAGCGGCCCTCAGGGGTTT<br>CTGCCCGCTTCTCTGGCTCCAGGTCTGGCATCACGGCCTCCCTGACCATCTCTGACCTCCA<br>GGCTGAAGACGAGGCTGACTATTACTGCTGTTCATATGCAGGTGGTAACACTTATGTCTT<br>CGGCACCGCGACCGGGGTCACCGTCCTAG | 32 |
| 14B2 heavy | GAAGTGCAGCTGGTGGAGACTGGAGGAGGCTTGATTCAGCCGGGGGGTCCCTGCGAC<br>TCTCCTGTGCAGCCTCTGGGTTCAGCGTCAGTACGAGGTTCATGAGCTGGGTCCGCCAG<br>GCTCCAGGTCAGGGACTGGAGTGGGTCTCAGTCGTCTATAAAGATGGTGACACCTTCAA<br>CTCGGACTCCGTGAAGGGCCGATTCAGCATCTCCAGAGACAATTCCAAGAACACAGTGTT<br>TCTTCAAATGAACAGACTGAAGAGTCGAAGACACTGCCGTATACTTCTGTGTGCGACATGG<br>CGATGGTTGGAATTACGTCGACTCCTGGGGCCTGGAAC | 33 |
| 14B2 light | GAAATAGTGATGACGCAGTCTCCAGCCACCCTGTCTGTGTCTCCAGGGGAAGGAGCCAC<br>CCTCTCCTGCAGGGCCAGTCACAGTCTTAGTAGTCACTTAGCCTGGTACCAGCAAAAACC<br>TGGCCAGGCTCCCAGGCTCCTAATATATGATGCATCCGTCAGGGCCACTGATATCCCAGC | 34 |

TABLE A-continued

NUCLEOTIDE SEQUENCES FOR IgE ANTIBODY VARIABLE REGIONS

| Clone | Variable Sequence Region | SEQ ID NO: |
|---|---|---|
| | CAGGTTCAGTGGCAGTGGGTCTGGGACAGAGTTCACTCTCACCATCAGCAGCCTGCAGT CTGAAGATTTTGCAGTTTACTACTGTCAGCAATATAATAACTGGCCGCTCACTTTCGGCG GAGGGACCAAGCTGGAGATCAAAC | |
| 12F9 heavy | GAAGTGCAGCTGGTGGAGTCTGGGGGAGACTTGGTCAAGCCTGGAGGGTCCCTGAGAA TCTCCTGTGCAGCCTCTGGATTCAGCTTCAGTGACTACTACATGAGTTGGATCCGCCAGG CTCCAGGGAAGGGGCTTGAATGGGTTGCGTATATTAGTGGATCCAGTGCCTACACAAGC TACGCGGACTCTGTGAAGGGCCGCTTCTCCATCTCCAGAGACAACGCCAACAACTCACTC TTTCTACAAATGAACAGCCTGAGAGCCGAGGACACGGCTACATATTTCTGTGCGAAAGAT TACTGTGGCAGTGGCGCCTGCTACACTGCGGACCCTGGCTTCTTCCATCAATGGGCCAGG | 35 |
| 12F9 light | TCCTATGTTCTGACTCAGCCGCCCTCAGTGTCGGTGGCCCCAGGAAAGACGGCCACGATT TCCTGTGGGGGAAACAACATTGGAAGTAAAAGTGTGCACTGGTATCAGCAGAAGCCAG GCCAGGCCCCTATAGTGGTCATCTATTATGATAGCGACCGGCCCTCAGGGATCCCTGAGC GATTTTCTGGAATCAATTCTGGGAACACGGCCACCCTGACCATCAGCAGGGTCGAAGCC GGGGATGAGGCCGACTATTATTGTCAGGTGTGGGACAATACTAATGATCATCCCTCTTAT GTCTTCGGAGCTGGGACCAAGGTCACCNTCCTAG | 86 |
| 15A10 heavy | GAAGTGCAGCTGTTGGAGTCTGGGGGAGGCTTGGTACAGCCCGGAGGGTCCCTGAGAC TCTCCTGTGCAGCCTCTGGATTCACCTTTAGCACTTATGCCATGAGCTGGGTCCGCCAGG CTCCAGGGAAGGGGCTGGAGTGGGTCTCAACTATTAGTGGTAGCGGGAGCAGCACATA CGACGCAGACTCCGTGAAGGGCCGGTTCACCATCTCCAGAGACAAATTCAAAGCACGG TGTATTTGCAAATGAATAGCCTGAGAGCCGAGGACACGGCCGTATATTACTGTGCGAGA GATGTTCTCTACTCGGGGAGTT | 37 |
| 15A10 light | GACATCCAAATGACCCAGTCTCCATCCTCCCTGTCTGCATCTGTAGGAGACAGAGTCACT ATCTCTTGCCGGGCAAGTCAGGACGTTGGCAAATATTTAAATTGGTATCAACAGAAACCA GGGGAAGCCCCTAAACTCCTGATCTATGCAGCATCTCGTTTAGATAGGGGAGTCTCGTCA AGGTTCAGTGGCAGTGGAATCGGGGCAGACTTCACTCTCACCATCAGCGGTCTGCAACC TGAAGATTTTGCAACTTACTACTGTCAACAGAGTTCCAGTACCGCTGCGTGGACGTTCGG CCAAGGGACCAAGGTGGAAATCAAAAG | 38 |
| 3F11 heavy | CAGCTGCAGAAGCAGCAGTGGGCCGCAGGACTGAAGCATCCGTCGGCGACCCTCTCCTT CATATGCGGTATCAATGGTGGTTCCTTCAGTGGTTTCTTGCGGACATGGATCCGCCAGTC CCCAGGGAAGGGGGTGGAATTGATTGGAGAAATCAATAATAGTGGCACCACCAAATAC AATTCGTCCCTAAGAGTCGACTCACCATATCAATAGACACGTCCAAGGACCAGGTCTCC CTACAGTTGCGCTCTGTGACCGCCGCGGACACGGCTACATATTTCTGTGCGAGAACTCCT GTCCTCCGATATTTGACAGTTGGGCCATGGGGCCAGGGAACCCTG | 89 |
| 3F11 light | TCCTATGAGCTGACTCAGCCACCCTCAGTGTCCCTGTCCCCCGGACAGACAGCCACCATC ACATGCTCGGGAGATAAATTGGGGGATAAATCTGTTTCCTGGTATCAACAGATGCCAGG CCAGTCCCCATTTTGGTCATCTATCAAGATTACAAACGGCCCTCAGGAATCTCTGAGCG ATTCTCTGGCTCCAACTCTGGGAACACAGCCACTCTGACCATCAGCGAGACCCAGGCTAT GGATGAGGCTGACTATTACTGTCAGGCGTGGGACAGGAAGATTGGGCAATTTGGCGGA GGGACCAAGATGACCGTCATAG | 40 |
| 13D9 heavy | CAGGTGCAGCTGGTGGAGTCTGGGGGAGGCTTGGTCAAGCCTGGAGGGTCCCTCAGAC TCTCCTGCGTAGCCTCTGGATTCACCTTCAGTGACTTCTACATGAGCTGGATCCGCCAGGC TCCAGGGAAGGGGCCTTGAGTGCGTGTCCTACATGAGTGCAACTGGCGGTAATATATACT ATGCAGACTCTATGAAGGGCCGATTAACTATCTCCAGGGACAACACCAAGAACTCATTGT TTCTCCAAATGAACAGCCTGAGAGCCGACGACACGGCCCTGTATTATTGTGCGAGGCGG AAGTTTGGTGCAGGGAGTGCGATCTTTGACCACTGGAGCCAGGGAACCCTGGTCACCGT CTCCTCAG | 41 |
| 13D9 light | TCCTATGAACTGACTCAACCACCCTCAGTGTCCGTGTCCCCAGGACAGACAGCCAGCGTC ACCTGCTCTGGAGACAAATTGGGTGAAAGATATGTGAGTTGGTATCAGCAGAAGGCAG GCCAGTCCCCTGACTTGGTCATCTATCAAACTAACCAGCGGCCCTCAGGGATCCCTGAGC GATTCTCTGGCTCCGACTCTGGGAACACAGCCACTCTGACTATCAGCGGGACCCAGGGTC TGGATGAGGCAGACTATTACTGTCTGACGTGGGACCGCGGCACTCCTGTCTTCGGAACT GGGACCAAAGTCACCGTCCTAG | 42 |
| 8F3 heavy | CAGCTGCAGCTGCAGGAGTCGGGCCCAGGCCTGGTGAAGCCTTCGGAGACCCTGTCCCT CACCTGCACTGTGTCTGATGCCTCCATCGACACTCCGAGTTACTTCTGGAGCTGGATCCG CCAGCCCCCAGGGAAGGGGCTGGAGTGGATTGGCAGCATCTATTATACTGGGAACAAGT ACTCCAATCCGTCCCTAAGAGTCGAGTCACCATGTCCGTAGACACGCCCAAGAGGCAGT TCTCCCTGAGGCTCAGCTCTGTGACCGCCGCAGACACGGCTGTTTATTACTGTGCGAGAT ATGTTGATTATGTTTGGTTGAGGGCTTTTGATATATGGGGCCAAGGGACAAGGGTCACC GTCTCCTCAG | 43 |
| 8F3 light | GAAATTGTGTTGACACAGTCTCCAGCCACGCTGTCTTTGTCTCCAGGGGAAAGGGCCACC CTCTCATGCAGGGCCAGTCCGAGTGCTGGCCGCTTCTTAGCTTGGTACCAACAGAGACCT GGCCAGGCTCCCAGGCTCCTCATCTATGATGCATCCAAGAGGGCCACTGACACCCCAGCC AGGTTCAGTGGCAGCGGGTCTGGGACAGACTTCAATCTTACCATCGCCAGCCTAGAGCC TGAAGATTTTGCAGTTTATTACTGTCAACACCGTAGCAACTGGCCGCTCACTTTCGGCGG AGGGACCAAGGTGGAGATCAAAC | 44 |

TABLE A-continued

NUCLEOTIDE SEQUENCES FOR IgE ANTIBODY VARIABLE REGIONS

| Clone | Variable Sequence Region | SEQ ID NO: |
|---|---|---|
| 1A8 heavy | CAGCTGCAGCTGCAGGAGTCGGGCCCAGGACTGGTGAAGCCTTCGGAGACCCTGTCACT<br>CACCTGCAGTGTCTCTGATGACTCCATCAGTACTCCTAGTTACTTCTGGACCTGGATCCGC<br>CAGCCCCCAGGGAAGGGGCTGGAGTGGATAGCCAGTATCTATTATACTGGGACCACCTA<br>CTACAACCCGTCCCTCAAGAGTCGAGTCACCTTATCCGTCGACACGCCCAAGAGGCAGTT<br>CTTCCTGAGGCTGAGCTCTGTGACCGCCGCAGACACGGCTGTTTATTACTGTGCGAGATA<br>TCTTGATTACGTTTGGTTGAGGGCTTTTGATGTCTGGGGCCAAGGGGCAATGGTCACCGT<br>CTCTTCAG | 45 |
| 1A8 light | GAAATTGTGTTGACACAGTCTCCAGCCACCCTGTCTTTGTCTCCAGGGGAAAGAGCCACC<br>CTCTCCTGCAGGGCCAGTCCGAGTGTTGGCAGGTTCTTAGCCTGGTACCAGCAGAAACCT<br>GGCCAGGCTCCCAGGCTCCTCATCTATGATGCATCTCAGAGGGCCACTGACATCCCAGCC<br>AGGTTCAGTGCCAGTGGGTCTGGGACAGACTTCACTCTCACCATCGACAGCCTAGAGCCT<br>GAAGATTTTGCAATATATTACTGTCAGCACCGTAGCAACTGGCCGGTCACTTTCGGTGGA<br>GGGACCAGGGTGGAGATCAAGC | 46 |
| 1C14 heavy | CAGGTGCAGCTGCAGGAGTCGGGCCCAGGACTGGTGAAGCCTTCACAGACCCTGTCCCT<br>CACCTGCACTGTCTCTGGTGGCTCCATCAGCAGTGGTGGTTTCTTCTGGGGCTGGATCCG<br>CCAGCACCCAGGGAGGGACCTGGAGTGGATTGGGTACATCTTTTACACTGGGAGCACCA<br>ACTACAACCCGTCCCTCAAGAATCGAGTTACCCTATCAGTAGACACGTCAAGAACCACT<br>TCTCCCTGAACTTGACCTCTGTGACTGTCGCGGATACGGCCGTCTATTACTGTGCGAGAC<br>AAGGGGGAGTGAGGGGGAACTACTACTTCATGGACGTCTGGGGCAAAGGGACCACGGT<br>CACCGTCTCCTCA | 47 |
| 1C14 light | GACATCCAGATGACCCAGTCTCCATCCTCCCTGTCTGCGTCTGTTGGAGACAGAGTCACC<br>ATCACTTGCCGGGCAAGTCAGAGTATTAGCAACTATTTAAATTGGTATCAACAGAAACCA<br>GGGAAAGCCCCTAAACTCCTTATCTATGCTGCATCCAGATTGCAGAGTGGGGTCCCATCA<br>AGGTTCAGTGGCAGTGGATCTGGGACAGAGCTCACCCTCACCATCAGCAGTCTGCAACC<br>TGAAGATTTTGCAACTTATTTCTGTCAACAGAGTTACAATACACCCTACTCTTTTGGCCAG<br>GGGACCAAGGTAGAGATCAAAG | 48 |
| 1B7 heavy | ATGGAATTCCAGCTGCAGGAGTCGGGCCCAGGACTGGTGAAGCCTTCGGAGACCCTGTC<br>CCTCAACTGCAGTGTCTCTGGTGGCTCCATCAGTAATAATTATTGGAACTGGATCCGGCA<br>GCCCCCAGGGAAGGGACTGGAGTGGATTGGGTATATCTCTTACAGTGGGAGAACCCATT<br>ACAACCCGTCCCTCAAGAGTCGGGTCAGCATATCATTGCACACGTCCAAGAACCATTTCT<br>CCCTGAAGCTGACCTCTGTGGCCGCTGCGGACACGGCCATGTATTACTGTGCGAGAGAG<br>TCGACATACAGTTATAAACTAGGTGATGCTTTTGATATCTGGGGCCAAGGGACAATGGTC<br>ACCGTCTCCGCAAGCTTC | 49 |
| 1B7 light | ATGGAATTCCAGTCTGTGCTGACTCAGCCGCCCTCAACGTCTGGGACCCCCGGGCAGAG<br>GGTCACCATCTCTTGTTCTGGAAGCAGCTCCAACATCGGACGTAATACTTTAAACTGGTA<br>CCAGCAGGTCCCAGGAACGGCCCCCAAACTCCTCATTTATAGTAATGATGAGCGGCCCTC<br>AGGGGTCCCTGACCGATTCTCTGGCTCCAAGTCTGGCCCCTCAGCCTCCCTGGCCATCAG<br>TGGGCTCCAGTCTGAGGATGAGGCTGATTATTACTGTGCAGCATGGGATGACAGGCTGA<br>ATGGTTGGGTGTTCGGCGGAGGGACCAAGCTGACCGTCCTAAGCTTG | 50 |
| 14H4 heavy | GAGGTGCAGCTGGTGCAGTCTGGAGCAGAGGTGAAGAGGGCCGGGGAGTCTCTGAAG<br>ATCTCCTGTAAGGGTTCTGGATACCCCTTTGCCACCTACTGGGTCGGCTGGGTGCGCCAG<br>ATGCCCGGAAAAGGCCTGGAATGGATGACTATCATCTATCCTGAGGACTCCGACACCAG<br>ATACAGCCCGTCCTTCCAAGACCATGTCACCATCTCAGCCGACAAGTCCCTCAGCACCGC<br>CTACCTGCAGTGGAGCAGCCTAAAGGCCTCGGACACAGCCATGTATTACTGTGCGAGAG<br>TGTCCCGGTATTATTATGATAGTAGAAGTTATTACCCTGATGCTTTTGACATCTGGGGCCA<br>AGGGACAATGGTCACCGTCTCCTCAG | 51 |
| 14H4 light | TCCTATGAGCTGACTCAGCCACCCTCAGTGTCCGTGTCCCCAGGACAGACAGCCAGCATC<br>ACCTGCTCTGGAGATAAATTGGGGGATAAATATGTTTGCTGGTATCAACAGAAGCCAGG<br>CCGGTCCCCTGTGTTGGTCGTCCATCAAGATACCAAGCGGCCCTCAGGGATCCCTGAGCG<br>ATTCTCTGGCTCCAATTCTGGGGACACAGCCACTCTGACCATCAGCGGGACCCAGGCTAT<br>GGATGAGGCTGACTATTACTGTCAGGCGTGGGACAGTACCATTGGGGTCTTCGGGCCTG<br>GGACCAGGGTCACCGTCCTAG | 52 |

TABLE B

PROTEIN SEQUENCES FOR ANTIBODY VARIABLE REGIONS

| Clone | Variable Sequence | SEQ ID NO: |
|---|---|---|
| 1H9 heavy | EFQLVQSGSELRKPGASVKVSCKASGYTFTKYGMNWVRQAPGQGLEWMGWINTNTAKPT<br>YAQDFTGRFVFSLDTSVNTAYLEISGLKAEDTAVYYCATDGSEGSWGQGTTVTVSASF | 53 |

TABLE B-continued

PROTEIN SEQUENCES FOR ANTIBODY VARIABLE REGIONS

| Clone | Variable Sequence | SEQ ID NO: |
|---|---|---|
| 1H9 light | RSDIQMTQSPSTLFASVGDRVTITCRASQSIGTWLAWHQQKPGTAPKVLIYKASNLKSGVPS RFSGSGSGTDFTLTISSLQPDDVATYYCQQYNTYLGTFGQGTRVEIKTAAA | 54 |
| 5C5 heavy | EFQLLESGGGLVQPGGSLRLSCAASGFTFSNHAMSWVRQTPGEGLQWVSALTYSGKTTYYA DSVKGRFTISRDNSKNLLFLQMNSLRAGDTAIYYCAKEDYDDRGFFDFWGQGTRVTVSSASF | 55 |
| 5C5 light | RSDIQMTQSPSSLSASVGDRVTITCRASQTISTYLHWYQQKPGKAPNLLIYAASTLQSGVPSR FSGSGSGTDFSLTISSLRPEDFAIYYCQQGYNNPYTFGQGTKVDIKTAAA | 56 |
| 1E7 heavy | EFQLVETGGGVVQPGRSLRLSCAASGFIFSSYGMHWVRQAPGKGLEWVAVIYYDENNKYYA DSVKGRFTISRDNSKNTLSLQMNSLRADDTAVYYCARDVVVAAFDFSYGMDVWGQGTTVT VSASF | 57 |
| 1E7 light | EFSYDLTQPPSVSVSPGQTANITCSGNKLEKFGCWYQQKPGQSPLLVIYQDNKRPSGIPERFS GSNSENTATLTISGTQALDEADYYCQAWDGSFGGGTKLTVLSLP | 58 |
| 11B6 heavy | EFQLLESGGGLVQPGGSLRLSCAASGFTFSTYAMSWVRQAPGKGLEWVSTISGSGSSTYDAD SVKGRFTISRDKFKSTVYLQMNSLRAEDTAVYYCARDVLYSGSYFDYWARNTMVTSSASF | 59 |
| 11B6 light | RSQMTQSPSSLSASIGDRVTITCRASQGIRNNLGWYQQTPGKAPRLLIYAASSLQSDVPSRFS GSGSGTDFTLTISALQPEDFATYYCLQDYNYPRTFGQGTKVEIKTAAA | 60 |
| 17A5 heavy | EVQLVESGGGLVKPGGSLRLSCAASGFPFSDYHMTWIRQAPGKGLEWISHISSAGNKIHYAE SVKGRFTISRDNAKNSLFLHMNSLRAEDTAMYYCAR | 61 |
| 17A5 light | QSVLTQPPSVSAAPGQRVTISCSGGSSNIGYNYVAWYQQFPGTAPKLLLYDDDERPSXLHKQ VXHHRLEDASSHPPHSGHRVLGPVCPDST | 62 |
| 12C8 heavy | EVQLVESGGGLVQPGGSLKLSCAVSGFSVSDSAIHWVRQASGKGLEWVGHMRSQANSYAT AYGASVRGRFNISRDDSKNTAYLQMNSLNIDDTAVYYCTRKVDNRHGMDVWAKDHV | 63 |
| 12C8 light | SYVLTQPPSVSVAPGQTARIPCGGNSIGSRSVHWYQQKPGRAPVLVIYYDRDRPSGIPERFSG SNSGNTATLTIDRVEAGDEADYYCQVWDGSSDQYVFGIGTKVTVL | 64 |
| 2G1 heavy | EFQLVESGGGLIQPGGSLRLSCAGSGFTVTTNYMAWVRQAPGKGLEWVSTIYSAGSTFYAD SVKGRFTISGDNSKNTLYLQMGSLRAEDTAVYYCARENPAQDAFDIWAKDTMVTVSSASF | 65 |
| 2G1 light | EFSYELTQPLSVSVALGQTARITCGGNNIGSKNVHWYQQKPGLAPVLVIYRDSNRPSGIPARF SGSSSGNTATLTISSAQAGDEADYYCHVWDTSTVVFGGGTKLTVLSLPKAAPSVTLFPPSSEEL QANKATLVCLISDFYPGAVTVAWKADSSPVKAGVETTTPSKQSNNKYAASSYLSLTPEQWKS HKSYSCQVTHEGSTVEKTVAPTECS | 66 |
| 5D10 heavy | QVQLQESGPGLVKPSETLSLTCTVSGGSISSDYWSWIRQPPGKGLEWIGYIYYSGRTYYNPSF KSRVAISLDTSKIQFSLNLTSVTAADTAVYYCARERLDAFDMWGQGTVVFVSS | 67 |
| 5D10 light | QSVLTQPPSASGTPGQRVTISCSGGSSNIGSNYVYWYQRLPGTAPKLLIYRNNQRPSGVPDR FSGSKSGTSASPAISGLRSEDEADYFCAAWDDRLSSWVFGEGTKLTVL | 68 |
| 1E18 heavy | VLCQVQLVQSGGGLVQPGRSLRLSCAASGFTFDDYAMHWVRQAPGKGLEWVSGISWNSD SIAYADSVKGRFTISRDNTKNSLYLEMNSLRPEDTALYYCAKVRLDFWTGPMGYFQHWGRG TLVTVSSASF | 69 |
| 1E18 light | EIVLTQSPGTLSLSPGERATLSCRASQTITSNYLAWYQQKPGQAPRLLIYGASTRATGIPDRFS GSGSGTDFTLTINRLEPEDFALYYCQQYGSYRGVFTFGPGTKVDIKRTAAAPSVFIFPP | 70 |
| 11A12 heavy | EFQLVESGGGFVQPGGSLRLSCAASGFSVITNYMSWVRQAPGKGLEWVSLIYSGGSTYYADS VKGRFTLSRDNSKNTLNLQMNSLRAEDTAVYYCARVDITATGTGGFDIWAKDTMVTVSSASF | 71 |
| 11A12 light | EFQSALTQPASVSGSPGQSITLSCTGTSSDVGSYNLVSWYQQHPGKAPKLMIYEVTKRPSGV SNRFSGSKSGNTASLTISGLQAEDEADYYCCSYAGSSISFVFGTGTKVTVLSL | 72 |
| 1J11 heavy | EFQLVESGGGVVQPGSSLRLSCAVSGFTVRSYGMHWVRQAPGKGLEWVALILFDGTTKHYA DSVKGRFTISRDNSKDTLYLQMTSLGAEDTAMYYCVRDFNQFVKRFVDGPAFDLWGQGTR VTVSSASF | 73 |
| 1J11 light |  | 74 |
| 1A5 heavy | EVQLVESGGGVVQPGRSLRLSCAGSGFTFSTYVMHWVRQAPGKGLEWVAVISYDGTNKYY ADSMKGRFTISRDNSKNTLYLQLNRLRAEDTAVYYCAKTMDDSSGYYCPDYW | 75 |
| 1A5 light | SSELTQDPAVSVALGQTVKITCQGDSLRNYFANWYQQKPGQAPVLVIYGQNNRPSGIPDRF SGSTSGNTGSLTITGAQAEDEADYYCNSRDSSGNHLYVFG | 76 |

TABLE B-continued

PROTEIN SEQUENCES FOR ANTIBODY VARIABLE REGIONS

| Clone | Variable Sequence | SEQ ID NO: |
|---|---|---|
| 11H12 heavy | QVQLVESGGDLVTPGGSLRLSCAASGFAFSGYYMSWIRQAPGKGLEWISYINSNGLTISYADS VKGRFTVSRDNAKNSLFLQMSSLRAEDTAIYYCARDWGTTLVTFDLWGQGTLVTVSS | 77 |
| 11H12 light | QPVLTQSSSASASMGSSAKLTCTLSSGHRGYNIAWLQQHPGKAPLYLTNLEGSDSYKNDRLT VSSSGADRYLTISNLQPEDEATYYCFTWDSDSRVFGGGTHLTVL | 78 |
| 7G12 heavy | QVHLVQSGVDVKKPGASVKLSCKTSGYTFTNYGITWVRQAPGQGLEWMGWISTYDGATN YSQNLQGRIIMTTDTSKRTAYLQMRSLRSDDTAVYYCARGRDSPDHWGQGTLVTVSS | 79 |
| 7G12 light | DIQMTQSPSTLSASVGDRVTITCRASQSINRWLAWYQQKPGTAPKLLIFKASTLDSGVPARFS GTGSETEFSLTINSLQPDDFATYYCQQYDHFPHTFGPGTKLDIK | 80 |
| 10H9 heavy | QVQLVQSGTEVKKPGASVKVSCKTSGYTFISYGVTWVRQAPGQGLEWMGWISGYNGNPK YAEKFHDRITMTTDRSTNTVYLELRSLRSDDTAVYYCARWMVGNINPFDHWA | 81 |
| 10H9 light | RNSFGXWYKQTPXXVPVLXXYGQNXRPXVIPDRFSGSTSGNTGSLTITGXQAEDEDDYYCNS RDSSGNHFYVFGTGTKVTVL | 82 |
| 11G1 heavy | EVQVGQSGPVLKKPGESMKISGRGSGYRFNTYWVAWVRQMPGKGLEWMGMIYGDLDTK YSPSFQGQVTISADKSSNTAYLQWSSLKASDTAMYYCAREVYVASTDSDYYGMDVWA | 83 |
| 11G1 light | QSALTQPASVSGSPGQSITISCTGTSNDVGRSDLVAWYQQHPDKAPRLIIYESSKRPGVSARF SGSRSGITASLTISDLQAEDEADYYCCSYAGGNTYVFGTATGVTVL | 84 |
| 14B2 heavy | EVQLVETGGGLIQPGGSLRLSCAASGFSVSTRFMSWVRQAPGQGLEWVSVVYKDGDTFNS DSVKGRFSISRDNSKNTVFLQMNRLRVEDTAVYFCVRHGDGWNYVDSWGLE | 85 |
| 14B2 light | EIVMTQSPATLSVSPGEGATLSCRASHSLSSHLAWYQQKPGQAPRLLIYDASVRATDIPARFS GSGSGTEFTLTISSLQSEDFAVYYCQQYNNWPLTFGGGTKLEIK | 86 |
| 12F9 heavy | EVQLVESGGDLVKPGGSLRISCAASGFSFSDYYMSWIRQAPGKGLEWVAYISGSSAYTSYADS VKGRFSISRDNANNSLFLQMNSLRAEDTATYFCAKDYCGSGACYTADPGFFHQWAR | 87 |
| 12F9 light | SYVLTQPPSVSVAPGKTATISCGGNNIGSKSVHWYQQKPGQAPIVVIYYDSDRPSGIPERFSGI NSGNTATLTISRVEAGDEADYYCQVWDNTNDHPSYVFGAGTKVTXL | 88 |
| 15A10 heavy | EVQLLESGGGLVQPGGSLRLSCAASGFTFSTYAMSWVRQAPGKGLEWVSTISGSGSSTYDA DSVKGRFTISRDKFKSTVYLQMNSLRAEDTAVYYCAR | 89 |
| 15A10 light | DIQMTQSPSSLSASVGDRVTISCRASQDVGKYLNWYQQKPGEAPKLLIYAASRLDRGVSSRFS GSGIGADFTLTISGLQPEDFATYYCQQSSSTAAWTFGQGTKVEIK | 90 |
| 3F11 heavy | QLQKQQWAAGLKHPSATLSFICGINGGSFSGFLRTWIRQSPGKGVELIGEINNSGTTKYNSSL KSRLTISIDTKDQVSLQLRSVTAADTATYFCARTPVLRYLTVGPWGQGTL | 91 |
| 3F11 light | SYELTQPPSVSLSPGQTATITCSGDKLGDKSVSWYQQMPGQSPILVIYQDYKRPSGISERFSGS NSGNTATLTISETQAMDEADYYCQAWDRKIGQFGGGTKMTVI | 92 |
| 13D9 heavy | QVQLVESGGGLVKPGGSLRLSCVASGFTFSDFYMSWIRQAPGKGLECVSYMSATGGNIYYA DSMKGRLTISRDNTKNSLFLQMNSLRADDTALYYCA | 93 |
| 13D9 light | SYELTQPPSVSVSPGQTASVTCSGDKLGERYVSWYQQKAGQSPDLVIYQTNQRPSGIPERFS GSDSGNTATLTISGTQGLDEADYYCLTWDRGTPVFGTGTKVTVL | 94 |
| 8F3 heavy | QLQLQESGPGLVKPSETLSLTCTVSDASIDTPSYFWSWIRQPPGKGLEWIGSIYYTGNKYSNPS LKSRVTMSVDTPKRQFSLRLSSVTAADTAVYYCARYVDYVWLRAFDIWGQGTRVTVSS | 95 |
| 8F3 light | EIVLTQSPATLSLSPGERATLSCRASPSAGRFLAWYQQRPGQAPRLLIYDASKRATDTPARFSG SGSGTDFNLTIASLEPEDFAVYYCQHRSNWPLTFGGGTKVEIK | 96 |
| 1A8 heavy | QLQLQESGPGLVKPSETLSLTCSVSDDSISTPSYFWTWIRQPPGKGLEWIASIYYTGTTYYNPS LKSRVTLSVDTPKRCIFFLRLSSVTAADTAVYYCARYLDYVWLRAFDVWGQGAMVTVSS | 97 |
| 1A8 light | EIVLTQSPATLSLSPGERATLSCRASPSVGRFLAWYQQKPGQAPRLLIYDASQRATDIPARFSA SGSGTDFTLTIDSLEPEDFAIYYCQHRSNWPVTFGGGTRVEIK | 98 |
| 1C14 heavy | QVQLQESGPGLVKPSQTLSLTCTVSGGSISSGGFFWGWIRQHPGRDLEWIGYIFYTGSTNYN PSLKNRVTLSVDTSKNHFSLNLTSVTVADTAVYYCARQGGVRGNYYFMDVWGKGTTVTVSS | 99 |
| 1C14 light | DIQMTQSPSSLSASVGDRVTITCRASQSISNYLNWYQQKPGKAPKLLIYAASRLQSGVPSRFS GSGSGTELTLTISSLQPEDFATYFCQQSYNTPYSFGQGTKVEIK | 100 |
| 1B7 heavy | EFQLQESGPGLVKPSETLSLNCSVSGGSISNNYWNWIRQPPGKGLEWIGYISYSGRTHYNPSL KSRVSISLHTSKNHFSLKLTSVAAADTAMYYCARESTYSYKLGDAFDIWGQGTMVTVSA | 101 |

TABLE B-continued

PROTEIN SEQUENCES FOR ANTIBODY VARIABLE REGIONS

| Clone | Variable Sequence | SEQ ID NO: |
|---|---|---|
| 1B7 light | QSVLTQPPSTSGTPGQRVTISCSGSSSNIGRNTLNWYQQVPGTAPKLLIYSNDERPSGVPDRF SGSKSGPSASLAISGLQSEDEADYYCAAWDDRLNGWVFGGGTKLTVL | 102 |
| 14H4 heavy | EVQLVQSGAEVKRAGESLKISCKGSGYPFATYWVGWVRQMPGKGLEWMTIIYPEDSDTRYS PSFQDHVTISADKSLSTAYLQWSSLKASDTAMYYCARVSRYYYDSRSYYPDAFDIWGQGTM VTVSS | 103 |
| 14H4 light | SYELTQPPSVSVSPGQTASITCSGDKLGDKYVCWYQQKPGRSPVLVVHQDTKRPSGIPERFS GSNSGDTATLTISGTQAMDEADYYCQAWDSTIGVFGPGTRVTVL | 104 |

TABLE C

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 1H9 | GYTFTKYG (105) | INTNTAKP (106) | ATDGSEGS (107) |
| 5C5 | GFTFSNHA (108) | LTYSGKTT (109) | AKEDYDDRGFFDF (110) |
| 1E7 | GFIFSSYG (111) | IYYDENNK (112) | ARDVVAAFDFSYGMDV (113) |
| 11B6 | GFTFSTYA (114) | ISGSGSST (115) | ARDVLYSGSYFDY (116) |
| 17A5 | GFPFSDYH (117) | ISSAGNKI (118) | ARDPGYYHGSGNKQXHGR (119) |
| 12C8 | GFSVSDSA (120) | MRSQANSYAT (121) | TR (122) |
| 2G1 | GFTVTTNY (123) | IYSAGST (124) | ARENPAQDAFDI (125) |
| 5D10 | GGSISSDY (126) | IYYSGRT (127) | ARERLDAFDM (128) |
| 1E18 | GFTFDDYA (129) | ISWNSDSI (130) | AKVRLDFWTGPMGYFQH (131) |
| 11A12 | GFSVITNY (132) | IYSGGST (133) | AHAMDDSGSYYVGLSKDPHFDS (134) |
| 1J11 | GFTVRSYG (135) | ILFDGTTK (136) | VRDFNQFVKRFVDGPAFDL (137) |
| 1A5 | GFTFSTYV (138) | I SYDGTNK (139) | AKTMDDSSGYYCPDY (140) |
| 11H12 | GFAFSGYY (141) | INSNGLT I (142) | ARDWGTTLVTFDL (143) |
| 7G12 | GYTFTNYG (144) | ISTYDGAT (145) | ARGRDSPDH (146) |
| 10H9 | GYTFISYG (147) | ISGYNGNP (148) | ARWMVGNINPFDH (149) |
| 11G1 | GYRFNTYW (150) | IYPGDLDT (151) | AREVYASTDSDYYGMDV (152) |
| 14B2 | GFSVSTRF (153) | VYKDGDT (154) | VRHGDGWNYVDS (155) |
| 12F9 | GFSFSDYY (156) | ISGSSAYT (157) | AKDYCGSGACYTADPGFFHQ (158) |

TABLE C-continued

CDR HEAVY CHAIN SEQUENCES

| Antibody | CDRH1 (SEQ ID NO:) | CDRH2 (SEQ ID NO:) | CDRH3 (SEQ ID NO:) |
|---|---|---|---|
| 15A10 | GFTFSTYA (159) | ISGSGSST (160) | CARDVLYSGSYFDYW (161) |
| 3F11 | GGSFSGFL (162) | INNSGTT (163) | ARTPVLRYLTVGP (164) |
| 13D9 | GFTFSDFY (165) | MSATGGNI (166) | ARRKFGAGSAIFDH (167) |
| 8F3 | DASIDTPSYF (168) | IYYTGNK (169) | ARYVDYVWLRAFDI (170) |
| 1A8 | DDSISTPSYF (171) | IYYTGTT (172) | ARYLDYVWLRAFDV (173) |
| 114 | GGSISSGGFF (174) | IFYTGST (175) | ARQGGVRGNYYFMDV (176) |
| 1B7 | GGSISNNY (177) | ISYSGRT (178) | ARESTYSYKLGDAFDI (179) |
| 14H4 | GYPFATYW (180) | IYPEDSDT (181) | ARVSRYYYDSRSYYPDAFDI (182) |

TABLE D

CDR LIGHT CHAIN SEQUENCES

| Antibody | CDRL1 (SEQ ID NO:) | CDRL2 (SEQ ID NO:) | CDRL3 (SEQ ID NO:) |
|---|---|---|---|
| 1H9 | QSIGTW (183) | KAS (184) | QQYNTYLGT (185) |
| 5C5 | QTISTY (186) | AAS (187) | QQGYNNPYT (188) |
| 1E7 | NKLEKF (189) | QDN (190) | QAWDGS (191) |
| 11B6 | QGIRNN (192) | AAS (193) | LQDYNYPRT (194) |
| 17A5 | SSNIGYNY (195) | DDD (196) | ST (197) |
| 12C8 | SIGSRS (198) | YDR (199) | QVWDGSSDQYV (200) |
| 2G1 | NIGSKN (201) | RDS (202) | HVWDTSTVV (203) |
| 5D10 | SSNIGSNY (204) | RNN (205) | AAWDDRLSSWV (206) |
| 1E18 | QTITSNY (207) | GAS (208) | QQYGSYRGVFT (209) |
| 11A12 | SSDVGSYNL (210) | EVT (211) | CSYAGSSISFV (212) |
| 1A5 | SLRNYF (213) | GQN (214) | NSRDSSGNHLYV (215) |
| 11H12 | SGHRGYN (216) | LEGSDSY (217) | DSRV (218) |
| 7G12 | QSINRW (219) | KAS (220) | QQYDHFPHT (221) |
| 10H9 | RNSF (222) | GQN (223) | NSRDSSGNHFYV (224) |
| 11G1 | SNDVGRSDL (225) | ESS (226) | CSYAGGNTYV (227) |
| 14B2 | HSLSSH (228) | DAS (229) | QQYNNWPLT (230) |
| 12F9 | NIGSKS (231) | YDS (232) | QVWDNTNDHPSYV (233) |
| 15A10 | QDVGKY (234) | AAS (235) | QQSSSTAAWT (236) |
| 3F11 | KLGDKS (237) | QDY (238) | QAWDRKIGQ (239) |
| 13D9 | KLGERY (240) | QTN (241) | LTWDRGTPV (242) |
| 8F3 | PSAGRF (243) | DAS (244) | QHRSNWPLT (245) |
| 1A8 | PSVGRF (246) | DAS (247) | QHRSNWPVT (248) |
| 1C14 | QSISNY (249) | AAS (250) | QQSYNTPYS (251) |
| 1B7 | SSNIGRNT (252) | SND (253) | AAWDDRLNGWV (254) |
| 14H4 | KLGDKY (255) | QDT (256) | QAWDSTIGV (257) |

TABLE 1

IgE encoding B cell frequency and hybridoma yield from helminth infected subject PBMCs.

| Subject # | Helminth Disease | Total # PBMCs cultured (× $10^5$) | Total number of IgE B cells identified | IgE B cell frequency (per $10^5$ PBMCs) | % Lysate-specific IgE B cells | # of cytofusions attempted | # IgE hybridomas obtained |
|---|---|---|---|---|---|---|---|
| 1 | Filariasis | 42 | 119 | 2.8 | 25% | 10 | 5 |
| 2 | Filariasis | 56 | 185 | 3.3 | ND | 5 | 1 |
| 3 | Strongyloidiasis | 48 | 168 | 3.5 | ND | 5 | 3 |

B cell frequencies are shown as the number of ELISA positive cultures per million PBMCs cultured. Culture supernatant was considered positive in ELISA if fluorescence value was >5 times background. ND indicates studies that were not done. Number of IgE positive B cell cultures used for cytofusion and those successful in generating IgE secreting human hybridomas are listed.

TABLE 2

Features of helminth-specific human IgE mAbs and target proteins

| IgE MAb | Subject # | Light Chain | Binding to Helminth Lysate | | | Mass Spectrometry | Phadiatop Cross-reactivity | Functional Activity |
|---|---|---|---|---|---|---|---|---|
| | | | ELISA | Western Blot | Dot Blot | | | |
| 1A5 | 1 | λ | ++ | 14 kDa band | + | Profilin family protein | $15.10_{PAU/L}$ | + |
| 10H9 | 1 | λ | − | − | − | ND | $10.30_{PAU/L}$ | + |
| 11H12 | 1 | λ | ++ | 18 kDa band | + | Cyclophilin-type peptidyl-prolyl cis-trans isomerase-2 protein | $3.03_{PAU/L}$ | + |
| 14B2 | 1 | κ | − | 13-17 kDa smear | + | ND | $15.50_{PAU/L}$ | + |
| 7G12 | 1 | κ | +++ | − | + | Phosphoglycerate kinase protein | $0.97_{PAU/L}$ | + |
| 11G1 | 2 | λ | − | − | − | ND | $2.02_{PAU/L}$ | + |
| 15A10 | 3 | κ | +++ | − | + | ND | $24.80_{PAU/L}$ | + |
| 12F9 | 3 | λ | +++ | − | + | ND | $2.48_{PAU/L}$ | + |
| 3F11 | 3 | λ | − | 18 kDa band | + | ND | $14.00_{PAU/L}$ | + |

MAb binding to lysate in ELISA:
(−) no binding detected.
(+) binding between 2-10 × background.
(++) binding between 10-100 × background.
(+++) binding >100 × background.
Approximate size of protein detected in Western blot is also noted.
MAb binding to lysate in dot blot is also shown.
If a protein target was identified using mass spectrometry it is listed.
ND = not done.
MAb cross-reactivity toward a mixture of allergens: dust mite, cat, dog, meadow grass, bermuda grass, *Alternaria*, oak tree, elm tree, ragweed, russian thistle, was assayed using ImmunoCAP Phadiatop.
This semiquantitative clinical assay used to determine the presence of IgE antibodies to common inhalant allergens in serum is considered positive if >0.35$_{PAU/L}$ (Phadia Arbitrary Units/L).
LAD2 human mast cell release of β-hexosaminidase was used for evaluating functional activity.

TABLE 3

Genetic features of helminth-specific human IgE mAbs

| IgE Mab | Light Chain | Germline Gene Segments | | | | | CDR3 AA Junction | CDR3 Length | Variable Gene Mutations | | | |
|---|---|---|---|---|---|---|---|---|---|---|---|---|
| | | VH | D | JH | VL | JL | | | VH NT | VH AA | VL NT | VL AA |
| 1A5 | λ | 3-30 | 3-22 | 3 | 3-18 | 1 | CAKTMDDSSGYYCPDYW | 15 | 12 | 9 | 8 | 7 |
| 10H9 | λ | 1-18 | 1-26 | 5 | 3-18 | 1 | CARWMVGNINPGDWW | 13 | 27 | 17 | 22 | 15 |
| 11H12 | λ | 3-11 | 4-23 | 4 | 4-80 | 3 | CARDWGTTLVTFDLW | 3 | 32 | 13 | 39 | 21 |
| 14B2 | κ | 3-83 | 5-24 | 4 | 3-15 | 4 | CVRHGDGWNYVDGLW | 13 | 39 | 19 | 15 | 7 |
| 7G12 | κ | 1-18 | 5-12 | 4 | 1-5 | 2 | CARGRDSPDHW | 9 | 35 | 19 | 24 | 15 |
| 11G1 | λ | 6-61 | 5-12 | 6 | 2-23 | 1 | CAREVYVASTDGDYYGMDVW | 13 | 40 | 19 | 27 | 17 |
| 15A10 | κ | 3-23 | 3-10 | 4 | 1-39 | 1 | CARDVLYSGSYFGYW | 13 | 19 | 9 | 30 | 15 |

TABLE 3-continued

Genetic features of helminth-specific human IgE mAbs

| IgE Mab | Light Chain | Germline Gene Segments | | | | | AA Junction | CDR3 Length | Variable Gene Mutations | | | |
|---|---|---|---|---|---|---|---|---|---|---|---|---|
| | | VH | D | JH | VL | JL | | | VH NT | VH AA | VL NT | VL AA |
| 12F9 | λ | 3-11 | 2-8 | 1 | 3-21 | 1 | CAKDYCGSGACYTADPGFFHQW | 20 | 34 | 15 | 18 | 8 |
| 3F11 | λ | 4-34 | 4-23 | 5 | 3-9 | 2 | CARTPVLRYLTVGPW | 13 | 48 | 30 | 28 | 14 |

Antibody germline gene segment usages are shown for variable (V), diverse (D), and joining (J) regions of both light and heavy chains based on imMunoGeneTics, IMGT database. The number of nucleotide and amino acid mutations are shown.
(AA Junction SEQ ID NOS: 259, 259, 260, 261, 262, 263, 264, 265, and 266 (top to bottom))

TABLE 5

Genetic features of allergen-specific human IgE mAbs

| IgE MAb | Binding Specificity | Light Chain | Germine Gene Segments | | | | | AA Junction | CDR3 Length | Variable Gene Mutations | | | |
|---|---|---|---|---|---|---|---|---|---|---|---|---|---|
| | | | VH | D | JH | VL | JL | | | VH NT | VH AA | VL NT | VL AA |
| 5C5 | Peanut, Ara h2 | κ | 3-23 | 4-17 | 4 | 1-39 | 2 | CAKEDYDDRGFFDFW | 13 | 26 | 14 | 21 | 11 |
| 1H9 | Peanut, Ara n6 | κ | 7-4 | 2-21 | 8 | 1-5 | 1 | CATDGSEGSW | 8 | 27 | 12 | 16 | 11 |
| 1E7 | Egg White, Lysozyme, Gal d4 | λ | 3-33 | 2-2 | 6 | 3-1 | 2 | CARDVVVAAFDFSYGMDVW | 17 | 18 | 8 | 15 | 11 |
| 11B6 | Egg White, Ovalbumin, Gal d2 | κ | 3-23 | 3-10 | 4 | 1-6 | 1 | CARDVLYSGSYFDYW | 13 | 21 | 10 | 12 | 6 |
| 17A5 | *Aspergillus fumigatus*, Aspf1 | λ | 3-11 | ND | ND | ND | ND | ND | ND | ND | ND | ND | ND |
| 12C8 | *Aspergillus fumigatus* | λ | 3-71 | ND | ND | ND | ND | ND | ND | ND | ND | ND | ND |
| 2G1 | Dust mite, Der p2 | λ | 3-53 | 1-14 | 3 | 3-5 | 2 | CARENPAQDAFDIW | 12 | 26 | 10 | 11 | 7 |
| 5D10 | Dust mite, Der p2 | λ | 7-4 | ND | 4 | ND | ND | ND | ND | ND | ND | ND | ND |
| 1E18 | Cat | κ | 3-9 | 3-3 | 1 | 3-20 | 3 | CAKYRLDFWTGPMGYFQMW | 17 | 12 | 7 | 9 | 7 |
| 11A12 | Cat, Fel d1 | λ | 3-65 | 6-13 | 3 | 2-23 | 1 | CARVDITATGTGGFDIW | 15 | 19 | 8 | 8 | 3 |
| 1J11 | Dog, Can f1 | λ | 3-33 | 3-3 | 3 | ND | ND | CVRDFNQFVKRFVDGPAFDLW | 19 | 25 | 17 | ND | ND |

Antibody germline gene segment usages are shown for variable (V), diverse (D), and joining (J) regions of both light and heavy chains based on imMunoGeneTics, IMGT database. The number of nucleotide and amino acid mutations are shown. ND = not determined
(AA Junction SEQ ID NOS: 267, 268, 269, 270, 270, 272, 273, and 274 (top to bottom))

TABLE 6

Sequence ID numbers for human IgE mAbs

| IgE MAb | Binding Specificity | Variable H | Variable L | HCDRs | LCDRs |
|---|---|---|---|---|---|
| 1H9 | Peanut, Ara h2 | 1 & 53 | 2 & 54 | 105-107 | 183-185 |
| 5C5 | Peanut, Ara h6 | 3 & 55 | 4 & 56 | 108-110 | 186-188 |
| 1E7 | Egg White, Lysozyme, Gal d4 | 5 & 57 | 6 & 58 | 111-113 | 189-191 |
| 11B6 | Egg White, Ovalbumin, Gal d2 | 7 & 59 | 8 & 60 | 114-116 | 192-194 |
| 17A5 | *Aspergillus fumigatus*, Asp f1 | 9 & 61 | 10 & 62 | 117-119 | 195-197 |
| 12C8 | *Aspergillus fumigatus* | 11 & 63 | 12 & 64 | 120-122 | 198-200 |
| 2G1 | Dust Mite, Der p2 | 13 & 65 | 14 & 66 | 123-125 | 201-203 |
| 5D10 | Dust Mite, Der p2 | 15 & 67 | 16 & 68 | 126-128 | 204-206 |
| 1E18 | Cat | 17 & 69 | 18 & 70 | 129-131 | 207-209 |
| 11A12 | Cat, Fel d1 | 19 & 71 | 20 & 72 | 132-134 | 210-212 |

TABLE 6-continued

Sequence ID numbers for human IgE mAbs

| IgE MAb | Binding Specificity | Variable H | Variable L | HCDRs | LCDRs |
|---|---|---|---|---|---|
| 1J11 | Dog, Can f1 | 21 & 73 | 22 & 74 | 135-137 | — |
| 1A5 | *Wuchereria bancrofti*, Profilin | 23 & 75 | 24 & 76 | 138-140 | 213-215 |
| 11H12 | *Wuchereria bancrofti*, Cyclophilin | 25 & 77 | 26 & 78 | 141-143 | 216-218 |
| 7G12 | *Wuchereria bancrofti*, Phosphoglycerate kinase | 27 & 79 | 28 & 80 | 144-146 | 219-221 |
| 10H9 | *Wuchereria bancrofti* | 29 & 81 | 30 & 82 | 147-149 | 222-224 |
| 11G1 | *Wuchereria bancrofti* | 31 & 83 | 32 & 84 | 150-152 | 225-227 |
| 14B2 | *Wuchereria bancrofti* | 33 & 85 | 34 & 86 | 153-155 | 228-230 |
| 12F9 | *Strongyloides stercoralis* | 35 & 87 | 36 & 88 | 156-158 | 231-233 |
| 15A10 | *Strongyloides stercoralis* | 37 & 89 | 38 & 90 | 159-161 | 234-236 |
| 3F11 | *Strongyloides stercoralis* | 39 & 91 | 40 & 92 | 162-164 | 237-239 |
| 13D9 | Peanut, Ara h2 | 41 & 93 | 42 & 94 | 165-167 | 240-242 |
| 8F3 | Peanut, Ara h6 | 43 & 95 | 44 & 96 | 168-170 | 243-245 |
| 1A8 | Peanut, Ara h6 | 45 & 97 | 46 & 98 | 171-173 | 246-248 |
| 1C14 | Dust mite, Der p1 | 47 & 99 | 48 & 100 | 174-176 | 249-251 |
| 1B7 | Cat, Fel d1 | 48 & 101 | 50 & 102 | 177-179 | 252-254 |
| 14H4 | *Aspergillus fumigatus*, Asp f1 | 49 & 103 | 52 & 104 | 180-182 | 255-257 |

TABLE 7

New human allergen-specific IgE mAbs.

| Human IgE mAbs | IgE mAb reactivity | Fine specificity | Allergen size (kDa) | Allergen family |
|---|---|---|---|---|
| 13D9 | Peanut | Ara h 2 | 17 | 2S albumin |
| 15A4 | Peanut | Ara h 2 | 17 | 2S albumin |
| 1A8 | Peanut | Ara h 6 | 12 | 2S albumin |
| 8F3 | Peanut | Ara h 6 | 12 | 2S albumin |
| 4G4 | Peanut | Ara h 7 | 18 | 2S albumin |
| 3B7 | Peanut | Ara h 7 | 15 | 2S albumin |
| 1C10 | Peanut | Ara h 9 | 9 | nsLTP |
| 9H7 | Walnut | Jug r 1 | 15 | 2S albumin |
| 4A7 | Cashew | Ana o 3 | 12 | 2S albumin |
| 49D12 | Cashew | Ana o 3 | 12 | 2S albumin |
| 2F5 | Cashew | Ana o 3 | 12 | 2S albumin |
| 1C14 | Dust mite | Der p 1 | 12 | Group 1 |
| 2L11 | Dust mite | Der p 1 | 12 | Group 1 |
| 1B8 | Dust mite | Der p 2 | 14 | Group 2 |
| 6A1 | Cat | Fel d 1 | 17 | Uteroglobin |
| 1B7 | Cat | Fel d 1 | 17 | Uteroglobin |
| 15H7 | Cat | Fel d 1 | 17 | Uteroglobin |
| 4F8 | *Aspergillus fumigatus* | Asp f 1 | 18 | Ribotoxin |
| 14H4 | *Aspergillus fumigatus* | Asp f 1 | 18 | Ribotoxin |

All IgE mAbs were obtained from the peripheral blood cells of subjects know to have severe peanut allergy.
Mab reactivity was determined using Phadia diagnostics and/or Western blot.
nsLTP = non-specific lipid transfer protein.

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined herein.

VII. REFERENCES

The following references, to the extent that they provide exemplary procedural or other details supplementary to those set forth herein, are specifically incorporated herein by reference.

"Antibodies: A Laboratory Manual," Cold Spring Harbor Press, Cold Spring Harbor, NY, 1988.

Abbondanzo et al., *Am. J. Pediatr. Hematol. Oncol.*, 12(4), 480-489, 1990.

Abraham et al., *Infect Immun.*; 72:810-7, 2004.

Acevedo et al., *Allergy*, 64(11):1635-43, 2009.

Achatz et al., *Science*, 276(5311):409-11, 1997.

Allred et al., *Arch. Surg.*, 125(1), 107-113, 1990.

American Academy of Allergy Asthma and Immunology: Food allergy. World-wide-web at aaaai.org/conditions-and-treatments/allergies/food-allergies.aspx Asthma and Allergy Foundation of America: Allergy facts and figures. World-wide-web at aafa.org/display.cfm?id=9&sub=30

Atherton et al., *Biol. of Reproduction*, 32, 155-171, 1985.

Avery et al., *Blood*; 112(5): 1784-93, 2008.

Brown et al., *J. Immunol. Meth.*, 12; 130(1): 111-121, 1990.

Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.

Capaldi et al., *Biochem. Biophys. Res. Comm.*, 74(2):425-433, 1977.

Chapa-Ruiz et al., *Parasite*; 8: S163-7, 2001.

Cooper et al., *J Allergy Clin Immunol.*, 111:995-1000, 2003.

Cruz et al., *Clin Exp Allergy*; 37: 197-207, 2007.

De Jager et al., *Semin. Nucl. Med.* 23(2), 165-179, 1993.

Dholakia et al., *J. Biol. Chem.*, 264, 20638-20642, 1989.

Doolittle and Ben-Zeev, *Methods Mol. Biol.*, 109:215-237, 1999.

Emsley & Cowtan, *Acta Cryst.* 60(Pt 12 Pt 1): 2126-32, 2004.

Finkelman, et al., *Immunol. Rev.*; 201: 139-155, 2004.

Food Allergy Among U.S. Children: Trends in Prevalence and Hospitalizations. world-wide-web at cdc.gov/nchs/data/databriefs/db10.htm Gefter et al., *Somatic Cell Genet.*, 3: 231-236, 1977.

Gulbis and Galand, *Hum. Pathol.* 24(12), 1271-1285, 1993.

Gurish et al., *J Immunol.*; 172: 1139-45, 2004.

Hagan et al., *Nature*, 349: 243-245, 1991.

Hagel et al., *Acta Trop.,* 103: 231-241, 2007.
Herbert et al., *Immunity;* 20: 623-635, 2004.
Johansson and Bennich, *Immunology;* 13(4): 381-94, 1967.
Karnowski et al., *Eur J Immunol,* 36(7): 1917-25, 2006.
Khatoon et al., *Ann. of Neurology,* 26, 210-219, 1989.
King et al., *J Immunol;* 158: 294-300, 1997.
King et al., *J. Biol. Chem.,* 269, 10210-10218, 1989.
Kohler and Milstein, *Eur. J. Immunol.,* 6, 511-519, 1976.
Kohler and Milstein, *Nature,* 256, 495-497, 1975.
Kyte and Doolittle, *J. Mol. Biol.,* 157(1): 105-132, 1982.
Lee et al., *J Infect Dis.,* 162:529-33, 1990.
Leonardi-Bee et al., *Am J Respir Crit Care Med.,* 174: 514-523, 2006.
Liu and Leung, *J Allergy Clin Immunol.,* 117: 1063-1066, 2006.
Lobos et al., *Mol Med.,* 2(6): 712-24, 1996.
McCarthy et al., *J Infect Dis.,* 170: 736-41, 1994.
McSharry et al., *Infect Immun;* 67: 484-489, 1999.
Mitre et al., *J Immunol;* 172: 2439-45, 2004.
Mitre and Nutman, *J Allergy Clin Immunol.,* 117(4): 939-45, 2006.
Nakamura et al., *In: Enzyme Immunoassays: Heterogeneous and Homogeneous Systems,* Chapter 27, 1987.
Nutman et al., *J. Infect. Dis.;* 160: 1042-1050, 1989.
Olsson and Kaplan, *Proc Natl Acad Sci USA;* 77(9): 5429-31, 1980.
O'Shannessy et al., *J. Immun. Meth.,* 99, 153-161, 1987.
Persic et al., *Gene* 187:1, 1997.
Potter and Haley, *Meth. Enzymol.,* 91, 613-633, 1983.
Remington's Pharmaceutical Sciences, 15th Ed., 3: 624-652, 1990.
Renz et al., *J Immunol.;* 145(11): 3641-6, 1990.
Rodrigues et al., *Clin Exp Allergy;* 38: 1769-1777, 2008.
Santiago et al., *J Immunol.,* 194(1): 93-100, 2015.
Santiago et al., *J Allergy Clin Immunol.,* 130(1): 248-56, 2012.
Santiago et al., *PLoS One,* 7(7): e40552, 2012.
Sicherer et al., *J Allergy Clin Immunol., April;* 103(4):559-62, 1999.
Steel, *J Infect Dis.,* 164:581-7, 1991.
Strachan, *BMJ,* 299:1259-1260, 1989.
Tang et al., *J. Biol. Chem.,* 271:28324-28330, 1996.
Turner et al., *J Infect Dis.,* 188:1768-1775, 2003.
Turner et al., *Microbes Infect.,* 7:990-996, 2005.
U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
van den Biggelaar et al., Lancet.; 356:1723-1727, 2000.
Voehringer et al., J. Exp. Med., 203:1435-1446, 2006.
Wawrzynczak & Thorpe, In: *Immunoconjugates, Antibody Conuugates In Radioimaging And Therapy Of Cancer,* Vogel (Ed.), NY, Oxford University Press, 28, 1987.
Wordemann et al., Trop Med Int Health.; 13:180-186, 2008.

What is claimed is:

1. A method of treating a dust mite-related allergic reaction in a subject comprising delivering to said subject an IgG antibody or antibody fragment, wherein said antibody or antibody fragment comprises heavy chain CDR1 SEQ ID NO: 123, heavy chain CDR2 SEQ ID NO: 124, heavy chain CDR3 SEQ ID NO: 125, light chain CDR1 SEQ ID NO: 201, light chain CDR2 SEQ ID NO: 202, and light chain CDR3 SEQ ID NO: 203.

2. The method of claim 1, wherein the antibody or antibody fragment is encoded by clone paired heavy and light chain variable nucleic acid sequences as set forth in SEQ ID NO: 13 and SEQ ID NO: 14.

3. The method of claim 1, wherein said antibody or antibody fragment is encoded by clone paired heavy and light chain variable nucleic acid sequences having 70%, 80%, or 90% identity to heavy and light chain variable nucleic acid sequences as set forth in SEQ ID NO: 13 and SEQ ID NO: 14.

4. The method of claim 1, wherein said antibody or antibody fragment is encoded by clone paired heavy and light chain variable nucleic acid sequences having 95% identity to heavy and light chain variable nucleic acid sequences as set forth in SEQ ID NO: 13 and SEQ ID NO: 14.

5. The method of claim 1, wherein said antibody or antibody fragment comprises clone paired heavy and light chain variable sequences as set forth in SEQ ID NO: 65 and SEQ ID NO: 66.

6. The method of claim 1, wherein said antibody or antibody fragment comprises clone paired heavy and light chain variable sequences having 70%, 80%, or 90% identity to heavy and light chain variable sequences as set forth in SEQ ID NO: 65 and SEQ ID NO: 66.

7. The method of claim 1, wherein said antibody or antibody fragment comprises clone paired heavy and light chain variable sequences having 95% identity to heavy and light chain variable sequences as set forth in SEQ ID NO: 65 and SEQ ID NO: 66.

8. The method of claim 1, wherein said antibody or antibody fragment is a recombinant scFv (single chain fragment variable) antibody, chimeric antibody, Fab fragment, F(ab')2 fragment, or a Fv fragment.

9. The method of claim 1, further comprising treating said subject with an anti-inflammatory agent.

10. The method of claim 9, wherein said anti-inflammatory agent is selected from the group consisting of a steroid, an anti-histamine, and anti-leukotriene.

11. The method of claim 9, wherein said anti-inflammatory agent is administered chronically.

* * * * *

SEQUENCE LISTING

```
<160> NUMBER OF SEQ ID NOS: 275

<210> SEQ ID NO 1
<211> LENGTH: 351
<212> TYPE: DNA
<213> ORGANISM: Artificial sequence
<220> FEATURE:
<223> OTHER INFORMATION: Synthetic oligonucleotide

<400> SEQUENCE: 1
gaattccagt tggtgcaatc tgggtctgag ttgaggaagc ctggggcctc agtgaaggtt      60
tcctgcaagg cttccggata caccttcact aagtatggta tgaattgggt gcgacaggcc     120
cctggacaag gactggagtg gatgggatgg attaacacga acactgcaaa gccaacgtat     180
gcccaggact tcacaggacg atttgtcttc tctttggaca cctctgtcaa cacggcatat     240
ctggagatca gcggcctaaa ggctgaagac accgccgtct attactgtgc gacagatggt     300
agtgagggct cctggggcca gggaaccacg gtcaccgtct ccgcaagctt c              351

<210> SEQ ID NO 2
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 2
```

```
agatctgaca tccagatgac ccagtctcct tccaccctgt ttgcatctgt aggagacaga    60
gtcaccatca cttgccgggc cagtcagagt attggtacct ggttggcctg gcatcagcag   120
aaaccaggga cagcccctaa ggtcctgatc tataaggcgt ctaatttaaa aagtggggtc   180
ccatctagat ttagcggcag tggatctggg acagacttca ctctcaccat cagcagcctg   240
cagcctgatg atgttgcaac ttattactgt caacaatata atacttactt ggggacgttc   300
ggccaaggga cccgggtgga gatcaaaact gcggccgca                          339
```

```
<210> SEQ ID NO 3
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 3
gaattccagt tgttggagtc agggggaggc ttggtacagc cggggggggtc cctgagactc    60 tcctgtgcag cctctggatt cacctttagc aaccatgcca tgagctgggt ccgccagact   120
ccaggggagg ggctgcagtg ggtctcagct cttacttata gtggtaagac cacatactac   180
gcagactccg tgaagggccg gttcaccatc tccagagaca attccaagaa tttactattt   240
ctgcaaatga acagcctgag agccggggac acggccatat attactgtgc gaaggaggac   300
tacgatgacc ggggcttctt tgacttctgg ggccaaggga caagggtcac cgtctcctca   360
gcaagcttc                                                           369
```

```
<210> SEQ ID NO 4
<211> LENGTH: 339
<212> TYPE: DNA
<213> ORGANISM: Artificial sequence
<220> FEATURE:
<223> OTHER INFORMATION: Synthetic oligonucleotide

<400> SEQUENCE: 4
agatctgaca tccagatgac ccagtctcca tcctccctgt ctgcgtctgt gggagacaga    60
gtcaccatca cttgccgggc aagtcagacc attagtactt atttacattg gtatcaacaa   120
aaaccaggca aagcccctaa cctcctcatc tatgctgcat ccactttgca aagtggggtc   180
ccatcaaggt tcagtggcag tggatctggg acagatttca gtctcaccat cagtagtctg   240
cgtcctgaag attttgcaat ttactactgt caacagggtt acaataaccc gtacactttt   300
ggccagggga ccaaagtgga tatcaaaact gcggccgca                          339
```

```
<210> SEQ ID NO 5
<211> LENGTH: 378
<212> TYPE: DNA
<213> ORGANISM: Artificial sequence
<220> FEATURE:
<223> OTHER INFORMATION: Synthetic oligonucleotide

<400> SEQUENCE: 5
gaattccagt tggtggagac tggggggaggc gtggtccagc ctgggaggtc cctgagactc    60
tcgtgtgcag cgtctggatt catcttcagt agttacggaa tgcactgggt ccgccaggct   120
ccaggcaagg ggctggagtg ggtggcagtt atatattatg atgaaaataa taaatattat   180
gcagactccg tgaagggccg attcaccatc tccagagaca attccaagaa cacgctctct   240
ctgcaaatga acagcctgag agccgacgac acggctgtat attactgtgc gagagatgta   300
gtagtagctg cttttgactt ctcctacggt atggacgtct ggggccaagg gaccacggtc   360
```

```
accgtctccg caagcttc                                                    378
```

```
<210> SEQ ID NO 6
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 6
gaattctcct atgacctgac tcagccaccc tcagtgtccg tgtccccagg acagacagcc       60
aacatcacct gctctggcaa taaactggaa aaatttggtt gctggtatca gcagaagccg      120
ggccagtccc ctcttctggt catctatcaa gataacaagc ggccctcagg gatccctgag      180
cgattctctg gctccaactc tgagaacaca gccactctga ccatcagcgg gacccaggct      240
ctggatgagg ctgactatta ctgtcaggcg tgggacggca gcttcggcgg agggaccaag      300
ctgacagtcc taagcttgcc c                                                321
```

```
<210> SEQ ID NO 7
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 7
gaattccagc tgttggagtc tgggggaggc ttggtacagc ccggagggtc cctgagactc       60
tcctgtgcag cctctggatt cacctttagc acttatgcca tgagctgggt ccgccaggct      120
ccagggaagg ggctggagtg ggtctcaact attagtggta gcgggagcag cacatacgac      180
gcagactccg tgaagggccg gttcaccatc tccagagaca aattcaaaag cacggtgtat      240
ttgcaaatga atagcctgag agccgaggac acggccgtat attactgtgc gagagatgtt      300
ctctactcgg ggagttactt tgactactgg gccaggaaca caatggtcac cgtctcttca      360
gcaagcttc                                                              369
```

```
<210> SEQ ID NO 8
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 8
agatctcaga tgacccagtc tccatcgtcc ctgtctgcat ctataggaga cagagtcacc       60
atcacttgcc gggcaagtca gggcattaga aataatttag␣gctggtatca gcagacacca      120
gggaaagccc ctaggctcct gatctatgct gcatccagtt tacaaagtga cgtcccatca      180
aggttcagcg gcagtgggtc tggcacagat ttcactctca ccatcagcgc cctgcagcct      240
gaagattttg caacttatta ctgtctacaa gactacaatt accctcggac gttcggccaa      300
gggaccaagg tggaaatcaa aactgcggcc gca                                   333
```

```
<210> SEQ ID NO 9
<211> LENGTH: 330
<212> TYPE: DNA
<213> ORGANISM: Artificial sequence
<220> FEATURE:
<223> OTHER INFORMATION: Synthetic oligonucleotide
<220> FEATURE:
```

```
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (9)..(10)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 9
gaagngcann tggtggagtn tggggagggg ttggtcaagc ctggggggtc cctgagactc      60
tcctgtgcag cctctggatt cccttcagt  gattatcaca tgacctggat ccgccaggct     120
ccggggaagg ggctggaatg gatttcacac atcagtagtg ctggcaataa gatacattac     180
gcagagtctg tgaagggccg gttcaccata tccaggggaca acgccaagaa ttctttgttt    240
ttgcacatga acagcctgag agccgaggac acggccatgt attactgtgc cagagatccg    300
ggatattatc atggttcggg gaataagcaa                                     330

<210> SEQ ID NO 10
<211> LENGTH: 275
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (190)..(192)
<223> OTHER INFORMATION: n is a, c, g, or t

<400> SEQUENCE: 10
cagtctgtgt tgacgcagcc gccctcagtg tctgcggccc caggacagag ggtcaccatc      60
tcctgctctg gcggcagttc caacattggt tataattatg tggcctggta ccagcaattc     120
ccaggaacag ccccccaaact cctcctctat gacgatgatg agcggccctc tgnccttcac    180
aaacaagttn nncaccatcg cctggaggat gcttcttctc accctcctca ttcaggccac     240
agggtcctgg gcccagtctg ccctgactca acctg                                275

<210> SEQ ID NO 11
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 11
gaagtgcagc tggtggagtc tggggaggc ttggtccagc cggggggtc  cctgaaactc       60 tcctgtgcag tctctgggtt cagcgtcagt gactctgcta tacactgggt ccgccaggct     120
tccgggaaag gactggagtg ggtaggccac atgcgaagtc aggcgaacag ttacgcgaca     180
gcctatggtg cgtcggtgag aggcaggttc aacatctcca gagatgactc aaagaacacg    240
gcatatctgc aaatgaacag cctgaacatc gatgacacgg ccgtatatta ttgtactaga    300
aaggtggata tcgacacgg aatggacgtc tgggccaagg accacgtc                  348

<210> SEQ ID NO 12
<211> LENGTH: 324
```

<212> TYPE: DNA
<213> ORGANISM: Artificial sequence
<220> FEATURE:
<223> OTHER INFORMATION: Synthetic oligonucleotide

<400> SEQUENCE: 12

```
tcctatgtgt tgacgcagcc tccctctgtg tcagtggccc caggacagac ggccaggatt    60
ccctgtgggg gaaacagcat tgggagtaga agtgtgcact ggtaccagca gaagccaggc   120
cgggcccctg tgttggtcat ctattatgat agggaccggc cctcgggat ccctgagcga    180
ttctctggct ccaactctgg gaacacggcc accctgacca tcgacagggt cgaggccggg   240
gatgaggccg actactactg tcaggtgtgg gatggtagta cgaccaata tgtcttcgga    300
attgggacca aggtcaccgt ccta                                          324
```

<210> SEQ ID NO 13
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 13

```
gaattccagc tggtggagtc tggaggaggc ttgatccagc ctggggggtc cctgagactc    60
tcctgtgcag gctctgggtt caccgtcact accaactaca tggcctgggt ccgccaggct   120
ccagggaagg ggctggagtg ggtctcaact atttatagcg ctggtagcac attttatgcg   180
gactccgtga agggccgatt caccatctcc ggagacaatt ccaagaacac gctgtatctt   240
caaatgggta gcctgagagc cgaggacacg gccgtctatt actgtgcgag agaaaaccct   300
gcccaggatg cttttgatat ctgggccaag gacacaatgg tcaccgtctc ttcagcaagc   360
ttc                                                                 363
```

<210> SEQ ID NO 14
<211> LENGTH: 651
<212> TYPE: DNA
<213> ORGANISM: Artificial sequence
<220> FEATURE:
<223> OTHER INFORMATION: Synthetic oligonucleotide

<400> SEQUENCE: 14

```
gaattctcct atgagttgac tcagccactc tcagtgtcag tggccctggg acagacggcc    60
aggattacct gtgggggaaa caacattgga agtaaaaatg ttcactggta ccagcaaaag   120
ccaggcctgg cccctgtgct ggtcatctat agggatagca accggccctc tgggatccct   180
gcgcgattct ctggctccag ctcggggaac acggccaccc tgaccatcag cagcgcccaa   240
gccgggatg aggctgacta ttactgtcat gtgtgggaca ccagcactgt ggtattcggc    300
ggagggacta aactgacagt cctaagcttg cccaaagccg ctccttccgt gactctgttt   360
ccccctagtt cagaggaact gcaggccaac aaggctacac tggtctgtct gatttctgac   420
ttctatcctg ggccgtgac tgtcgcatgg aaggccgata gctcccagt gaaagctggc     480
gtcgagacca caactccctc taagcagagt aacaacaagt atgcagcctc tagttacctg   540
tctctgaccc cagaacagtg gaagagtcac aaaagctact cctgtcaggt cacccacgaa   600
ggcagcaccg tcgagaaaac agtcgcaccc accgagtgta gctgactcga g            651
```

<210> SEQ ID NO 15
<211> LENGTH: 349
<212> TYPE: DNA

<213> ORGANISM: Artificial sequence
<220> FEATURE:
<223> OTHER INFORMATION: Synthetic oligonucleotide

<400> SEQUENCE: 15

```
caggtgcagc tgcaggagtc gggcccagga ctggtgaagc cttcggagac cctgtccctc    60
acctgcactg tctctggtgg ctccatcagt agtgactact ggagctggat tcggcagccc   120
ccagggaagg gactggagtg gattgggtac atctattata gtgggaggac ctactacaac   180
ccctctttca agagtcgagt cgccatatca ctagacacgt ccaagatcca gttttccctg   240
aacctgacct ctgtgaccgc tgcggacacg gccgtttatt actgtgcgag agagcgccta   300
gacgcttttg atatgtgggg ccaggggaca gtggtcttcg tctcttcag               349
```

<210> SEQ ID NO 16
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 16

```
cagtctgtgc tgactcagcc accctcagcg tctgggaccc ccgggcagag ggtcaccatc    60
tcttgttctg gaggcagctc caacatcgga agtaattatg tatactggta ccagcggctc   120
ccaggaacgg cccccaaact cctcatctat aggaataatc agcggccctc aggggtccct   180
gaccgattct ctggctccaa gtctggcacc tcagcctccc cggccatcag tgggctccgg   240
tccgaggatg aggctgatta tttctgtgca gcatgggatg acaggttgag tagttgggtt   300
ttcggcgaag ggaccaagct gaccgtccta g                                  331
```

<210> SEQ ID NO 17
<211> LENGTH: 390
<212> TYPE: DNA
<213> ORGANISM: Artificial sequence
<220> FEATURE:
<223> OTHER INFORMATION: Synthetic oligonucleotide

<400> SEQUENCE: 17

```
gtcctgtgtc aggtgcagct ggtgcagtcg gggggaggct tggtacagcc tggcaggtcc    60
ctgagactct cctgtgcagc ctctggattc acctttgatg attatgccat gcactgggtc   120
cggcaagctc cagggaaggg cctggagtgg gtctcaggta ttagttggaa tagtgatagt   180
atagcctatg cggactctgt gaagggccga ttcaccatct ccagagacaa caccaagaac   240
tccttgtatc tggaaatgaa cagtctgaga cctgaggaca cggccttgta ttactgcgca   300
aaagttcgtc tggattttg  gactggtccg atggggtact ccagcactg  gggccggggc   360
accctggtca ccgtctcctc agcaagcttc                                    390
```

<210> SEQ ID NO 18
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 18

```
gaaattgtgt tgacgcagtc tccaggcacc ctgtctttgt ctccagggga aagagccacc    60
ctctcctgca gggccagtca gactattacc agcaactatt tagcctggta ccagcagaaa   120
cctggccagg ctcccaggct cctcatctat ggtgcctcca ccagggccac tggcatccca   180
```

```
gacaggttca gtggcagtgg gtctgggaca gacttcactc tcaccatcaa cagactggag    240
cctgaagatt ttgcactgta ttactgtcag cagtatggta gctaccgggg ggtattcact    300
ttcggccctg ggaccaaagt ggatatcaaa cgaactgcgg ccgcaccatc tgtcttcatc    360
ttcccgcca                                                             369

<210> SEQ ID NO 19
<211> LENGTH: 372
<212> TYPE: DNA
<213> ORGANISM: Artificial sequence
<220> FEATURE:
<223> OTHER INFORMATION: Synthetic oligonucleotide

<400> SEQUENCE: 19
gaattccagc tggtggagtc tgggggaggc ttcgtccagc ctgggggtc cctgagactc      60 tcctgtgccg cctctggatt cagcgtcatt accaattaca tgtcctgggt ccgccaggct    120
ccaggaaagg ggctggagtg gtctcactt atttatagcg gtggtagcac atactacgca     180
gactccgtga agggccgatt caccctctcc agagacaatt ccaagaatac gctaaatctt    240
caaatgaaca gcctgagagc tgaggacacg gctgtctact actgtgcgag agttgatata    300
acagcaactg gtacgggtgg ttttgatatc tgggccaagg acacaatggt caccgtctct    360
tcagcaagct tc                                                         372

<210> SEQ ID NO 20
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 20
gaattccagt ctgccctgac tcaacctgcc tccgtgtctg ggtctcctgg ccagtcgatc     60
accctctcct gcactggaac cagcagtgat gttgggagtt ataaccttgt ctcatggtac    120
caacaacacc caggcaaagc ccccaaactc atgatttatg aggtcactaa gcggccctca    180
ggggtttcta atcgcttctc tggctccaag tctggcaaca cggcctccct gacaatctct    240
gggctccagg ctgaggacga ggctgattat tactgttgct catatgcagg tagtagcatt    300
tcctttgtct tcggaactgg gaccaaggtc acagtcctaa gcttg                    345

<210> SEQ ID NO 21
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 21
gaattccagt ctgccctgac tcaacctgcc tccgtgtctg ggtctcctgg ccagtcgatc     60
accctctcct gcactggaac cagcagtgat gttgggagtt ataaccttgt ctcatggtac    120
caacaacacc caggcaaagc ccccaaactc atgatttatg aggtcactaa gcggccctca    180
ggggtttcta atcgcttctc tggctccaag tctggcaaca cggcctccct gacaatctct    240
gggctccagg ctgaggacga ggctgattat tactgttgct catatgcagg tagtagcatt    300
tcctttgtct tcggaactgg gaccaaggtc acagtcctaa gcttg                    345

<210> SEQ ID NO 22
```

<400> SEQUENCE: 22

000

<210> SEQ ID NO 23
<211> LENGTH: 336
<212> TYPE: DNA
<213> ORGANISM: Artificial sequence
<220> FEATURE:
<223> OTHER INFORMATION: Synthetic oligonucleotide

<400> SEQUENCE: 23

```
gaagtgcagc tggtggagtc tgggggaggc gtggtccagc ctgggaggtc cctgagactc      60
tcctgtgcag gctctggatt caccttcagt acctatgtca tgcactgggt ccgccaggct     120
ccaggcaagg ggctggagtg ggtggcagtt atatcatatg atggaactaa taaatactat     180
gcagactcca tgaagggccg attcaccatc tccagagaca attccaagaa cacgctgtat     240
ctgcaactga accgcctgag agctgaggac acggctgtgt attactgtgc gaaaacaatg     300
gatgatagta gtggttatta ttgtcctgat tactgg                               336
```

<210> SEQ ID NO 24
<211> LENGTH: 305
<212> TYPE: DNA
<213> ORGANISM: Artificial sequence
<220> FEATURE:
<223> OTHER INFORMATION: Synthetic oligonucleotide

<400> SEQUENCE: 24

```
tcttctgagc tgactcagga ccctgctgtg tctgtggcct tgggacagac agtcaagatc      60
acatgccaag agacagcct cagaaactat tttgcaaact ggtaccagca gaagccagga     120
caggcccctg ttcttgtcat ctatggtcaa acaaccggc cctcagggat cccagaccga     180
ttctctggct ccacctcagg aaacacaggt tccttgacca tcactgggc tcaggcggaa     240 gatgaggctg actattactg taactcccgg gacagcagtg gtaaccatct ttatgtcttc     300
ggaac                                                                  305
```

<210> SEQ ID NO 25
<211> LENGTH: 360
<212> TYPE: DNA
<213> ORGANISM: Artificial sequence
<220> FEATURE:
<223> OTHER INFORMATION: Synthetic oligonucleotide

<400> SEQUENCE: 25

```
caggtccaac tggtggagtc tgggggagac ttggtcacgc ctggagggtc cctgagactg      60
tcgtgtgcag cctcgggatt cgcctttagc ggctactaca tgagttggat ccgccaggct     120
ccagggaagg ggctggaatg gatctcatac attaatagta cggtcttac catctcctac     180 gcggactctg tgaagggccg attcaccgtc tccagggaca atgccaagaa ctcactgttt     240
ctgcaaatga gctccctgag agccgaggac acggccatat attactgtgc gcgagattgg     300
```

```
gggacaacat tggtaacttt tgacctctgg ggccagggaa ccctggtcac cgtctcctca    360
```

<210> SEQ ID NO 26
<211> LENGTH: 318
<212> TYPE: DNA
<213> ORGANISM: Artificial sequence
<220> FEATURE:
<223> OTHER INFORMATION: Synthetic oligonucleotide

<400> SEQUENCE: 26

```
cagcctgtgc tgactcaatc atcctctgcc tctgcttcca tgggatcctc ggccaagctc     60
acctgtactc tgagtagtgg ccacagaggc tacaacatcg cttggcttca gcagcatcca    120
gggaaggccc ctctctattt gacgaatctt gagggtagtg actcctacaa gaacgatcgc    180
ctcacagtct ccagctctgg ggctgaccgc tacctcacca tctccaacct ccagcctgaa    240
gatgaggcta cctattactg cttcacctgg gacagcgact cccgcgtctt cggcgggggg    300
acgcacctga ccgtcctg                                                  318
```

<210> SEQ ID NO 27
<211> LENGTH: 348
<212> TYPE: DNA
<213> ORGANISM: Artificial sequence
<220> FEATURE:
<223> OTHER INFORMATION: Synthetic oligonucleotide

<400> SEQUENCE: 27

```
caggttcact ggtgcagtc tggagttgac gtgaagaagc ctggggcctc agtgaaactc      60
tcctgcaaga cttctggtta caccttact aattatggta ttacttgggt gcgacaggcc    120
cctggacaag gcttgagtg gatgggctgg atcagcactt acgatggtgc cacaaactat    180
agccagaatc tccagggcag aatcatcatg accactgaca catccaagag acagcctat    240
ctgcagatga ggagtctgag atctgacgac acggccgtct attactgtgc gaggggacga    300
gatagtccgg accactgggg ccagggaacc ctggtcaccg tctcctca                 348
```

<210> SEQ ID NO 28
<211> LENGTH: 321
<212> TYPE: DNA
<213> ORGANISM: Artificial sequence
<220> FEATURE:
<223> OTHER INFORMATION: Synthetic oligonucleotide

<400> SEQUENCE: 28

```
gacatccaga tgacccagtc tccttccacc ctgtctgcat ctgtaggaga cagagtcacc     60
atcacttgcc gggccagtca gagtattaat aggtggttgg cctggtatca gcagaaacca    120
gggacagccc ctaaactcct catctttaag gcgtctactc tagacagtgg tgtcccagcg    180
aggttcagcg gcactggatc tgagacagaa ttctctctga ccatcaacag cctgcagcct    240
gatgattttg caacttatta ctgccaacag tatgatcatt ttccgcacac ttttggcccg    300
gggaccaaac tggacatcaa a                                              321
```

<210> SEQ ID NO 29
<211> LENGTH: 333
<212> TYPE: DNA
<213> ORGANISM: Artificial sequence
<220> FEATURE:
<223> OTHER INFORMATION: Synthetic oligonucleotide

<400> SEQUENCE: 29

```
caggtgcagc tggtacagtc tggaactgag gtgaaaaagc ctggggcctc agtgaaggtc     60
```

```
tcctgcaaga cttctggtta cacctttatc agttatggtg tcacctgggt gcgacaggcc    120
cctggacaag ggcttgagtg gatgggatgg atcagcggtt acaatggtaa cccaaaatat    180
gcagagaagt tccacgacag aataaccatg accacagaca gatcgacgaa cacagtctac    240
ttggaattga ggagcctgag atctgacgac acggccgtgt attactgtgc gagatggatg    300
gtgggaaata ttaacccctt tgaccactgg gcc                                 333

<210> SEQ ID NO 30
<211> LENGTH: 249
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (19)..(19)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (43)..(43)
<223> OTHER INFORMATION: n is a, c, g, or t
<220> FEATURE:
<221> NAME/KEY: misc_feature
<222> LOCATION: (56)..(57)
<223> OTHER INFORMATION: n is a, c, g, or t
<220> FEATURE:
<221> NAME/KEY: misc_feature
<222> LOCATION: (59)..(60)
<223> OTHER INFORMATION: n is a, c, g, or t
<220> FEATURE:
<221> NAME/KEY: misc_feature
<222> LOCATION: (62)..(62)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (84)..(84)
<223> OTHER INFORMATION: n is a, c, g, or t
<220> FEATURE:
<221> NAME/KEY: misc_feature
<222> LOCATION: (131)..(131)
<223> OTHER INFORMATION: n is a, c, g, or t
<220> FEATURE:
<221> NAME/KEY: misc_feature
<222> LOCATION: (151)..(151)
<223> OTHER INFORMATION: n is a, c, g, or t

<400> SEQUENCE: 30
tcagaaactc atttggaanc tggtacaagc agacgccang acnagttcct gttctnntnn    60
tntatggtca aaacanccgg cccncagtga tcccagaccg attctctggc tccacctcag   120
gaaacaccgg ntccttgacc atcactgggg ntcaggcgga agatgaggat gattattact   180
gtaactcccg ggacagcagt ggtaaccatt tttatgtctt cggaactggg accaaggtca   240
ccgtcctag                                                           249

<210> SEQ ID NO 31
<211> LENGTH: 357
<212> TYPE: DNA
<213> ORGANISM: Artificial sequence
<220> FEATURE:
<223> OTHER INFORMATION: Synthetic oligonucleotide
```

<400> SEQUENCE: 31

```
ggaggtgcag gtgggccagt ctggaccagt gctaaaaaag ccggggggagt ctatgaagat    60
ctccggtagg gggtcgggat acaggttcaa cacttattgg gtcgcctggg tgcgccagat   120
gcccgggaaa ggtctggagt ggatgggaat gatctatccg ggtgacttgg atacgaaata   180
tagtccgtcc ttccaaggcc aagtcaccat ttcagccgac aagtccagca ataccgccta   240
cctacagtgg agtagtctga aggcctcgga caccgccatg tattattgtg cgagagaagt   300
atatgtggct tcgactgata gtgactatta cggtatggac gtctgggcct aggacca     357
```

<210> SEQ ID NO 32
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 32

```
cagtctgccc tgactcagcc tgcctccgtg tctgggtctc ctggacagtc gatcaccatc    60
tcctgcactg gaaccagcaa tgatgttggg cgttctgacc ttgtcgcctg gtaccaacaa   120
caccccgaca aggcccccag actcattatt tatgagtcca gtaagcggcc ctcagggtt    180
tctgcccgct tctctggctc caggtctggc atcacggcct ccctgacaat ctctgacctc   240
caggctgaag acgaggctga ctattactgc tgttcatatg caggtggtaa cacttatgtc   300
ttcggcaccg cgaccggggt caccgtccta g                                  331
```

<210> SEQ ID NO 33
<211> LENGTH: 334
<212> TYPE: DNA
<213> ORGANISM: Artificial sequence
<220> FEATURE:
<223> OTHER INFORMATION: Synthetic oligonucleotide

<400> SEQUENCE: 33

```
gaagtgcagc tggtggagac tggaggaggc ttgattcagc cggggggggtc cctgcgactc    60
tcctgtgcag cctctgggtt cagcgtcagt acgaggttca tgagctgggt ccgccaggct   120
ccaggtcagg gactggagtg ggtctcagtc gtctataaag atggtgacac cttcaactcg   180
gactccgtga agggccgatt cagcatctcc agagacaatt ccaagaacac agtgtttctt   240
caaatgaaca gactgagagt cgaagacact gccgtatact tctgtgtgcg acatggcgat   300
ggttggaatt acgtcgactc ctggggcctg gaac                               334
```

<210> SEQ ID NO 34
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 34

```
gaaatagtga tgacgcagtc tccagccacc ctgtctgtgt ctccagggga aggagccacc    60
ctctcctgca gggccagtca cagtcttagt agtcacttag cctggtacca gcaaaaacct   120
ggccaggctc ccaggctcct aatatatgat gcatccgtca gggccactga tatcccagcc   180
aggttcagtg gcagtgggtc tgggacagag ttcactctca ccatcagcag cctgcagtct   240
gaagattttg cagtttacta ctgtcagcaa tataataact ggccgctcac tttcggcgga   300
gggaccaagc tggagatcaa ac                                            322
```

<210> SEQ ID NO 35
<211> LENGTH: 357
<212> TYPE: DNA
<213> ORGANISM: Artificial sequence
<220> FEATURE:
<223> OTHER INFORMATION: Synthetic oligonucleotide

<400> SEQUENCE: 35

```
gaagtgcagc tggtggagtc tgggggagac ttggtcaagc ctggagggtc cctgagaatc      60
tcctgtgcag cctctggatt cagcttcagt gactactaca tgagttggat ccgccaggct     120
ccagggaagg ggcttgaatg ggttgcgtat attagtggat ccagtgccta cacaagctac     180
gcggactctg tgaagggccg cttctccatc tccagagaca cgccaacaa ctcactcttt      240 ctacaaatga acagcctgag agccgaggac acggctacat atttctgtgc gaaagattac     300
tgtggcagtg gcgcctgcta cactgcggac cctggcttct tccatcaatg ggccagg       357
```

<210> SEQ ID NO 36
<211> LENGTH: 331
<212> TYPE: DNA
<213> ORGANISM: Artificial sequence
<220> FEATURE:
<223> OTHER INFORMATION: Synthetic oligonucleotide
<220> FEATURE:
<221> NAME/KEY: misc_feature
<222> LOCATION: (325)..(325)
<223> OTHER INFORMATION: n is a, c, g, or t

<400> SEQUENCE: 36

```
tcctatgttc tgactcagcc gccctcagtg tcggtggccc caggaaagac ggccacgatt      60
tcctgtgggg gaaacaacat tggaagtaaa agtgtgcact ggtatcagca gaagccaggc     120
caggccccta tagtggtcat ctattatgat agcgaccggc cctcagggat ccctgagcga     180
ttttctggaa tcaattctgg gaacacggcc accctgacca tcagcagggt cgaagccggg     240
gatgaggccg actattattg tcaggtgtgg gacaatacta atgatcatcc ctcttatgtc     300
ttcggagctg ggaccaaggt caccntccta g                                     331
```

<210> SEQ ID NO 37
<211> LENGTH: 316
<212> TYPE: DNA
<213> ORGANISM: Artificial sequence
<220> FEATURE:
<223> OTHER INFORMATION: Synthetic oligonucleotide

<400> SEQUENCE: 37

```
gaagtgcagc tgttggagtc tgggggaggc ttggtacagc ccggagggtc cctgagactc      60
tcctgtgcag cctctggatt cacctttagc acttatgcca tgagctgggt ccgccaggct     120
ccagggaagg ggctggagtg ggtctcaact attagtggta gcgggagcag cacatacgac     180
gcagactccg tgaagggccg gttcaccatc tccagagaca aattcaaaag cacggtgtat     240
ttgcaaatga atagcctgag agccgaggac acggccgtat attactgtgc gagagatgtt     300
ctctactcgg ggagtt                                                      316
```

<210> SEQ ID NO 38
<211> LENGTH: 326
<212> TYPE: DNA
<213> ORGANISM: Artificial sequence
<220> FEATURE:
<223> OTHER INFORMATION: Synthetic oligonucleotide

```
<400> SEQUENCE: 38
gacatccaaa tgacccagtc tccatcctcc ctgtctgcat ctgtaggaga cagagtcact      60
atctcttgcc gggcaagtca ggacgttggc aaatatttaa attggtatca acagaaacca     120
ggggaagccc ctaaactcct gatctatgca gcatctcgtt tagatagggg agtctcgtca     180
aggttcagtg gcagtggaat cggggcagac ttcactctca ccatcagcgg tctgcaacct     240
gaagattttg caacttacta ctgtcaacag agttccagta ccgctgcgtg gacgttcggc     300
caagggacca aggtggaaat caaaag                                          326

<210> SEQ ID NO 39
<211> LENGTH: 342
<212> TYPE: DNA
<213> ORGANISM: Artificial sequence
<220> FEATURE:
<223> OTHER INFORMATION: Synthetic oligonucleotide

<400> SEQUENCE: 39
cagctgcaga agcagcagtg ggccgcagga ctgaagcatc cgtcggcgac cctctccttc      60
atatgcggta tcaatggtgg ttccttcagt ggtttcttgc ggacatggat ccgccagtcc     120
ccagggaagg gggtggaatt gattggagaa atcaataata gtggcaccac caaatacaat     180
tcgtccctca agagtcgact caccatatca atagacacgt ccaaggacca ggtctcccta     240
cagttgcgct ctgtgaccgc cgcggacacg gctacatatt tctgtgcgag aactcctgtc     300
ctccgatatt tgacagttgg gccatggggc agggaaccc tg                         342

<210> SEQ ID NO 40
<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 40
tcctatgagc tgactcagcc accctcagtg tccctgtccc cggacagac agccaccatc       60 acatgctcgg gagataaaatt gggggataaa tctgtttcct ggtatcaaca gatgccaggc    120
cagtccccca tttttggtcat ctatcaagat tacaaacggc cctcaggaat ctctgagcga    180
ttctctggct ccaactctgg gaacacagcc actctgacca tcagcgagac ccaggctatg    240
gatgaggctg actattactg tcaggcgtgg gacaggaaga ttgggcaatt tggcggaggg    300
accaagatga ccgtcatag                                                  319

<210> SEQ ID NO 41
<211> LENGTH: 364
<212> TYPE: DNA
<213> ORGANISM: Artificial sequence
<220> FEATURE:
<223> OTHER INFORMATION: Synthetic oligonucleotide

<400> SEQUENCE: 41
caggtgcagc tggtggagtc tgggggaggc ttggtcaagc ctggagggtc cctcagactc      60
tcctgcgtag cctctggatt caccttcagt gacttctaca tgagctggat ccgccaggct    120
ccagggaagg gccttgagtg cgtgtcctac atgagtgcaa ctggcggtaa tatatactat    180
gcagactcta tgaagggccg attaactatc tccagggaca acaccaagaa ctcattgttt    240
ctccaaatga acagcctgag agccgacgac acggccctgt attattgtgc gaggcggaag    300
tttggtgcag ggagtgcgat ctttgaccac tggagccagg gaaccctggt caccgtctcc    360
```

```
tcag                                                                  364

<210> SEQ ID NO 42
<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 42
tcctatgaac tgactcaacc accctcagtg tccgtgtccc caggacagac agccagcgtc     60
acctgctctg gagacaaatt gggtgaaaga tatgtgagtt ggtatcagca gaaggcaggc    120
cagtcccctg acttggtcat ctatcaaact aaccagcggc cctcagggat ccctgagcga    180
ttctctggct ccgactctgg gaacacagcc actctgacta tcagcgggac ccagggtctg    240
gatgaggcag actattactg tctgacgtgg gaccgcggca ctcctgtctt cggaactggg    300
accaaagtca ccgtcctag                                                 319

<210> SEQ ID NO 43
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 43
cagctgcagc tgcaggagtc gggcccaggc ctggtgaagc cttcggagac cctgtccctc     60
acctgcactg tgtctgatgc ctccatcgac actccgagtt acttctggag ctggatccgc    120
cagcccccag ggaaggggct ggagtggatt ggcagcatct attatactgg gaacaagtac    180
tccaatccgt ccctcaagag tcgagtcacc atgtccgtag acacgcccaa gaggcagttc    240
tccctgaggc tcagctctgt gaccgccgca gacacggctg tttattactg tgcgagatat    300
gttgattatg tttggttgag ggcttttgat atatggggcc aagggacaag ggtcaccgtc    360
tcctcag                                                              367

<210> SEQ ID NO 44
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 44
gaaattgtgt tgacacagtc tccagccacg ctgtctttgt ctccagggga aagggccacc     60
ctctcatgca gggccagtcc gagtgctggc cgcttcttag cttggtacca acagagacct    120
ggccaggctc ccaggctcct catctatgat gcatccaaga gggccactga caccccagcc    180
aggttcagtg gcagcgggtc tgggacagac ttcaatctta ccatcgccag cctagagcct    240
gaagattttg cagtttatta ctgtcaacac cgtagcaact ggccgctcac tttcggcgga    300
gggaccaagg tggagatcaa ac                                             322

<210> SEQ ID NO 45
<211> LENGTH: 367
<212> TYPE: DNA
<213> ORGANISM: Artificial sequence
<220> FEATURE:
<223> OTHER INFORMATION: Synthetic oligonucleotide
```

```
<400> SEQUENCE: 45
cagctgcagc tgcaggagtc gggcccagga ctggtgaagc cttcggagac cctgtcactc      60
acctgcagtg tctctgatga ctccatcagt actcctagtt acttctggac ctggatccgc     120
cagcccccag ggaaggggct ggagtggata gccagtatct attatactgg gaccacctac     180
tacaacccgt ccctcaagag tcgagtcacc ttatccgtcg acacgcccaa gaggcagttc     240
ttcctgaggc tgagctctgt gaccgccgca gacacggctg tttattactg tgcgagatat     300
cttgattacg tttggttgag ggcttttgat gtctggggcc aagggggcaat ggtcaccgtc     360 tcttcag                                                               367

<210> SEQ ID NO 46
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 46
gaaattgtgt tgacacagtc tccagccacc ctgtctttgt ctccagggga aagagccacc      60
ctctcctgca gggccagtcc gagtgttggc aggttcttag cctggtacca gcagaaacct     120
ggccaggctc ccaggctcct catctatgat gcatctcaga gggccactga catcccagcc     180
aggttcagtg ccagtgggtc tgggacagac ttcactctca ccatcgacag cctagagcct     240
gaagattttg caatatatta ctgtcagcac cgtagcaact ggccggtcac tttcggtgga     300
gggaccaggg tggagatcaa gc                                              322

<210> SEQ ID NO 47
<211> LENGTH: 369
<212> TYPE: DNA
<213> ORGANISM: Artificial sequence
<220> FEATURE:
<223> OTHER INFORMATION: Synthetic oligonucleotide

<400> SEQUENCE: 47
caggtgcagc tgcaggagtc gggcccagga ctggtgaagc cttcacagac cctgtccctc      60
acctgcactg tctctggtgg ctccatcagc agtggtggtt tcttctgggg ctggatccgc     120
cagcacccag ggagggacct ggagtggatt gggtacatct tttacactgg gagcaccaac     180
tacaacccgt ccctcaagaa tcgagttacc ctatcagtag acacgtctaa gaaccacttc     240
tccctgaact tgacctctgt gactgtcgcg gatacggccg tctattactg tgcgagacaa     300
gggggagtga gggggaacta ctacttcatg gacgtctggg gcaaagggac cacggtcacc     360
gtctcctca                                                             369

<210> SEQ ID NO 48
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 48
gacatccaga tgacccagtc tccatcctcc ctgtctgcgt ctgttggaga cagagtcacc      60
atcacttgcc gggcaagtca gagtattagc aactatttaa attggtatca acagaaacca     120
gggaaagccc ctaaactcct tatctatgct gcatccagat tgcagagtgg ggtcccatca     180
aggttcagtg gcagtggatc tgggacagag ctcaccctca ccatcagcag tctgcaacct     240
```

```
gaagattttg caacttattt ctgtcaacag agttacaata caccctactc ttttggccag      300
gggaccaagg tagagatcaa ag                                               322

<210> SEQ ID NO 49
<211> LENGTH: 375
<212> TYPE: DNA
<213> ORGANISM: Artificial sequence
<220> FEATURE:
<223> OTHER INFORMATION: Synthetic oligonucleotide

<400> SEQUENCE: 49
atggaattcc agctgcagga gtcgggccca ggactggtga agccttcgga gaccctgtcc       60
ctcaactgca gtgtctctgg tggctccatc agtaataatt attggaactg gatccggcag      120
cccccaggga agggactgga gtggattggg tatatctctt acagtgggag aacccattac      180
aacccgtccc tcaagagtcg ggtcagcata tcattgcaca cgtccaagaa ccatttctcc      240
ctgaagctga cctctgtggc cgctgcggac acggccatgt attactgtgc gagagagtcg      300
acatacagtt ataaactagg tgatgctttt gatatctggg gccaagggac aatggtcacc      360
gtctccgcaa gcttc                                                       375

<210> SEQ ID NO 50
<211> LENGTH: 345
<212> TYPE: DNA
<213> ORGANISM: Artificial sequence
<220> FEATURE:
<223> OTHER INFORMATION: Synthetic oligonucleotide

<400> SEQUENCE: 50
atggaattcc agtctgtgct gactcagccg ccctcaacgt ctgggacccc cgggcagagg       60
gtcaccatct cttgttctgg aagcagctcc aacatcggac gtaatacttt aaactggtac      120
cagcaggtcc caggaacggc ccccaaactc ctcatttata gtaatgatga gcggccctca      180
ggggtccctg accgattctc tggctccaag tctggcccct cagcctccct ggccatcagt      240
gggctccagt ctgaggatga ggctgattat tactgtgcag catgggatga caggctgaat      300
ggttgggtgt cggcggagg gaccaagctg accgtcctaa gcttg                       345

<210> SEQ ID NO 51
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 51
gaggtgcagc tggtgcagtc tggagcagag gtgaagaggg ccggggagtc tctgaagatc       60
tcctgtaagg gttctggata ccccttgcc acctactggg tcggctgggt gcgccagatg      120
cccggaaaag gcctggaatg gatgactatc atctatcctg aggactccga caccagatac      180
agcccgtcct tccaagacca tgtcaccatc tcagccgaca gtccctcag caccgcctac      240 ctgcagtgga gcagcctaaa ggcctcggac acagccatgt attactgtgc gagagtgtcc      300
cggtattatt atgatagtag aagttattac cctgatgctt tgacatctg gggccaaggg      360 acaatggtca ccgtctcctc ag                                               382

<210> SEQ ID NO 52
<211> LENGTH: 319
<212> TYPE: DNA
```

<213> ORGANISM: Artificial sequence
<220> FEATURE:
<223> OTHER INFORMATION: Synthetic oligonucleotide

<400> SEQUENCE: 52

```
tcctatgagc tgactcagcc accctcagtg tccgtgtccc caggacagac agccagcatc      60
acctgctctg agataaaatt gggggataaa tatgtttgct ggtatcaaca gaagccaggc     120
cggtcccctg tgttggtcgt ccatcaagat accaagcggc cctcaggat ccctgagcga      180 ttctctggct ccaattctgg ggacacagcc actctgacca tcagcgggac ccaggctatg     240
gatgaggctg actattactg tcaggcgtgg gacagtacca ttggggtctt cgggcctggg     300
accagggtca ccgtcctag                                                   319
```

<210> SEQ ID NO 53
<211> LENGTH: 117
<212> TYPE: PRT
<213> ORGANISM: Artificial sequence
<220> FEATURE:
<223> OTHER INFORMATION: Synthetic polypeptide

<400> SEQUENCE: 53

```
Glu Phe Gln Leu Val Gln Ser Gly Ser Glu Leu Arg Lys Pro Gly Ala
1               5                   10                  15

Ser Val Lys Val Ser Cys Lys Ala Ser Gly Tyr Thr Phe Thr Lys Tyr
            20                  25                  30

Gly Met Asn Trp Val Arg Gln Ala Pro Gly Gln Gly Leu Glu Trp Met
        35                  40                  45

Gly Trp Ile Asn Thr Asn Thr Ala Lys Pro Thr Tyr Ala Gln Asp Phe
    50                  55                  60

Thr Gly Arg Phe Val Phe Ser Leu Asp Thr Ser Val Asn Thr Ala Tyr
65                  70                  75                  80

Leu Glu Ile Ser Gly Leu Lys Ala Glu Asp Thr Ala Val Tyr Tyr Cys
                85                  90                  95

Ala Thr Asp Gly Ser Glu Gly Ser Trp Gly Gln Gly Thr Thr Val Thr
            100                 105                 110

Val Ser Ala Ser Phe
        115
```

<210> SEQ ID NO 54
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 54

```
Arg Ser Asp Ile Gln Met Thr Gln Ser Pro Ser Thr Leu Phe Ala Ser
1               5                   10                  15

Val Gly Asp Arg Val Thr Ile Thr Cys Arg Ala Ser Gln Ser Ile Gly
            20                  25                  30

Thr Trp Leu Ala Trp His Gln Gln Lys Pro Gly Thr Ala Pro Lys Val
        35                  40                  45

Leu Ile Tyr Lys Ala Ser Asn Leu Lys Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Asp Asp Val Ala Thr Tyr Tyr Cys Gln Gln Tyr Asn Thr Tyr
                85                  90                  95
```

```
Leu Gly Thr Phe Gly Gln Gly Thr Arg Val Glu Ile Lys Thr Ala Ala
            100                 105                 110
Ala

<210> SEQ ID NO 55
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 55

Glu Phe Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Ala Met Ser Trp Val Arg Gln Thr Pro Gly Glu Gly Leu Gln Trp Val
        35                  40                  45

Ser Ala Leu Thr Tyr Ser Gly Lys Thr Thr Tyr Tyr Ala Asp Ser Val
    50                  55                  60

Lys Gly Arg Phe Thr Ile Ser Arg Asp Asn Ser Lys Asn Leu Leu Phe
65                  70                  75                  80

Leu Gln Met Asn Ser Leu Arg Ala Gly Asp Thr Ala Ile Tyr Tyr Cys
                85                  90                  95

Ala Lys Glu Asp Tyr Asp Asp Arg Gly Phe Phe Asp Phe Trp Gly Gln
            100                 105                 110

Gly Thr Arg Val Thr Val Ser Ser Ala Ser Phe
            115                 120

<210> SEQ ID NO 56
<211> LENGTH: 113
<212> TYPE: PRT
<213> ORGANISM: Artificial sequence
<220> FEATURE:
<223> OTHER INFORMATION: Synthetic polypeptide

<400> SEQUENCE: 56

Arg Ser Asp Ile Gln Met Thr Gln Ser Pro Ser Ser Leu Ser Ala Ser
1               5                   10                  15

Val Gly Asp Arg Val Thr Ile Thr Cys Arg Ala Ser Gln Thr Ile Ser
            20                  25                  30

Thr Tyr Leu His Trp Tyr Gln Gln Lys Pro Gly Lys Ala Pro Asn Leu
        35                  40                  45

Leu Ile Tyr Ala Ala Ser Thr Leu Gln Ser Gly Val Pro Ser Arg Phe
    50                  55                  60

Ser Gly Ser Gly Ser Gly Thr Asp Phe Ser Leu Thr Ile Ser Ser Leu
65                  70                  75                  80

Arg Pro Glu Asp Phe Ala Ile Tyr Tyr Cys Gln Gln Gly Tyr Asn Asn
                85                  90                  95

Pro Tyr Thr Phe Gly Gln Gly Thr Lys Val Asp Ile Lys Thr Ala Ala
            100                 105                 110

Ala

<210> SEQ ID NO 57
<211> LENGTH: 126
<212> TYPE: PRT
<213> ORGANISM: Artificial sequence
<220> FEATURE:
```

<223> OTHER INFORMATION: Synthetic polypeptide

<400> SEQUENCE: 57

```
Glu Phe Gln Leu Val Glu Thr Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Gly Met His Trp Val Arg Gln Ala Pro Gly Lys Gly Leu Glu Trp Val
        35                  40                  45

Ala Val Ile Tyr Tyr Asp Glu Asn Asn Lys Tyr Tyr Ala Asp Ser Val
    50                  55                  60

Lys Gly Arg Phe Thr Ile Ser Arg Asp Asn Ser Lys Asn Thr Leu Ser
65                  70                  75                  80

Leu Gln Met Asn Ser Leu Arg Ala Asp Asp Thr Ala Val Tyr Tyr Cys
                85                  90                  95

Ala Arg Asp Val Val Val Ala Ala Phe Asp Phe Ser Tyr Gly Met Asp
            100                 105                 110

Val Trp Gly Gln Gly Thr Thr Val Thr Val Ser Ala Ser Phe
        115                 120                 125
```

<210> SEQ ID NO 58
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 58

```
Glu Phe Ser Tyr Asp Leu Thr Gln Pro Pro Ser Val Ser Val Ser Pro
1               5                   10                  15

Gly Gln Thr Ala Asn Ile Thr Cys Ser Gly Asn Lys Leu Glu Lys Phe
            20                  25                  30

Gly Cys Trp Tyr Gln Gln Lys Pro Gly Gln Ser Pro Leu Leu Val Ile
        35                  40                  45

Tyr Gln Asp Asn Lys Arg Pro Ser Gly Ile Pro Glu Arg Phe Ser Gly
    50                  55                  60

Ser Asn Ser Glu Asn Thr Ala Thr Leu Thr Ile Ser Gly Thr Gln Ala
65                  70                  75                  80

Leu Asp Glu Ala Asp Tyr Tyr Cys Gln Ala Trp Asp Gly Ser Phe Gly
                85                  90                  95

Gly Gly Thr Lys Leu Thr Val Leu Ser Leu Pro
            100                 105
```

<210> SEQ ID NO 59
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 59

```
Glu Phe Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Ser Thr Tyr Asp Ala Asp Ser Val
```

```
                        50                  55                  60
Lys Gly Arg Phe Thr Ile Ser Arg Asp Lys Phe Lys Ser Thr Val Tyr
 65                  70                  75                  80

Leu Gln Met Asn Ser Leu Arg Ala Glu Asp Thr Ala Val Tyr Tyr Cys
                 85                  90                  95

Ala Arg Asp Val Leu Tyr Ser Gly Ser Tyr Phe Asp Tyr Trp Ala Arg
                100                 105                 110

Asn Thr Met Val Thr Val Ser Ser Ala Ser Phe
            115                 120
```

<210> SEQ ID NO 60
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 60

```
Arg Ser Gln Met Thr Gln Ser Pro Ser Ser Leu Ser Ala Ser Ile Gly
 1               5                  10                  15

Asp Arg Val Thr Ile Thr Cys Arg Ala Ser Gln Gly Ile Arg Asn Asn
             20                  25                  30

Leu Gly Trp Tyr Gln Gln Thr Pro Gly Lys Ala Pro Arg Leu Leu Ile
         35                  40                  45

Tyr Ala Ala Ser Ser Leu Gln Ser Asp Val Pro Ser Arg Phe Ser Gly
 50                  55                  60

Ser Gly Ser Gly Thr Asp Phe Thr Leu Thr Ile Ser Ala Leu Gln Pro
 65                  70                  75                  80

Glu Asp Phe Ala Thr Tyr Tyr Cys Leu Gln Asp Tyr Asn Tyr Pro Arg
                 85                  90                  95

Thr Phe Gly Gln Gly Thr Lys Val Glu Ile Lys Thr Ala Ala Ala
                100                 105                 110
```

<210> SEQ ID NO 61
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 61

```
Glu Val Gln Leu Val Glu Ser Gly Gly Gly Leu Val Lys Pro Gly Gly
 1               5                  10                  15

Ser Leu Arg Leu Ser Cys Ala Ala Ser Gly Phe Pro Phe Ser Asp Tyr
             20                  25                  30

His Met Thr Trp Ile Arg Gln Ala Pro Gly Lys Gly Leu Glu Trp Ile
         35                  40                  45

Ser His Ile Ser Ser Ala Gly Asn Lys Ile His Tyr Ala Glu Ser Val
 50                  55                  60

Lys Gly Arg Phe Thr Ile Ser Arg Asp Asn Ala Lys Asn Ser Leu Phe
 65                  70                  75                  80

Leu His Met Asn Ser Leu Arg Ala Glu Asp Thr Ala Met Tyr Tyr Cys
                 85                  90                  95

Ala Arg
```

<210> SEQ ID NO 62
<211> LENGTH: 91
<212> TYPE: PRT

<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (64)..(64)
<223> OTHER INFORMATION: Xaa can be any naturally occurring amino acid

<400> SEQUENCE: 62

```
Gln Ser Val Leu Thr Gln Pro Pro Ser Val Ser Ala Ala Pro Gly Gln
1               5                   10                  15

Arg Val Thr Ile Ser Cys Ser Gly Gly Ser Ser Asn Ile Gly Tyr Asn
            20                  25                  30

Tyr Val Ala Trp Tyr Gln Gln Phe Pro Gly Thr Ala Pro Lys Leu Leu
        35                  40                  45

Leu Tyr Asp Asp Asp Glu Arg Pro Ser Xaa Leu His Lys Gln Val Xaa
    50                  55                  60

His His Arg Leu Glu Asp Ala Ser Ser His Pro Pro His Ser Gly His
65                  70                  75                  80

Arg Val Leu Gly Pro Val Cys Pro Asp Ser Thr
                85                  90
```

<210> SEQ ID NO 63
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 63

```
Glu Val Gln Leu Val Glu Ser Gly Gly Gly Leu Val Gln Pro Gly Gly
1               5                   10                  15

Ser Leu Lys Leu Ser Cys Ala Val Ser Gly Phe Ser Val Ser Asp Ser
            20                  25                  30

Ala Ile His Trp Val Arg Gln Ala Ser Gly Lys Gly Leu Glu Trp Val
        35                  40                  45

Gly His Met Arg Ser Gln Ala Asn Ser Tyr Ala Thr Ala Tyr Gly Ala
    50                  55                  60

Ser Val Arg Gly Arg Phe Asn Ile Ser Arg Asp Asp Ser Lys Asn Thr
65                  70                  75                  80

Ala Tyr Leu Gln Met Asn Ser Leu Asn Ile Asp Asp Thr Ala Val Tyr
                85                  90                  95

Tyr Cys Thr Arg Lys Val Asp Asn Arg His Gly Met Asp Val Trp Ala
            100                 105                 110

Lys Asp His Val
        115
```

<210> SEQ ID NO 64
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 64

```
Ser Tyr Val Leu Thr Gln Pro Pro Ser Val Ser Val Ala Pro Gly Gln
1               5                   10                  15
```

```
Thr Ala Arg Ile Pro Cys Gly Gly Asn Ser Ile Gly Ser Arg Ser Val
                20                  25                  30

His Trp Tyr Gln Gln Lys Pro Gly Arg Ala Pro Val Leu Val Ile Tyr
            35                  40                  45

Tyr Asp Arg Asp Arg Pro Ser Gly Ile Pro Glu Arg Phe Ser Gly Ser
 50                  55                  60

Asn Ser Gly Asn Thr Ala Thr Leu Thr Ile Asp Arg Val Glu Ala Gly
 65                  70                  75                  80

Asp Glu Ala Asp Tyr Tyr Cys Gln Val Trp Asp Gly Ser Ser Asp Gln
                85                  90                  95

Tyr Val Phe Gly Ile Gly Thr Lys Val Thr Val Leu
                100                 105

<210> SEQ ID NO 65
<211> LENGTH: 121
<212> TYPE: PRT
<213> ORGANISM: Artificial sequence
<220> FEATURE:
<223> OTHER INFORMATION: Synthetic polypeptide

<400> SEQUENCE: 65

Glu Phe Gln Leu Val Glu Ser Gly Gly Gly Leu Ile Gln Pro Gly Gly
 1               5                  10                  15

Ser Leu Arg Leu Ser Cys Ala Gly Ser Gly Phe Thr Val Thr Thr Asn
                20                  25                  30

Tyr Met Ala Trp Val Arg Gln Ala Pro Gly Lys Gly Leu Glu Trp Val
            35                  40                  45

Ser Thr Ile Tyr Ser Ala Gly Ser Thr Phe Tyr Ala Asp Ser Val Lys
 50                  55                  60

Gly Arg Phe Thr Ile Ser Gly Asp Asn Ser Lys Asn Thr Leu Tyr Leu
 65                  70                  75                  80

Gln Met Gly Ser Leu Arg Ala Glu Asp Thr Ala Val Tyr Tyr Cys Ala
                85                  90                  95

Arg Glu Asn Pro Ala Gln Asp Ala Phe Asp Ile Trp Ala Lys Asp Thr
                100                 105                 110

Met Val Thr Val Ser Ser Ala Ser Phe
            115                 120

<210> SEQ ID NO 66
<211> LENGTH: 214
<212> TYPE: PRT
<213> ORGANISM: Artificial sequence
<220> FEATURE:
<223> OTHER INFORMATION: Synthetic polypeptide

<400> SEQUENCE: 66

Glu Phe Ser Tyr Glu Leu Thr Gln Pro Leu Ser Val Ser Val Ala Leu
 1               5                  10                  15

Gly Gln Thr Ala Arg Ile Thr Cys Gly Gly Asn Asn Ile Gly Ser Lys
                20                  25                  30

Asn Val His Trp Tyr Gln Gln Lys Pro Gly Leu Ala Pro Val Leu Val
            35                  40                  45

Ile Tyr Arg Asp Ser Asn Arg Pro Ser Gly Ile Pro Ala Arg Phe Ser
 50                  55                  60

Gly Ser Ser Ser Gly Asn Thr Ala Thr Leu Thr Ile Ser Ser Ala Gln
 65                  70                  75                  80

Ala Gly Asp Glu Ala Asp Tyr Tyr Cys His Val Trp Asp Thr Ser Thr
                85                  90                  95
```

Val Val Phe Gly Gly Gly Thr Lys Leu Thr Val Leu Ser Leu Pro Lys
            100                 105                 110

Ala Ala Pro Ser Val Thr Leu Phe Pro Pro Ser Ser Glu Glu Leu Gln
            115                 120                 125

Ala Asn Lys Ala Thr Leu Val Cys Leu Ile Ser Asp Phe Tyr Pro Gly
            130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                    165                 170                 175

Ser Ser Tyr Leu Ser Leu Thr Pro Glu Gln Trp Lys Ser His Lys Ser
            180                 185                 190

Tyr Ser Cys Gln Val Thr His Glu Gly Ser Thr Val Glu Lys Thr Val
            195                 200                 205

Ala Pro Thr Glu Cys Ser
        210

<210> SEQ ID NO 67
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 67

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Asp
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Arg Thr Tyr Tyr Asn Pro Ser Phe Lys
    50                  55                  60

Ser Arg Val Ala Ile Ser Leu Asp Thr Ser Lys Ile Gln Phe Ser Leu
65                  70                  75                  80

Asn Leu Thr Ser Val Thr Ala Ala Asp Thr Ala Val Tyr Tyr Cys Ala
                85                  90                  95

Arg Glu Arg Leu Asp Ala Phe Asp Met Trp Gly Gln Gly Thr Val Val
            100                 105                 110

Phe Val Ser Ser
        115

<210> SEQ ID NO 68
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 68

Gln Ser Val Leu Thr Gln Pro Pro Ser Ala Ser Gly Thr Pro Gly Gln
1               5                   10                  15

Arg Val Thr Ile Ser Cys Ser Gly Gly Ser Ser Asn Ile Gly Ser Asn
            20                  25                  30

Tyr Val Tyr Trp Tyr Gln Arg Leu Pro Gly Thr Ala Pro Lys Leu Leu
        35                  40                  45

Ile Tyr Arg Asn Asn Gln Arg Pro Ser Gly Val Pro Asp Arg Phe Ser

```
                    50                  55                  60
Gly Ser Lys Ser Gly Thr Ser Ala Ser Pro Ala Ile Ser Gly Leu Arg
 65                  70                  75                  80

Ser Glu Asp Glu Ala Asp Tyr Phe Cys Ala Trp Asp Asp Arg Leu
                     85                  90                  95

Ser Ser Trp Val Phe Gly Glu Gly Thr Lys Leu Thr Val Leu
                100                 105                 110

<210> SEQ ID NO 69
<211> LENGTH: 130
<212> TYPE: PRT
<213> ORGANISM: Artificial sequence
<220> FEATURE:
<223> OTHER INFORMATION: Synthetic polypeptide

<400> SEQUENCE: 69

Val Leu Cys Gln Val Gln Leu Val Gln Ser Gly Gly Leu Val Gln
  1               5                  10                  15

Pro Gly Arg Ser Leu Arg Leu Ser Cys Ala Ala Ser Gly Phe Thr Phe
                 20                  25                  30

Asp Asp Tyr Ala Met His Trp Val Arg Gln Ala Pro Gly Lys Gly Leu
         35                  40                  45

Glu Trp Val Ser Gly Ile Ser Trp Asn Ser Asp Ser Ile Ala Tyr Ala
 50                  55                  60

Asp Ser Val Lys Gly Arg Phe Thr Ile Ser Arg Asp Asn Thr Lys Asn
 65                  70                  75                  80

Ser Leu Tyr Leu Glu Met Asn Ser Leu Arg Pro Glu Asp Thr Ala Leu
                 85                  90                  95

Tyr Tyr Cys Ala Lys Val Arg Leu Asp Phe Trp Thr Gly Pro Met Gly
                100                 105                 110

Tyr Phe Gln His Trp Gly Arg Gly Thr Leu Val Thr Val Ser Ser Ala
            115                 120                 125

Ser Phe
    130

<210> SEQ ID NO 70
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 70

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Thr Ile Thr Ser Asn
                 20                  25                  30

Tyr Leu Ala Trp Tyr Gln Gln Lys Pro Gly Gln Ala Pro Arg Leu Leu
         35                  40                  45

Ile Tyr Gly Ala Ser Thr Arg Ala Thr Gly Ile Pro Asp Arg Phe Ser
 50                  55                  60

Gly Ser Gly Ser Gly Thr Asp Phe Thr Leu Thr Ile Asn Arg Leu Glu
 65                  70                  75                  80

Pro Glu Asp Phe Ala Leu Tyr Tyr Cys Gln Gln Tyr Gly Ser Tyr Arg
                 85                  90                  95

Gly Val Phe Thr Phe Gly Pro Gly Thr Lys Val Asp Ile Lys Arg Thr
                100                 105                 110
```

Ala Ala Ala Pro Ser Val Phe Ile Phe Pro Pro
            115                 120

<210> SEQ ID NO 71
<211> LENGTH: 124
<212> TYPE: PRT
<213> ORGANISM: Artificial sequence
<220> FEATURE:
<223> OTHER INFORMATION: Synthetic polypeptide

<400> SEQUENCE: 71

Glu Phe Gln Leu Val Glu Ser Gly Gly Gly Phe Val Gln Pro Gly Gly
1               5                   10                  15

Ser Leu Arg Leu Ser Cys Ala Ala Ser Gly Phe Ser Val Ile Thr Asn
            20                  25                  30

Tyr Met Ser Trp Val Arg Gln Ala Pro Gly Lys Gly Leu Glu Trp Val
        35                  40                  45

Ser Leu Ile Tyr Ser Gly Gly Ser Thr Tyr Tyr Ala Asp Ser Val Lys
    50                  55                  60

Gly Arg Phe Thr Leu Ser Arg Asp Asn Ser Lys Asn Thr Leu Asn Leu
65                  70                  75                  80

Gln Met Asn Ser Leu Arg Ala Glu Asp Thr Ala Val Tyr Tyr Cys Ala
                85                  90                  95

Arg Val Asp Ile Thr Ala Thr Gly Thr Gly Gly Phe Asp Ile Trp Ala
            100                 105                 110

Lys Asp Thr Met Val Thr Val Ser Ser Ala Ser Phe
            115                 120

<210> SEQ ID NO 72
<211> LENGTH: 115
<212> TYPE: PRT
<213> ORGANISM: Artificial sequence
<220> FEATURE:
<223> OTHER INFORMATION: Synthetic polypeptide

<400> SEQUENCE: 72

Glu Phe Gln Ser Ala Leu Thr Gln Pro Ala Ser Val Ser Gly Ser Pro
1               5                   10                  15

Gly Gln Ser Ile Thr Leu Ser Cys Thr Gly Thr Ser Ser Asp Val Gly
            20                  25                  30

Ser Tyr Asn Leu Val Ser Trp Tyr Gln Gln His Pro Gly Lys Ala Pro
        35                  40                  45

Lys Leu Met Ile Tyr Glu Val Thr Lys Arg Pro Ser Gly Val Ser Asn
    50                  55                  60

Arg Phe Ser Gly Ser Lys Ser Gly Asn Thr Ala Ser Leu Thr Ile Ser
65                  70                  75                  80

Gly Leu Gln Ala Glu Asp Glu Ala Asp Tyr Tyr Cys Cys Ser Tyr Ala
                85                  90                  95

Gly Ser Ser Ile Ser Phe Val Phe Gly Thr Gly Thr Lys Val Thr Val
            100                 105                 110

Leu Ser Leu
        115

<210> SEQ ID NO 73
<211> LENGTH: 129
<212> TYPE: PRT
<213> ORGANISM: Artificial sequence
<220> FEATURE:
<223> OTHER INFORMATION: Synthetic polypeptide

<400> SEQUENCE: 73

Glu Phe Gln Leu Val Glu Ser Gly Gly Gly Val Val Gln Pro Gly Ser
1               5                   10                  15

Ser Leu Arg Leu Ser Cys Ala Val Ser Gly Phe Thr Val Arg Ser Tyr
            20                  25                  30

Gly Met His Trp Val Arg Gln Ala Pro Gly Lys Gly Leu Glu Trp Val
        35                  40                  45

Ala Leu Ile Leu Phe Asp Gly Thr Thr Lys His Tyr Ala Asp Ser Val
    50                  55                  60

Lys Gly Arg Phe Thr Ile Ser Arg Asp Asn Ser Lys Asp Thr Leu Tyr
65                  70                  75                  80

Leu Gln Met Thr Ser Leu Gly Ala Glu Asp Thr Ala Met Tyr Tyr Cys
                85                  90                  95

Val Arg Asp Phe Asn Gln Phe Val Lys Arg Phe Val Asp Gly Pro Ala
            100                 105                 110

Phe Asp Leu Trp Gly Gln Gly Thr Arg Val Thr Val Ser Ser Ala Ser
            115                 120                 125

Phe

<210> SEQ ID NO 74

<400> SEQUENCE: 74

000

<210> SEQ ID NO 75
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 75

Glu Val Gln Leu Val Glu Ser Gly Gly Gly Val Val Gln Pro Gly Arg
1               5                   10                  15

Ser Leu Arg Leu Ser Cys Ala Gly Ser Gly Phe Thr Phe Ser Thr Tyr
            20                  25                  30

Val Met His Trp Val Arg Gln Ala Pro Gly Lys Gly Leu Glu Trp Val
        35                  40                  45

Ala Val Ile Ser Tyr Asp Gly Thr Asn Lys Tyr Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Leu Asn Arg Leu Arg Ala Glu Asp Thr Ala Val Tyr Tyr Cys
                85                  90                  95

Ala Lys Thr Met Asp Asp Ser Ser Gly Tyr Tyr Cys Pro Asp Tyr Trp
            100                 105                 110

<210> SEQ ID NO 76
<211> LENGTH: 101
<212> TYPE: PRT
<213> ORGANISM: Artificial sequence
<220> FEATURE:
<223> OTHER INFORMATION: Synthetic polypeptide

<400> SEQUENCE: 76

Ser Ser Glu Leu Thr Gln Asp Pro Ala Val Ser Val Ala Leu Gly Gln
1               5                   10                  15

```
Thr Val Lys Ile Thr Cys Gln Gly Asp Ser Leu Arg Asn Tyr Phe Ala
            20                  25                  30

Asn Trp Tyr Gln Gln Lys Pro Gly Gln Ala Pro Val Leu Val Ile Tyr
            35                  40                  45

Gly Gln Asn Asn Arg Pro Ser Gly Ile Pro Asp Arg Phe Ser Gly Ser
        50                  55                  60

Thr Ser Gly Asn Thr Gly Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

Leu Tyr Val Phe Gly
            100

<210> SEQ ID NO 77
<211> LENGTH: 120
<212> TYPE: PRT
<213> ORGANISM: Artificial sequence
<220> FEATURE:
<223> OTHER INFORMATION: Synthetic polypeptide

<400> SEQUENCE: 77

Gln Val Gln Leu Val Glu Ser Gly Gly Asp Leu Val Thr Pro Gly Gly
1               5                   10                  15

Ser Leu Arg Leu Ser Cys Ala Ala Ser Gly Phe Ala Phe Ser Gly Tyr
            20                  25                  30

Tyr Met Ser Trp Ile Arg Gln Ala Pro Gly Lys Gly Leu Glu Trp Ile
        35                  40                  45

Ser Tyr Ile Asn Ser Asn Gly Leu Thr Ile Ser Tyr Ala Asp Ser Val
    50                  55                  60

Lys Gly Arg Phe Thr Val Ser Arg Asp Asn Ala Lys Asn Ser Leu Phe
65                  70                  75                  80

Leu Gln Met Ser Ser Leu Arg Ala Glu Asp Thr Ala Ile Tyr Tyr Cys
                85                  90                  95

Ala Arg Asp Trp Gly Thr Thr Leu Val Thr Phe Asp Leu Trp Gly Gln
            100                 105                 110

Gly Thr Leu Val Thr Val Ser Ser
        115                 120

<210> SEQ ID NO 78
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 78

Gln Pro Val Leu Thr Gln Ser Ser Ser Ala Ser Ala Ser Met Gly Ser
1               5                   10                  15

Ser Ala Lys Leu Thr Cys Thr Leu Ser Ser Gly His Arg Gly Tyr Asn
            20                  25                  30

Ile Ala Trp Leu Gln Gln His Pro Gly Lys Ala Pro Leu Tyr Leu Thr
        35                  40                  45

Asn Leu Glu Gly Ser Asp Ser Tyr Lys Asn Asp Arg Leu Thr Val Ser
    50                  55                  60

Ser Ser Gly Ala Asp Arg Tyr Leu Thr Ile Ser Asn Leu Gln Pro Glu
65                  70                  75                  80

Asp Glu Ala Thr Tyr Tyr Cys Phe Thr Trp Asp Ser Asp Ser Arg Val
                85                  90                  95
```

```
Phe Gly Gly Gly Thr His Leu Thr Val Leu
            100                 105
```

<210> SEQ ID NO 79
<211> LENGTH: 116
<212> TYPE: PRT
<213> ORGANISM: Artificial sequence
<220> FEATURE:
<223> OTHER INFORMATION: Synthetic polypeptide

<400> SEQUENCE: 79

```
Gln Val His Leu Val Gln Ser Gly Val Asp Val Lys Lys Pro Gly Ala
1               5                   10                  15

Ser Val Lys Leu Ser Cys Lys Thr Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Thr Tyr Asp Gly Ala Thr Asn Tyr Ser Gln Asn Leu
    50                  55                  60

Gln Gly Arg Ile Ile Met Thr Thr Asp Thr Ser Lys Arg Thr Ala Tyr
65                  70                  75                  80

Leu Gln Met Arg Ser Leu Arg Ser Asp Thr Ala Val Tyr Tyr Cys
                85                  90                  95

Ala Arg Gly Arg Asp Ser Pro Asp His Trp Gly Gln Gly Thr Leu Val
            100                 105                 110

Thr Val Ser Ser
        115
```

<210> SEQ ID NO 80
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 80

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Asn Arg Trp
            20                  25                  30

Leu Ala Trp Tyr Gln Gln Lys Pro Gly Thr Ala Pro Lys Leu Leu Ile
        35                  40                  45

Phe Lys Ala Ser Thr Leu Asp Ser Gly Val Pro Ala Arg Phe Ser Gly
    50                  55                  60

Thr Gly Ser Glu Thr Glu Phe Ser Leu Thr Ile Asn Ser Leu Gln Pro
65                  70                  75                  80

Asp Asp Phe Ala Thr Tyr Tyr Cys Gln Gln Tyr Asp His Phe Pro His
                85                  90                  95

Thr Phe Gly Pro Gly Thr Lys Leu Asp Ile Lys
            100                 105
```

<210> SEQ ID NO 81
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 81

```
Gln Val Gln Leu Val Gln Ser Gly Thr Glu Val Lys Lys Pro Gly Ala
1               5                   10                  15

Ser Val Lys Val Ser Cys Lys Thr Ser Gly Tyr Thr Phe Ile Ser Tyr
            20                  25                  30

Gly Val Thr Trp Val Arg Gln Ala Pro Gly Gln Gly Leu Glu Trp Met
        35                  40                  45

Gly Trp Ile Ser Gly Tyr Asn Gly Asn Pro Lys Tyr Ala Glu Lys Phe
    50                  55                  60

His Asp Arg Ile Thr Met Thr Thr Asp Arg Ser Thr Asn Thr Val Tyr
65                  70                  75                  80

Leu Glu Leu Arg Ser Leu Arg Ser Asp Asp Thr Ala Val Tyr Tyr Cys
                85                  90                  95

Ala Arg Trp Met Val Gly Asn Ile Asn Pro Phe Asp His Trp Ala
            100                 105                 110
```

```
<210> SEQ ID NO 82
<211> LENGTH: 82
<212> TYPE: PRT
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (13)..(14)
<223> OTHER INFORMATION: Xaa can be any naturally occurring amino acid
<220> FEATURE:
<221> NAME/KEY: misc_feature
<222> LOCATION: (19)..(20)
<223> OTHER INFORMATION: Xaa can be any naturally occurring amino acid
<220> FEATURE:
<221> NAME/KEY: misc_feature
<222> LOCATION: (25)..(25)
<223> OTHER INFORMATION: Xaa can be any naturally occurring amino acid
<220> FEATURE:
<221> NAME/KEY: misc_feature
<222> LOCATION: (28)..(28)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid

<400> SEQUENCE: 82

Arg Asn Ser Phe Gly Xaa Trp Tyr Lys Gln Thr Pro Xaa Xaa Val Pro
1               5                   10                  15

Val Leu Xaa Xaa Tyr Gly Gln Asn Xaa Arg Pro Xaa Val Ile Pro Asp
            20                  25                  30

Arg Phe Ser Gly Ser Thr Ser Gly Asn Thr Gly Ser Leu Thr Ile Thr
        35                  40                  45

Gly Xaa Gln Ala Glu Asp Glu Asp Asp Tyr Tyr Cys Asn Ser Arg Asp
    50                  55                  60

Ser Ser Gly Asn His Phe Tyr Val Phe Gly Thr Gly Thr Lys Val Thr
65                  70                  75                  80

Val Leu
```

```
<210> SEQ ID NO 83
<211> LENGTH: 115
<212> TYPE: PRT
<213> ORGANISM: Artificial sequence
<220> FEATURE:
<223> OTHER INFORMATION: Synthetic polypeptide
```

<400> SEQUENCE: 83

Glu Val Gln Val Gly Gln Ser Gly Pro Val Leu Lys Lys Pro Gly Glu
1               5                   10                  15

Ser Met Lys Ile Ser Gly Arg Gly Ser Gly Tyr Arg Phe Asn Thr Tyr
            20                  25                  30

Trp Val Ala Trp Val Arg Gln Met Pro Gly Lys Gly Leu Glu Trp Met
        35                  40                  45

Gly Met Ile Tyr Gly Asp Leu Asp Thr Lys Tyr Ser Pro Ser Phe Gln
    50                  55                  60

Gly Gln Val Thr Ile Ser Ala Asp Lys Ser Ser Asn Thr Ala Tyr Leu
65                  70                  75                  80

Gln Trp Ser Ser Leu Lys Ala Ser Asp Thr Ala Met Tyr Tyr Cys Ala
                85                  90                  95

Arg Glu Val Tyr Val Ala Ser Thr Asp Ser Asp Tyr Tyr Gly Met Asp
            100                 105                 110

Val Trp Ala
        115

<210> SEQ ID NO 84
<211> LENGTH: 109
<212> TYPE: PRT
<213> ORGANISM: Artificial sequence
<220> FEATURE:
<223> OTHER INFORMATION: Synthetic polypeptide

<400> SEQUENCE: 84

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Asn Asp Val Gly Arg Ser
            20                  25                  30

Asp Leu Val Ala Trp Tyr Gln Gln His Pro Asp Lys Ala Pro Arg Leu
        35                  40                  45

Ile Ile Tyr Glu Ser Ser Lys Arg Pro Gly Val Ser Ala Arg Phe Ser
    50                  55                  60

Gly Ser Arg Ser Gly Ile Thr Ala Ser Leu Thr Ile Ser Asp Leu Gln
65                  70                  75                  80

Ala Glu Asp Glu Ala Asp Tyr Tyr Cys Cys Ser Tyr Ala Gly Gly Asn
                85                  90                  95

Thr Tyr Val Phe Gly Thr Ala Thr Gly Val Thr Val Leu
            100                 105

<210> SEQ ID NO 85
<211> LENGTH: 111
<212> TYPE: PRT
<213> ORGANISM: Artificial sequence
<220> FEATURE:
<223> OTHER INFORMATION: Synthetic polypeptide

<400> SEQUENCE: 85

Glu Val Gln Leu Val Glu Thr Gly Gly Gly Leu Ile Gln Pro Gly Gly
1               5                   10                  15

Ser Leu Arg Leu Ser Cys Ala Ala Ser Gly Phe Ser Val Ser Thr Arg
            20                  25                  30

Phe Met Ser Trp Val Arg Gln Ala Pro Gly Gln Gly Leu Glu Trp Val
        35                  40                  45

Ser Val Val Tyr Lys Asp Gly Asp Thr Phe Asn Ser Asp Ser Val Lys
    50                  55                  60

Gly Arg Phe Ser Ile Ser Arg Asp Asn Ser Lys Asn Thr Val Phe Leu
65                  70                  75                  80

Gln Met Asn Arg Leu Arg Val Glu Asp Thr Ala Val Tyr Phe Cys Val
                85                  90                  95

Arg His Gly Asp Gly Trp Asn Tyr Val Asp Ser Trp Gly Leu Glu
            100                 105                 110

<210> SEQ ID NO 86
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 86

Glu Ile Val Met Thr Gln Ser Pro Ala Thr Leu Ser Val Ser Pro Gly
1               5                   10                  15

Glu Gly Ala Thr Leu Ser Cys Arg Ala Ser His Ser Leu Ser Ser His
                20                  25                  30

Leu Ala Trp Tyr Gln Gln Lys Pro Gly Gln Ala Pro Arg Leu Leu Ile
            35                  40                  45

Tyr Asp Ala Ser Val Arg Ala Thr Asp Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Leu
                85                  90                  95

Thr Phe Gly Gly Gly Thr Lys Leu Glu Ile Lys
            100                 105

<210> SEQ ID NO 87
<211> LENGTH: 119
<212> TYPE: PRT
<213> ORGANISM: Artificial sequence
<220> FEATURE:
<223> OTHER INFORMATION: Synthetic polypeptide

<400> SEQUENCE: 87

Glu Val Gln Leu Val Glu Ser Gly Gly Asp Leu Val Lys Pro Gly Gly
1               5                   10                  15

Ser Leu Arg Ile Ser Cys Ala Ala Ser Gly Phe Ser Phe Ser Asp Tyr
                20                  25                  30

Tyr Met Ser Trp Ile Arg Gln Ala Pro Gly Lys Gly Leu Glu Trp Val
            35                  40                  45

Ala Tyr Ile Ser Gly Ser Ser Ala Tyr Thr Ser Tyr Ala Asp Ser Val
    50                  55                  60

Lys Gly Arg Phe Ser Ile Ser Arg Asp Asn Ala Asn Asn Ser Leu Phe
65                  70                  75                  80

Leu Gln Met Asn Ser Leu Arg Ala Glu Asp Thr Ala Thr Tyr Phe Cys
                85                  90                  95

Ala Lys Asp Tyr Cys Gly Ser Gly Ala Cys Tyr Thr Ala Asp Pro Gly
            100                 105                 110

Phe Phe His Gln Trp Ala Arg
            115

<210> SEQ ID NO 88
<211> LENGTH: 110
<212> TYPE: PRT

```
<213> ORGANISM: Artificial sequence
<220> FEATURE:
<223> OTHER INFORMATION: Synthetic polypeptide
<220> FEATURE:
<221> NAME/KEY: misc_feature
<222> LOCATION: (109)..(109)
<223> OTHER INFORMATION: Xaa can be any naturally occurring amino acid

<400> SEQUENCE: 88

Ser Tyr Val Leu Thr Gln Pro Pro Ser Val Ser Val Ala Pro Gly Lys
1               5                   10                  15

Thr Ala Thr Ile Ser Cys Gly Gly Asn Asn Ile Gly Ser Lys Ser Val
            20                  25                  30

His Trp Tyr Gln Gln Lys Pro Gly Gln Ala Pro Ile Val Val Ile Tyr
        35                  40                  45

Tyr Asp Ser Asp Arg Pro Ser Gly Ile Pro Glu Arg Phe Ser Gly Ile
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Thr Asn Asp His
                85                  90                  95

Pro Ser Tyr Val Phe Gly Ala Gly Thr Lys Val Thr Xaa Leu
            100                 105                 110

<210> SEQ ID NO 89
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Gly Leu Glu Trp Val
        35                  40                  45

Ser Thr Ile Ser Gly Ser Gly Ser Ser Thr Tyr Asp Ala Asp Ser Val
    50                  55                  60

Lys Gly Arg Phe Thr Ile Ser Arg Asp Lys Phe Lys Ser Thr Val Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 90
<211> LENGTH: 108
<212> TYPE: PRT
<213> ORGANISM: Artificial sequence
<220> FEATURE:
<223> OTHER INFORMATION: Synthetic polypeptide

<400> SEQUENCE: 90

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Val Gly Lys Tyr
            20                  25                  30

Leu Asn Trp Tyr Gln Gln Lys Pro Gly Glu Ala Pro Lys Leu Leu Ile
        35                  40                  45
```

```
Tyr Ala Ala Ser Arg Leu Asp Arg Gly Val Ser Ser Arg Phe Ser Gly
            50                  55                  60

Ser Gly Ile Gly Ala Asp Phe Thr Leu Thr Ile Ser Gly Leu Gln Pro
65                  70                  75                  80

Glu Asp Phe Ala Thr Tyr Tyr Cys Gln Gln Ser Ser Ser Thr Ala Ala
                85                  90                  95

Trp Thr Phe Gly Gln Gly Thr Lys Val Glu Ile Lys
                100                 105

<210> SEQ ID NO 91
<211> LENGTH: 114
<212> TYPE: PRT
<213> ORGANISM: Artificial sequence
<220> FEATURE:
<223> OTHER INFORMATION: Synthetic polypeptide

<400> SEQUENCE: 91

Gln Leu Gln Lys Gln Gln Trp Ala Ala Gly Leu Lys His Pro Ser Ala
1               5                   10                  15

Thr Leu Ser Phe Ile Cys Gly Ile Asn Gly Ser Phe Ser Gly Phe
            20                  25                  30

Leu Arg Thr Trp Ile Arg Gln Ser Pro Gly Lys Gly Val Glu Leu Ile
            35                  40                  45

Gly Glu Ile Asn Asn Ser Gly Thr Thr Lys Tyr Asn Ser Ser Leu Lys
50                  55                  60

Ser Arg Leu Thr Ile Ser Ile Asp Thr Ser Lys Asp Gln Val Ser Leu
65                  70                  75                  80

Gln Leu Arg Ser Val Thr Ala Ala Asp Thr Ala Thr Tyr Phe Cys Ala
                85                  90                  95

Arg Thr Pro Val Leu Arg Tyr Leu Thr Val Gly Pro Trp Gly Gln Gly
                100                 105                 110

Thr Leu

<210> SEQ ID NO 92
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 92

Ser Tyr Glu Leu Thr Gln Pro Pro Ser Val Ser Leu Ser Pro Gly Gln
1               5                   10                  15

Thr Ala Thr Ile Thr Cys Ser Gly Asp Lys Leu Gly Asp Lys Ser Val
            20                  25                  30

Ser Trp Tyr Gln Gln Met Pro Gly Gln Ser Pro Ile Leu Val Ile Tyr
            35                  40                  45

Gln Asp Tyr Lys Arg Pro Ser Gly Ile Ser Glu Arg Phe Ser Gly Ser
50                  55                  60

Asn Ser Gly Asn Thr Ala Thr Leu Thr Ile Ser Glu Thr Gln Ala Met
65                  70                  75                  80

Asp Glu Ala Asp Tyr Tyr Cys Gln Ala Trp Asp Arg Lys Ile Gly Gln
                85                  90                  95

Phe Gly Gly Gly Thr Lys Met Thr Val Ile
                100                 105

<210> SEQ ID NO 93
```

<211> LENGTH: 97
<212> TYPE: PRT
<213> ORGANISM: Artificial sequence
<220> FEATURE:
<223> OTHER INFORMATION: Synthetic polypeptide

<400> SEQUENCE: 93

Gln Val Gln Leu Val Glu Ser Gly Gly Gly Leu Val Lys Pro Gly Gly
1               5                   10                  15

Ser Leu Arg Leu Ser Cys Val Ala Ser Gly Phe Thr Phe Ser Asp Phe
            20                  25                  30

Tyr Met Ser Trp Ile Arg Gln Ala Pro Gly Lys Gly Leu Glu Cys Val
        35                  40                  45

Ser Tyr Met Ser Ala Thr Gly Gly Asn Ile Tyr Tyr Ala Asp Ser Met
    50                  55                  60

Lys Gly Arg Leu Thr Ile Ser Arg Asp Asn Thr Lys Asn Ser Leu Phe
65                  70                  75                  80

Leu Gln Met Asn Ser Leu Arg Ala Asp Asp Thr Ala Leu Tyr Tyr Cys
                85                  90                  95

Ala

<210> SEQ ID NO 94
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 94

Ser Tyr Glu Leu Thr Gln Pro Pro Ser Val Ser Val Ser Pro Gly Gln
1               5                   10                  15

Thr Ala Ser Val Thr Cys Ser Gly Asp Lys Leu Gly Glu Arg Tyr Val
            20                  25                  30

Ser Trp Tyr Gln Gln Lys Ala Gly Gln Ser Pro Asp Leu Val Ile Tyr
        35                  40                  45

Gln Thr Asn Gln Arg Pro Ser Gly Ile Pro Glu Arg Phe Ser Gly Ser
    50                  55                  60

Asp Ser Gly Asn Thr Ala Thr Leu Thr Ile Ser Gly Thr Gln Gly Leu
65                  70                  75                  80

Asp Glu Ala Asp Tyr Tyr Cys Leu Thr Trp Asp Arg Gly Thr Pro Val
                85                  90                  95

Phe Gly Thr Gly Thr Lys Val Thr Val Leu
            100                 105

<210> SEQ ID NO 95
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 95

Gln Leu Gln Leu Gln Glu Ser Gly Pro Gly Leu Val Lys Pro Ser Glu
1               5                   10                  15

Thr Leu Ser Leu Thr Cys Thr Val Ser Asp Ala Ser Ile Asp Thr Pro
            20                  25                  30

Ser Tyr Phe Trp Ser Trp Ile Arg Gln Pro Pro Gly Lys Gly Leu Glu
        35                  40                  45

Trp Ile Gly Ser Ile Tyr Tyr Thr Gly Asn Lys Tyr Ser Asn Pro Ser

```
                        50                  55                  60

Leu Lys Ser Arg Val Thr Met Ser Val Asp Thr Pro Lys Arg Gln Phe
 65                  70                  75                  80

Ser Leu Arg Leu Ser Ser Val Thr Ala Ala Asp Thr Ala Val Tyr Tyr
                 85                  90                  95

Cys Ala Arg Tyr Val Asp Tyr Val Trp Leu Arg Ala Phe Asp Ile Trp
                100                 105                 110

Gly Gln Gly Thr Arg Val Thr Val Ser Ser
            115                 120

<210> SEQ ID NO 96
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 96

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Pro Ser Ala Gly Arg Phe
                20                  25                  30

Leu Ala Trp Tyr Gln Gln Arg Pro Gly Gln Ala Pro Arg Leu Leu Ile
             35                  40                  45

Tyr Asp Ala Ser Lys Arg Ala Thr Asp Thr Pro Ala Arg Phe Ser Gly
 50                  55                  60

Ser Gly Ser Gly Thr Asp Phe Asn Leu Thr Ile Ala Ser Leu Glu Pro
 65                  70                  75                  80

Glu Asp Phe Ala Val Tyr Tyr Cys Gln His Arg Ser Asn Trp Pro Leu
                 85                  90                  95

Thr Phe Gly Gly Gly Thr Lys Val Glu Ile Lys
                100                 105

<210> SEQ ID NO 97
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 97

Gln Leu Gln Leu Gln Glu Ser Gly Pro Gly Leu Val Lys Pro Ser Glu
 1               5                  10                  15

Thr Leu Ser Leu Thr Cys Ser Val Ser Asp Asp Ser Ile Ser Thr Pro
                20                  25                  30

Ser Tyr Phe Trp Thr Trp Ile Arg Gln Pro Pro Gly Lys Gly Leu Glu
             35                  40                  45

Trp Ile Ala Ser Ile Tyr Tyr Thr Gly Thr Thr Tyr Tyr Asn Pro Ser
 50                  55                  60

Leu Lys Ser Arg Val Thr Leu Ser Val Asp Thr Pro Lys Arg Gln Phe
 65                  70                  75                  80

Phe Leu Arg Leu Ser Ser Val Thr Ala Ala Asp Thr Ala Val Tyr Tyr
                 85                  90                  95

Cys Ala Arg Tyr Leu Asp Tyr Val Trp Leu Arg Ala Phe Asp Val Trp
                100                 105                 110

Gly Gln Gly Ala Met Val Thr Val Ser Ser
            115                 120
```

```
<210> SEQ ID NO 98
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 98

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Pro Ser Val Gly Arg Phe
            20                  25                  30

Leu Ala Trp Tyr Gln Gln Lys Pro Gly Gln Ala Pro Arg Leu Leu Ile
        35                  40                  45

Tyr Asp Ala Ser Gln Arg Ala Thr Asp Ile Pro Ala Arg Phe Ser Ala
50                  55                  60

Ser Gly Ser Gly Thr Asp Phe Thr Leu Thr Ile Asp Ser Leu Glu Pro
65                  70                  75                  80

Glu Asp Phe Ala Ile Tyr Tyr Cys Gln His Arg Ser Asn Trp Pro Val
                85                  90                  95

Thr Phe Gly Gly Gly Thr Arg Val Glu Ile Lys
            100                 105

<210> SEQ ID NO 99
<211> LENGTH: 123
<212> TYPE: PRT
<213> ORGANISM: Artificial sequence
<220> FEATURE:
<223> OTHER INFORMATION: Synthetic polypeptide

<400> SEQUENCE: 99

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Phe Phe Trp Gly Trp Ile Arg Gln His Pro Gly Arg Asp Leu Glu
        35                  40                  45

Trp Ile Gly Tyr Ile Phe Tyr Thr Gly Ser Thr Asn Tyr Asn Pro Ser
50                  55                  60

Leu Lys Asn Arg Val Thr Leu Ser Val Asp Thr Ser Lys Asn His Phe
65                  70                  75                  80

Ser Leu Asn Leu Thr Ser Val Thr Val Ala Asp Thr Ala Val Tyr Tyr
                85                  90                  95

Cys Ala Arg Gln Gly Gly Val Arg Gly Asn Tyr Tyr Phe Met Asp Val
            100                 105                 110

Trp Gly Lys Gly Thr Thr Val Thr Val Ser Ser
        115                 120

<210> SEQ ID NO 100
<211> LENGTH: 107
<212> TYPE: PRT
<213> ORGANISM: Artificial sequence
<220> FEATURE:
<223> OTHER INFORMATION: Synthetic polypeptide

<400> SEQUENCE: 100

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Asn Tyr
```

```
                    20                  25                  30

Leu Asn Trp Tyr Gln Gln Lys Pro Gly Lys Ala Pro Lys Leu Leu Ile
            35                  40                  45

Tyr Ala Ala Ser Arg Leu Gln Ser Gly Val Pro Ser Arg Phe Ser Gly
        50                  55                  60

Ser Gly Ser Gly Thr Glu Leu Thr Leu Thr Ile Ser Ser Leu Gln Pro
65                  70                  75                  80

Glu Asp Phe Ala Thr Tyr Phe Cys Gln Gln Ser Tyr Asn Thr Pro Tyr
                85                  90                  95

Ser Phe Gly Gln Gly Thr Lys Val Glu Ile Lys
            100                 105

<210> SEQ ID NO 101
<211> LENGTH: 122
<212> TYPE: PRT
<213> ORGANISM: Artificial sequence
<220> FEATURE:
<223> OTHER INFORMATION: Synthetic polypeptide

<400> SEQUENCE: 101

Glu Phe Gln Leu Gln Glu Ser Gly Pro Gly Leu Val Lys Pro Ser Glu
1               5                   10                  15

Thr Leu Ser Leu Asn Cys Ser Val Ser Gly Gly Ser Ile Ser Asn Asn
            20                  25                  30

Tyr Trp Asn Trp Ile Arg Gln Pro Pro Gly Lys Gly Leu Glu Trp Ile
        35                  40                  45

Gly Tyr Ile Ser Tyr Ser Gly Arg Thr His Tyr Asn Pro Ser Leu Lys
    50                  55                  60

Ser Arg Val Ser Ile Ser Leu His Thr Ser Lys Asn His Phe Ser Leu
65                  70                  75                  80

Lys Leu Thr Ser Val Ala Ala Ala Asp Thr Ala Met Tyr Tyr Cys Ala
                85                  90                  95

Arg Glu Ser Thr Tyr Ser Tyr Lys Leu Gly Asp Ala Phe Asp Ile Trp
            100                 105                 110

Gly Gln Gly Thr Met Val Thr Val Ser Ala
        115                 120

<210> SEQ ID NO 102
<211> LENGTH: 110
<212> TYPE: PRT
<213> ORGANISM: Artificial sequence
<220> FEATURE:
<223> OTHER INFORMATION: Synthetic polypeptide

<400> SEQUENCE: 102

Gln Ser Val Leu Thr Gln Pro Pro Ser Thr Ser Gly Thr Pro Gly Gln
1               5                   10                  15

Arg Val Thr Ile Ser Cys Ser Gly Ser Ser Asn Ile Gly Arg Asn
            20                  25                  30

Thr Leu Asn Trp Tyr Gln Gln Val Pro Gly Thr Ala Pro Lys Leu Leu
        35                  40                  45

Ile Tyr Ser Asn Asp Glu Arg Pro Ser Gly Val Pro Asp Arg Phe Ser
    50                  55                  60

Gly Ser Lys Ser Gly Pro Ser Ala Ser Leu Ala Ile Ser Gly Leu Gln
65                  70                  75                  80

Ser Glu Asp Glu Ala Asp Tyr Tyr Cys Ala Ala Trp Asp Asp Arg Leu
                85                  90                  95
```

Asn Gly Trp Val Phe Gly Gly Gly Thr Lys Leu Thr Val Leu
            100                 105                 110

<210> SEQ ID NO 103
<211> LENGTH: 127
<212> TYPE: PRT
<213> ORGANISM: Artificial sequence
<220> FEATURE:
<223> OTHER INFORMATION: Synthetic polypeptide

<400> SEQUENCE: 103

Glu Val Gln Leu Val Gln Ser Gly Ala Glu Val Lys Arg Ala Gly Glu
1               5                   10                  15

Ser Leu Lys Ile Ser Cys Lys Gly Ser Gly Tyr Pro Phe Ala Thr Tyr
            20                  25                  30

Trp Val Gly Trp Val Arg Gln Met Pro Gly Lys Gly Leu Glu Trp Met
        35                  40                  45

Thr Ile Ile Tyr Pro Glu Asp Ser Asp Thr Arg Tyr Ser Pro Ser Phe
    50                  55                  60

Gln Asp His Val Thr Ile Ser Ala Asp Lys Ser Leu Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Tyr Tyr Tyr Asp Ser Arg Ser Tyr Tyr Pro Asp
            100                 105                 110

Ala Phe Asp Ile Trp Gly Gln Gly Thr Met Val Thr Val Ser Ser
        115                 120                 125

<210> SEQ ID NO 104
<211> LENGTH: 106
<212> TYPE: PRT
<213> ORGANISM: Artificial sequence
<220> FEATURE:
<223> OTHER INFORMATION: Synthetic polypeptide

<400> SEQUENCE: 104

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
            20                  25                  30

Cys Trp Tyr Gln Gln Lys Pro Gly Arg Ser Pro Val Leu Val Val His
        35                  40                  45

Gln Asp Thr Lys Arg Pro Ser Gly Ile Pro Glu Arg Phe Ser Gly Ser
    50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Thr Ile Gly Val
                85                  90                  95

Phe Gly Pro Gly Thr Arg Val Thr Val Leu
            100                 105

<210> SEQ ID NO 105
<211> LENGTH: 8
<212> TYPE: PRT
<213> ORGANISM: Artificial sequence
<220> FEATURE:
<223> OTHER INFORMATION: Synthetic peptide

<400> SEQUENCE: 105

Gly Tyr Thr Phe Thr Lys Tyr Gly

```
1               5

<210> SEQ ID NO 106
<211> LENGTH: 8
<212> TYPE: PRT
<213> ORGANISM: Artificial sequence
<220> FEATURE:
<223> OTHER INFORMATION: Synthetic peptide

<400> SEQUENCE: 106

Ile Asn Thr Asn Thr Ala Lys Pro
1               5

<210> SEQ ID NO 107
<211> LENGTH: 8
<212> TYPE: PRT
<213> ORGANISM: Artificial sequence
<220> FEATURE:
<223> OTHER INFORMATION: Synthetic peptide

<400> SEQUENCE: 107

Ala Thr Asp Gly Ser Glu Gly Ser
1               5

<210> SEQ ID NO 108
<211> LENGTH: 8
<212> TYPE: PRT
<213> ORGANISM: Artificial sequence
<220> FEATURE:
<223> OTHER INFORMATION: Synthetic peptide

<400> SEQUENCE: 108

Gly Phe Thr Phe Ser Asn His Ala
1               5

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Leu Thr Tyr Ser Gly Lys Thr Thr
1               5

<210> SEQ ID NO 110
<211> LENGTH: 13
<212> TYPE: PRT
<213> ORGANISM: Artificial sequence
<220> FEATURE:
<223> OTHER INFORMATION: Synthetic peptide

<400> SEQUENCE: 110

Ala Lys Glu Asp Tyr Asp Asp Arg Gly Phe Phe Asp Phe
1               5                   10

<210> SEQ ID NO 111
<211> LENGTH: 8
<212> TYPE: PRT
<213> ORGANISM: Artificial sequence
<220> FEATURE:
<223> OTHER INFORMATION: Synthetic peptide

<400> SEQUENCE: 111

Gly Phe Ile Phe Ser Ser Tyr Gly
1               5
```

<210> SEQ ID NO 112
<211> LENGTH: 8
<212> TYPE: PRT
<213> ORGANISM: Artificial sequence
<220> FEATURE:
<223> OTHER INFORMATION: Synthetic peptide

<400> SEQUENCE: 112

Ile Tyr Tyr Asp Glu Asn Asn Lys
1               5

<210> SEQ ID NO 113
<211> LENGTH: 17
<212> TYPE: PRT
<213> ORGANISM: Artificial sequence
<220> FEATURE:
<223> OTHER INFORMATION: Synthetic peptide

<400> SEQUENCE: 113

Ala Arg Asp Val Val Ala Ala Phe Asp Phe Ser Tyr Gly Met Asp
1               5                   10                  15

Val

<210> SEQ ID NO 114
<211> LENGTH: 8
<212> TYPE: PRT
<213> ORGANISM: Artificial sequence
<220> FEATURE:
<223> OTHER INFORMATION: Synthetic peptide

<400> SEQUENCE: 114

Gly Phe Thr Phe Ser Thr Tyr Ala
1               5

<210> SEQ ID NO 115
<211> LENGTH: 8
<212> TYPE: PRT
<213> ORGANISM: Artificial sequence
<220> FEATURE:
<223> OTHER INFORMATION: Synthetic peptide

<400> SEQUENCE: 115

Ile Ser Gly Ser Gly Ser Ser Thr
1               5

<210> SEQ ID NO 116
<211> LENGTH: 13
<212> TYPE: PRT
<213> ORGANISM: Artificial sequence
<220> FEATURE:
<223> OTHER INFORMATION: Synthetic peptide

<400> SEQUENCE: 116

Ala Arg Asp Val Leu Tyr Ser Gly Ser Tyr Phe Asp Tyr
1               5                   10

<210> SEQ ID NO 117
<211> LENGTH: 8
<212> TYPE: PRT
<213> ORGANISM: Artificial sequence
<220> FEATURE:
<223> OTHER INFORMATION: Synthetic peptide

<400> SEQUENCE: 117

Gly Phe Pro Phe Ser Asp Tyr His

```
1               5

<210> SEQ ID NO 118
<211> LENGTH: 8
<212> TYPE: PRT
<213> ORGANISM: Artificial sequence
<220> FEATURE:
<223> OTHER INFORMATION: Synthetic peptide

<400> SEQUENCE: 118

Ile Ser Ser Ala Gly Asn Lys Ile
1               5

<210> SEQ ID NO 119
<211> LENGTH: 18
<212> TYPE: PRT
<213> ORGANISM: Artificial sequence
<220> FEATURE:
<223> OTHER INFORMATION: Synthetic peptide
<220> FEATURE:
<221> NAME/KEY: misc_feature
<222> LOCATION: (15)..(15)
<223> OTHER INFORMATION: Xaa can be any naturally occurring amino acid

<400> SEQUENCE: 119

Ala Arg Asp Pro Gly Tyr Tyr His Gly Ser Gly Asn Lys Gln Xaa His
1               5                   10                  15

Gly Arg

<210> SEQ ID NO 120
<211> LENGTH: 8
<212> TYPE: PRT
<213> ORGANISM: Artificial sequence
<220> FEATURE:
<223> OTHER INFORMATION: Synthetic peptide

<400> SEQUENCE: 120

Gly Phe Ser Val Ser Asp Ser Ala
1               5

<210> SEQ ID NO 121
<211> LENGTH: 10
<212> TYPE: PRT
<213> ORGANISM: Artificial sequence
<220> FEATURE:
<223> OTHER INFORMATION: Synthetic peptide

<400> SEQUENCE: 121

Met Arg Ser Gln Ala Asn Ser Tyr Ala Thr
1               5                   10

<210> SEQ ID NO 122
<211> LENGTH: 2
<212> TYPE: PRT
<213> ORGANISM: Artificial sequence
<220> FEATURE:
<223> OTHER INFORMATION: Synthetic peptide

<400> SEQUENCE: 122

Thr Arg
1

<210> SEQ ID NO 123
<211> LENGTH: 8
<212> TYPE: PRT
<213> ORGANISM: Artificial sequence
<220> FEATURE:
```

```
<223> OTHER INFORMATION: Synthetic peptide

<400> SEQUENCE: 123

Gly Phe Thr Val Thr Thr Asn Tyr
1               5

<210> SEQ ID NO 124
<211> LENGTH: 7
<212> TYPE: PRT
<213> ORGANISM: Artificial sequence
<220> FEATURE:
<223> OTHER INFORMATION: Synthetic peptide

<400> SEQUENCE: 124

Ile Tyr Ser Ala Gly Ser Thr
1               5

<210> SEQ ID NO 125
<211> LENGTH: 12
<212> TYPE: PRT
<213> ORGANISM: Artificial sequence
<220> FEATURE:
<223> OTHER INFORMATION: Synthetic peptide

<400> SEQUENCE: 125

Ala Arg Glu Asn Pro Ala Gln Asp Ala Phe Asp Ile
1               5                   10

<210> SEQ ID NO 126
<211> LENGTH: 8
<212> TYPE: PRT
<213> ORGANISM: Artificial sequence
<220> FEATURE:
<223> OTHER INFORMATION: Synthetic peptide

<400> SEQUENCE: 126

Gly Gly Ser Ile Ser Ser Asp Tyr
1               5

<210> SEQ ID NO 127
<211> LENGTH: 7
<212> TYPE: PRT
<213> ORGANISM: Artificial sequence
<220> FEATURE:
<223> OTHER INFORMATION: Synthetic peptide

<400> SEQUENCE: 127

Ile Tyr Tyr Ser Gly Arg Thr
1               5

<210> SEQ ID NO 128
<211> LENGTH: 10
<212> TYPE: PRT
<213> ORGANISM: Artificial sequence
<220> FEATURE:
<223> OTHER INFORMATION: Synthetic peptide

<400> SEQUENCE: 128

Ala Arg Glu Arg Leu Asp Ala Phe Asp Met
1               5                   10

<210> SEQ ID NO 129
<211> LENGTH: 8
<212> TYPE: PRT
<213> ORGANISM: Artificial sequence
<220> FEATURE:
<223> OTHER INFORMATION: Synthetic peptide
```

<400> SEQUENCE: 129

Gly Phe Thr Phe Asp Asp Tyr Ala
1               5

<210> SEQ ID NO 130
<211> LENGTH: 8
<212> TYPE: PRT
<213> ORGANISM: Artificial sequence
<220> FEATURE:
<223> OTHER INFORMATION: Synthetic peptide

<400> SEQUENCE: 130

Ile Ser Trp Asn Ser Asp Ser Ile
1               5

<210> SEQ ID NO 131
<211> LENGTH: 17
<212> TYPE: PRT
<213> ORGANISM: Artificial sequence
<220> FEATURE:
<223> OTHER INFORMATION: Synthetic peptide

<400> SEQUENCE: 131

Ala Lys Val Arg Leu Asp Phe Trp Thr Gly Pro Met Gly Tyr Phe Gln
1               5                   10                  15

His

<210> SEQ ID NO 132
<211> LENGTH: 8
<212> TYPE: PRT
<213> ORGANISM: Artificial sequence
<220> FEATURE:
<223> OTHER INFORMATION: Synthetic peptide

<400> SEQUENCE: 132

Gly Phe Ser Val Ile Thr Asn Tyr
1               5

<210> SEQ ID NO 133
<211> LENGTH: 7
<212> TYPE: PRT
<213> ORGANISM: Artificial sequence
<220> FEATURE:
<223> OTHER INFORMATION: Synthetic peptide

<400> SEQUENCE: 133

Ile Tyr Ser Gly Gly Ser Thr
1               5

<210> SEQ ID NO 134
<211> LENGTH: 22
<212> TYPE: PRT
<213> ORGANISM: Artificial sequence
<220> FEATURE:
<223> OTHER INFORMATION: Synthetic peptide

<400> SEQUENCE: 134

Ala His Ala Met Asp Asp Ser Gly Ser Tyr Tyr Val Gly Leu Ser Lys
1               5                   10                  15

Asp Pro His Phe Asp Ser
            20

<210> SEQ ID NO 135
<211> LENGTH: 8

```
<212> TYPE: PRT
<213> ORGANISM: Artificial sequence
<220> FEATURE:
<223> OTHER INFORMATION: Synthetic peptide

<400> SEQUENCE: 135

Gly Phe Thr Val Arg Ser Tyr Gly
1               5

<210> SEQ ID NO 136
<211> LENGTH: 8
<212> TYPE: PRT
<213> ORGANISM: Artificial sequence
<220> FEATURE:
<223> OTHER INFORMATION: Synthetic peptide

<400> SEQUENCE: 136

Ile Leu Phe Asp Gly Thr Thr Lys
1               5

<210> SEQ ID NO 137
<211> LENGTH: 19
<212> TYPE: PRT
<213> ORGANISM: Artificial sequence
<220> FEATURE:
<223> OTHER INFORMATION: Synthetic peptide

<400> SEQUENCE: 137

Val Arg Asp Phe Asn Gln Phe Val Lys Arg Phe Val Asp Gly Pro Ala
1               5                   10                  15

Phe Asp Leu

<210> SEQ ID NO 138
<211> LENGTH: 8
<212> TYPE: PRT
<213> ORGANISM: Artificial sequence
<220> FEATURE:
<223> OTHER INFORMATION: Synthetic peptide

<400> SEQUENCE: 138

Gly Phe Thr Phe Ser Thr Tyr Val
1               5

<210> SEQ ID NO 139
<211> LENGTH: 8
<212> TYPE: PRT
<213> ORGANISM: Artificial sequence
<220> FEATURE:
<223> OTHER INFORMATION: Synthetic peptide

<400> SEQUENCE: 139

Ile Ser Tyr Asp Gly Thr Asn Lys
1               5

<210> SEQ ID NO 140
<211> LENGTH: 15
<212> TYPE: PRT
<213> ORGANISM: Artificial sequence
<220> FEATURE:
<223> OTHER INFORMATION: Synthetic peptide

<400> SEQUENCE: 140

Ala Lys Thr Met Asp Asp Ser Ser Gly Tyr Tyr Cys Pro Asp Tyr
1               5                   10                  15

<210> SEQ ID NO 141
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 141

Gly Phe Ala Phe Ser Gly Tyr Tyr
1               5

<210> SEQ ID NO 142
<211> LENGTH: 8
<212> TYPE: PRT
<213> ORGANISM: Artificial sequence
<220> FEATURE:
<223> OTHER INFORMATION: Synthetic peptide

<400> SEQUENCE: 142

Ile Asn Ser Asn Gly Leu Thr Ile
1               5

<210> SEQ ID NO 143
<211> LENGTH: 13
<212> TYPE: PRT
<213> ORGANISM: Artificial sequence
<220> FEATURE:
<223> OTHER INFORMATION: Synthetic peptide

<400> SEQUENCE: 143

Ala Arg Asp Trp Gly Thr Thr Leu Val Thr Phe Asp Leu
1               5                   10

<210> SEQ ID NO 144
<211> LENGTH: 8
<212> TYPE: PRT
<213> ORGANISM: Artificial sequence
<220> FEATURE:
<223> OTHER INFORMATION: Synthetic peptide

<400> SEQUENCE: 144

Gly Tyr Thr Phe Thr Asn Tyr Gly
1               5

<210> SEQ ID NO 145
<211> LENGTH: 8
<212> TYPE: PRT
<213> ORGANISM: Artificial sequence
<220> FEATURE:
<223> OTHER INFORMATION: Synthetic peptide

<400> SEQUENCE: 145

Ile Ser Thr Tyr Asp Gly Ala Thr
1               5

<210> SEQ ID NO 146
<211> LENGTH: 9
<212> TYPE: PRT
<213> ORGANISM: Artificial sequence
<220> FEATURE:
<223> OTHER INFORMATION: Synthetic peptide

<400> SEQUENCE: 146

Ala Arg Gly Arg Asp Ser Pro Asp His
1               5

<210> SEQ ID NO 147
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 147

Gly Tyr Thr Phe Ile Ser Tyr Gly
1               5

<210> SEQ ID NO 148
<211> LENGTH: 8
<212> TYPE: PRT
<213> ORGANISM: Artificial sequence
<220> FEATURE:
<223> OTHER INFORMATION: Synthetic peptide

<400> SEQUENCE: 148

Ile Ser Gly Tyr Asn Gly Asn Pro
1               5

<210> SEQ ID NO 149
<211> LENGTH: 13
<212> TYPE: PRT
<213> ORGANISM: Artificial sequence
<220> FEATURE:
<223> OTHER INFORMATION: Synthetic peptide

<400> SEQUENCE: 149

Ala Arg Trp Met Val Gly Asn Ile Asn Pro Phe Asp His
1               5                   10

<210> SEQ ID NO 150
<211> LENGTH: 8
<212> TYPE: PRT
<213> ORGANISM: Artificial sequence
<220> FEATURE:
<223> OTHER INFORMATION: Synthetic peptide

<400> SEQUENCE: 150

Gly Tyr Arg Phe Asn Thr Tyr Trp
1               5

<210> SEQ ID NO 151
<211> LENGTH: 8
<212> TYPE: PRT
<213> ORGANISM: Artificial sequence
<220> FEATURE:
<223> OTHER INFORMATION: Synthetic peptide

<400> SEQUENCE: 151

Ile Tyr Pro Gly Asp Leu Asp Thr
1               5

<210> SEQ ID NO 152
<211> LENGTH: 18
<212> TYPE: PRT
<213> ORGANISM: Artificial sequence
<220> FEATURE:
<223> OTHER INFORMATION: Synthetic peptide

<400> SEQUENCE: 152

Ala Arg Glu Val Tyr Val Ala Ser Thr Asp Ser Asp Tyr Tyr Gly Met
1               5                   10                  15

Asp Val

<210> SEQ ID NO 153
```

```
<211> LENGTH: 8
<212> TYPE: PRT
<213> ORGANISM: Artificial sequence
<220> FEATURE:
<223> OTHER INFORMATION: Synthetic peptide

<400> SEQUENCE: 153

Gly Phe Ser Val Ser Thr Arg Phe
1               5

<210> SEQ ID NO 154
<211> LENGTH: 7
<212> TYPE: PRT
<213> ORGANISM: Artificial sequence
<220> FEATURE:
<223> OTHER INFORMATION: Synthetic peptide

<400> SEQUENCE: 154

Val Tyr Lys Asp Gly Asp Thr
1               5

<210> SEQ ID NO 155
<211> LENGTH: 12
<212> TYPE: PRT
<213> ORGANISM: Artificial sequence
<220> FEATURE:
<223> OTHER INFORMATION: Synthetic peptide

<400> SEQUENCE: 155

Val Arg His Gly Asp Gly Trp Asn Tyr Val Asp Ser
1               5                   10

<210> SEQ ID NO 156
<211> LENGTH: 8
<212> TYPE: PRT
<213> ORGANISM: Artificial sequence
<220> FEATURE:
<223> OTHER INFORMATION: Synthetic peptide

<400> SEQUENCE: 156

Gly Phe Ser Phe Ser Asp Tyr Tyr
1               5

<210> SEQ ID NO 157
<211> LENGTH: 8
<212> TYPE: PRT
<213> ORGANISM: Artificial sequence
<220> FEATURE:
<223> OTHER INFORMATION: Synthetic peptide

<400> SEQUENCE: 157

Ile Ser Gly Ser Ser Ala Tyr Thr
1               5

<210> SEQ ID NO 158
<211> LENGTH: 20
<212> TYPE: PRT
<213> ORGANISM: Artificial sequence
<220> FEATURE:
<223> OTHER INFORMATION: Synthetic peptide

<400> SEQUENCE: 158

Ala Lys Asp Tyr Cys Gly Ser Gly Ala Cys Tyr Thr Ala Asp Pro Gly
1               5                   10                  15

Phe Phe His Gln
            20
```

<210> SEQ ID NO 159
<211> LENGTH: 8
<212> TYPE: PRT
<213> ORGANISM: Artificial sequence
<220> FEATURE:
<223> OTHER INFORMATION: Synthetic peptide

<400> SEQUENCE: 159

Gly Phe Thr Phe Ser Thr Tyr Ala
1               5

<210> SEQ ID NO 160
<211> LENGTH: 8
<212> TYPE: PRT
<213> ORGANISM: Artificial sequence
<220> FEATURE:
<223> OTHER INFORMATION: Synthetic peptide

<400> SEQUENCE: 160

Ile Ser Gly Ser Gly Ser Ser Thr
1               5

<210> SEQ ID NO 161
<211> LENGTH: 15
<212> TYPE: PRT
<213> ORGANISM: Artificial sequence
<220> FEATURE:
<223> OTHER INFORMATION: Synthetic peptide

<400> SEQUENCE: 161

Cys Ala Arg Asp Val Leu Tyr Ser Gly Ser Tyr Phe Asp Tyr Trp
1               5                   10                  15

<210> SEQ ID NO 162
<211> LENGTH: 8
<212> TYPE: PRT
<213> ORGANISM: Artificial sequence
<220> FEATURE:
<223> OTHER INFORMATION: Synthetic peptide

<400> SEQUENCE: 162

Gly Gly Ser Phe Ser Gly Phe Leu
1               5

<210> SEQ ID NO 163
<211> LENGTH: 7
<212> TYPE: PRT
<213> ORGANISM: Artificial sequence
<220> FEATURE:
<223> OTHER INFORMATION: Synthetic peptide

<400> SEQUENCE: 163

Ile Asn Asn Ser Gly Thr Thr
1               5

<210> SEQ ID NO 164
<211> LENGTH: 13
<212> TYPE: PRT
<213> ORGANISM: Artificial sequence
<220> FEATURE:
<223> OTHER INFORMATION: Synthetic peptide

<400> SEQUENCE: 164

Ala Arg Thr Pro Val Leu Arg Tyr Leu Thr Val Gly Pro
1               5                   10

```
<210> SEQ ID NO 165
<211> LENGTH: 8
<212> TYPE: PRT
<213> ORGANISM: Artificial sequence
<220> FEATURE:
<223> OTHER INFORMATION: Synthetic peptide

<400> SEQUENCE: 165

Gly Phe Thr Phe Ser Asp Phe Tyr
1               5

<210> SEQ ID NO 166
<211> LENGTH: 8
<212> TYPE: PRT
<213> ORGANISM: Artificial sequence
<220> FEATURE:
<223> OTHER INFORMATION: Synthetic peptide

<400> SEQUENCE: 166

Met Ser Ala Thr Gly Gly Asn Ile
1               5

<210> SEQ ID NO 167
<211> LENGTH: 14
<212> TYPE: PRT
<213> ORGANISM: Artificial sequence
<220> FEATURE:
<223> OTHER INFORMATION: Synthetic peptide

<400> SEQUENCE: 167

Ala Arg Arg Lys Phe Gly Ala Gly Ser Ala Ile Phe Asp His
1               5                   10

<210> SEQ ID NO 168
<211> LENGTH: 10
<212> TYPE: PRT
<213> ORGANISM: Artificial sequence
<220> FEATURE:
<223> OTHER INFORMATION: Synthetic peptide

<400> SEQUENCE: 168

Asp Ala Ser Ile Asp Thr Pro Ser Tyr Phe
1               5                   10

<210> SEQ ID NO 169
<211> LENGTH: 7
<212> TYPE: PRT
<213> ORGANISM: Artificial sequence
<220> FEATURE:
<223> OTHER INFORMATION: Synthetic peptide

<400> SEQUENCE: 169

Ile Tyr Tyr Thr Gly Asn Lys
1               5

<210> SEQ ID NO 170
<211> LENGTH: 14
<212> TYPE: PRT
<213> ORGANISM: Artificial sequence
<220> FEATURE:
<223> OTHER INFORMATION: Synthetic peptide

<400> SEQUENCE: 170

Ala Arg Tyr Val Asp Tyr Val Trp Leu Arg Ala Phe Asp Ile
1               5                   10

<210> SEQ ID NO 171
```

```
<211> LENGTH: 10
<212> TYPE: PRT
<213> ORGANISM: Artificial sequence
<220> FEATURE:
<223> OTHER INFORMATION: Synthetic peptide

<400> SEQUENCE: 171

Asp Asp Ser Ile Ser Thr Pro Ser Tyr Phe
1               5                   10

<210> SEQ ID NO 172
<211> LENGTH: 7
<212> TYPE: PRT
<213> ORGANISM: Artificial sequence
<220> FEATURE:
<223> OTHER INFORMATION: Synthetic peptide

<400> SEQUENCE: 172

Ile Tyr Tyr Thr Gly Thr Thr
1               5

<210> SEQ ID NO 173
<211> LENGTH: 14
<212> TYPE: PRT
<213> ORGANISM: Artificial sequence
<220> FEATURE:
<223> OTHER INFORMATION: Synthetic peptide

<400> SEQUENCE: 173

Ala Arg Tyr Leu Asp Tyr Val Trp Leu Arg Ala Phe Asp Val
1               5                   10

<210> SEQ ID NO 174
<211> LENGTH: 10
<212> TYPE: PRT
<213> ORGANISM: Artificial sequence
<220> FEATURE:
<223> OTHER INFORMATION: Synthetic peptide

<400> SEQUENCE: 174

Gly Gly Ser Ile Ser Ser Gly Gly Phe Phe
1               5                   10

<210> SEQ ID NO 175
<211> LENGTH: 7
<212> TYPE: PRT
<213> ORGANISM: Artificial sequence
<220> FEATURE:
<223> OTHER INFORMATION: Synthetic peptide

<400> SEQUENCE: 175

Ile Phe Tyr Thr Gly Ser Thr
1               5

<210> SEQ ID NO 176
<211> LENGTH: 15
<212> TYPE: PRT
<213> ORGANISM: Artificial sequence
<220> FEATURE:
<223> OTHER INFORMATION: Synthetic peptide

<400> SEQUENCE: 176

Ala Arg Gln Gly Gly Val Arg Gly Asn Tyr Tyr Phe Met Asp Val
1               5                   10                  15

<210> SEQ ID NO 177
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 177

Gly Gly Ser Ile Ser Asn Asn Tyr
1               5

<210> SEQ ID NO 178
<211> LENGTH: 7
<212> TYPE: PRT
<213> ORGANISM: Artificial sequence
<220> FEATURE:
<223> OTHER INFORMATION: Synthetic peptide

<400> SEQUENCE: 178

Ile Ser Tyr Ser Gly Arg Thr
1               5

<210> SEQ ID NO 179
<211> LENGTH: 16
<212> TYPE: PRT
<213> ORGANISM: Artificial sequence
<220> FEATURE:
<223> OTHER INFORMATION: Synthetic peptide

<400> SEQUENCE: 179

Ala Arg Glu Ser Thr Tyr Ser Tyr Lys Leu Gly Asp Ala Phe Asp Ile
1               5                   10                  15

<210> SEQ ID NO 180
<211> LENGTH: 8
<212> TYPE: PRT
<213> ORGANISM: Artificial sequence
<220> FEATURE:
<223> OTHER INFORMATION: Synthetic peptide

<400> SEQUENCE: 180

Gly Tyr Pro Phe Ala Thr Tyr Trp
1               5

<210> SEQ ID NO 181
<211> LENGTH: 8
<212> TYPE: PRT
<213> ORGANISM: Artificial sequence
<220> FEATURE:
<223> OTHER INFORMATION: Synthetic peptide

<400> SEQUENCE: 181

Ile Tyr Pro Glu Asp Ser Asp Thr
1               5

<210> SEQ ID NO 182
<211> LENGTH: 20
<212> TYPE: PRT
<213> ORGANISM: Artificial sequence
<220> FEATURE:
<223> OTHER INFORMATION: Synthetic peptide

<400> SEQUENCE: 182

Ala Arg Val Ser Arg Tyr Tyr Asp Ser Arg Ser Tyr Tyr Pro Asp
1               5                   10                  15

Ala Phe Asp Ile
            20
```

```
<210> SEQ ID NO 183
<211> LENGTH: 6
<212> TYPE: PRT
<213> ORGANISM: Artificial sequence
<220> FEATURE:
<223> OTHER INFORMATION: Synthetic peptide

<400> SEQUENCE: 183

Gln Ser Ile Gly Thr Trp
1               5

<210> SEQ ID NO 184
<211> LENGTH: 3
<212> TYPE: PRT
<213> ORGANISM: Artificial sequence
<220> FEATURE:
<223> OTHER INFORMATION: Synthetic peptide

<400> SEQUENCE: 184

Lys Ala Ser
1

<210> SEQ ID NO 185
<211> LENGTH: 9
<212> TYPE: PRT
<213> ORGANISM: Artificial sequence
<220> FEATURE:
<223> OTHER INFORMATION: Synthetic peptide

<400> SEQUENCE: 185

Gln Gln Tyr Asn Thr Tyr Leu Gly Thr
1               5

<210> SEQ ID NO 186
<211> LENGTH: 6
<212> TYPE: PRT
<213> ORGANISM: Artificial sequence
<220> FEATURE:
<223> OTHER INFORMATION: Synthetic peptide

<400> SEQUENCE: 186

Gln Thr Ile Ser Thr Tyr
1               5

<210> SEQ ID NO 187
<211> LENGTH: 3
<212> TYPE: PRT
<213> ORGANISM: Artificial sequence
<220> FEATURE:
<223> OTHER INFORMATION: Synthetic peptide

<400> SEQUENCE: 187

Ala Ala Ser
1

<210> SEQ ID NO 188
<211> LENGTH: 9
<212> TYPE: PRT
<213> ORGANISM: Artificial sequence
<220> FEATURE:
<223> OTHER INFORMATION: Synthetic peptide

<400> SEQUENCE: 188

Gln Gln Gly Tyr Asn Asn Pro Tyr Thr
1               5

<210> SEQ ID NO 189
```

```
<211> LENGTH: 6
<212> TYPE: PRT
<213> ORGANISM: Artificial sequence
<220> FEATURE:
<223> OTHER INFORMATION: Synthetic peptide

<400> SEQUENCE: 189

Asn Lys Leu Glu Lys Phe
1               5

<210> SEQ ID NO 190
<211> LENGTH: 3
<212> TYPE: PRT
<213> ORGANISM: Artificial sequence
<220> FEATURE:
<223> OTHER INFORMATION: Synthetic peptide

<400> SEQUENCE: 190

Gln Asp Asn
1

<210> SEQ ID NO 191
<211> LENGTH: 6
<212> TYPE: PRT
<213> ORGANISM: Artificial sequence
<220> FEATURE:
<223> OTHER INFORMATION: Synthetic peptide

<400> SEQUENCE: 191

Gln Ala Trp Asp Gly Ser
1               5

<210> SEQ ID NO 192
<211> LENGTH: 6
<212> TYPE: PRT
<213> ORGANISM: Artificial sequence
<220> FEATURE:
<223> OTHER INFORMATION: Synthetic peptide

<400> SEQUENCE: 192

Gln Gly Ile Arg Asn Asn
1               5

<210> SEQ ID NO 193
<211> LENGTH: 3
<212> TYPE: PRT
<213> ORGANISM: Artificial sequence
<220> FEATURE:
<223> OTHER INFORMATION: Synthetic peptide

<400> SEQUENCE: 193

Ala Ala Ser
1

<210> SEQ ID NO 194
<211> LENGTH: 9
<212> TYPE: PRT
<213> ORGANISM: Artificial sequence
<220> FEATURE:
<223> OTHER INFORMATION: Synthetic peptide

<400> SEQUENCE: 194

Leu Gln Asp Tyr Asn Tyr Pro Arg Thr
1               5

<210> SEQ ID NO 195
<211> LENGTH: 8
```

```
<212> TYPE: PRT
<213> ORGANISM: Artificial sequence
<220> FEATURE:
<223> OTHER INFORMATION: Synthetic peptide

<400> SEQUENCE: 195

Ser Ser Asn Ile Gly Tyr Asn Tyr
1               5

<210> SEQ ID NO 196
<211> LENGTH: 3
<212> TYPE: PRT
<213> ORGANISM: Artificial sequence
<220> FEATURE:
<223> OTHER INFORMATION: Synthetic peptide

<400> SEQUENCE: 196

Asp Asp Asp
1

<210> SEQ ID NO 197
<211> LENGTH: 2
<212> TYPE: PRT
<213> ORGANISM: Artificial sequence
<220> FEATURE:
<223> OTHER INFORMATION: Synthetic peptide

<400> SEQUENCE: 197

Ser Thr
1

<210> SEQ ID NO 198
<211> LENGTH: 6
<212> TYPE: PRT
<213> ORGANISM: Artificial sequence
<220> FEATURE:
<223> OTHER INFORMATION: Synthetic peptide

<400> SEQUENCE: 198

Ser Ile Gly Ser Arg Ser
1               5

<210> SEQ ID NO 199
<211> LENGTH: 3
<212> TYPE: PRT
<213> ORGANISM: Artificial sequence
<220> FEATURE:
<223> OTHER INFORMATION: Synthetic peptide

<400> SEQUENCE: 199

Tyr Asp Arg
1

<210> SEQ ID NO 200
<211> LENGTH: 11
<212> TYPE: PRT
<213> ORGANISM: Artificial sequence
<220> FEATURE:
<223> OTHER INFORMATION: Synthetic peptide

<400> SEQUENCE: 200

Gln Val Trp Asp Gly Ser Ser Asp Gln Tyr Val
1               5                   10

<210> SEQ ID NO 201
<211> LENGTH: 6
<212> TYPE: PRT
```

```
<213> ORGANISM: Artificial sequence
<220> FEATURE:
<223> OTHER INFORMATION: Synthetic peptide

<400> SEQUENCE: 201

Asn Ile Gly Ser Lys Asn
1               5

<210> SEQ ID NO 202
<211> LENGTH: 3
<212> TYPE: PRT
<213> ORGANISM: Artificial sequence
<220> FEATURE:
<223> OTHER INFORMATION: Synthetic peptide

<400> SEQUENCE: 202

Arg Asp Ser
1

<210> SEQ ID NO 203
<211> LENGTH: 9
<212> TYPE: PRT
<213> ORGANISM: Artificial sequence
<220> FEATURE:
<223> OTHER INFORMATION: Synthetic peptide

<400> SEQUENCE: 203

His Val Trp Asp Thr Ser Thr Val Val
1               5

<210> SEQ ID NO 204
<211> LENGTH: 8
<212> TYPE: PRT
<213> ORGANISM: Artificial sequence
<220> FEATURE:
<223> OTHER INFORMATION: Synthetic peptide

<400> SEQUENCE: 204

Ser Ser Asn Ile Gly Ser Asn Tyr
1               5

<210> SEQ ID NO 205
<211> LENGTH: 3
<212> TYPE: PRT
<213> ORGANISM: Artificial sequence
<220> FEATURE:
<223> OTHER INFORMATION: Synthetic peptide

<400> SEQUENCE: 205

Arg Asn Asn
1

<210> SEQ ID NO 206
<211> LENGTH: 11
<212> TYPE: PRT
<213> ORGANISM: Artificial sequence
<220> FEATURE:
<223> OTHER INFORMATION: Synthetic peptide

<400> SEQUENCE: 206

Ala Ala Trp Asp Asp Arg Leu Ser Ser Trp Val
1               5                   10

<210> SEQ ID NO 207
<211> LENGTH: 7
<212> TYPE: PRT
<213> ORGANISM: Artificial sequence
```

```
<220> FEATURE:
<223> OTHER INFORMATION: Synthetic peptide

<400> SEQUENCE: 207

Gln Thr Ile Thr Ser Asn Tyr
1               5

<210> SEQ ID NO 208
<211> LENGTH: 3
<212> TYPE: PRT
<213> ORGANISM: Artificial sequence
<220> FEATURE:
<223> OTHER INFORMATION: Synthetic peptide

<400> SEQUENCE: 208

Gly Ala Ser
1

<210> SEQ ID NO 209
<211> LENGTH: 11
<212> TYPE: PRT
<213> ORGANISM: Artificial sequence
<220> FEATURE:
<223> OTHER INFORMATION: Synthetic peptide

<400> SEQUENCE: 209

Gln Gln Tyr Gly Ser Tyr Arg Gly Val Phe Thr
1               5                   10

<210> SEQ ID NO 210
<211> LENGTH: 9
<212> TYPE: PRT
<213> ORGANISM: Artificial sequence
<220> FEATURE:
<223> OTHER INFORMATION: Synthetic peptide

<400> SEQUENCE: 210

Ser Ser Asp Val Gly Ser Tyr Asn Leu
1               5

<210> SEQ ID NO 211
<211> LENGTH: 3
<212> TYPE: PRT
<213> ORGANISM: Artificial sequence
<220> FEATURE:
<223> OTHER INFORMATION: Synthetic peptide

<400> SEQUENCE: 211

Glu Val Thr
1

<210> SEQ ID NO 212
<211> LENGTH: 11
<212> TYPE: PRT
<213> ORGANISM: Artificial sequence
<220> FEATURE:
<223> OTHER INFORMATION: Synthetic peptide

<400> SEQUENCE: 212

Cys Ser Tyr Ala Gly Ser Ser Ile Ser Phe Val
1               5                   10

<210> SEQ ID NO 213
<211> LENGTH: 6
<212> TYPE: PRT
<213> ORGANISM: Artificial sequence
<220> FEATURE:
```

```
<223> OTHER INFORMATION: Synthetic peptide

<400> SEQUENCE: 213

Ser Leu Arg Asn Tyr Phe
1               5

<210> SEQ ID NO 214
<211> LENGTH: 3
<212> TYPE: PRT
<213> ORGANISM: Artificial sequence
<220> FEATURE:
<223> OTHER INFORMATION: Synthetic peptide

<400> SEQUENCE: 214

Gly Gln Asn
1

<210> SEQ ID NO 215
<211> LENGTH: 12
<212> TYPE: PRT
<213> ORGANISM: Artificial sequence
<220> FEATURE:
<223> OTHER INFORMATION: Synthetic peptide

<400> SEQUENCE: 215

Asn Ser Arg Asp Ser Ser Gly Asn His Leu Tyr Val
1               5                   10

<210> SEQ ID NO 216
<211> LENGTH: 7
<212> TYPE: PRT
<213> ORGANISM: Artificial sequence
<220> FEATURE:
<223> OTHER INFORMATION: Synthetic peptide

<400> SEQUENCE: 216

Ser Gly His Arg Gly Tyr Asn
1               5

<210> SEQ ID NO 217
<211> LENGTH: 7
<212> TYPE: PRT
<213> ORGANISM: Artificial sequence
<220> FEATURE:
<223> OTHER INFORMATION: Synthetic peptide

<400> SEQUENCE: 217

Leu Glu Gly Ser Asp Ser Tyr
1               5

<210> SEQ ID NO 218
<211> LENGTH: 4
<212> TYPE: PRT
<213> ORGANISM: Artificial sequence
<220> FEATURE:
<223> OTHER INFORMATION: Synthetic peptide

<400> SEQUENCE: 218

Asp Ser Arg Val
1

<210> SEQ ID NO 219
<211> LENGTH: 6
<212> TYPE: PRT
<213> ORGANISM: Artificial sequence
<220> FEATURE:
<223> OTHER INFORMATION: Synthetic peptide
```

-continued

```
<400> SEQUENCE: 219

Gln Ser Ile Asn Arg Trp
1               5

<210> SEQ ID NO 220
<211> LENGTH: 3
<212> TYPE: PRT
<213> ORGANISM: Artificial sequence
<220> FEATURE:
<223> OTHER INFORMATION: Synthetic peptide

<400> SEQUENCE: 220

Lys Ala Ser
1

<210> SEQ ID NO 221
<211> LENGTH: 9
<212> TYPE: PRT
<213> ORGANISM: Artificial sequence
<220> FEATURE:
<223> OTHER INFORMATION: Synthetic peptide

<400> SEQUENCE: 221

Gln Gln Tyr Asp His Phe Pro His Thr
1               5

<210> SEQ ID NO 222
<211> LENGTH: 4
<212> TYPE: PRT
<213> ORGANISM: Artificial sequence
<220> FEATURE:
<223> OTHER INFORMATION: Synthetic peptide

<400> SEQUENCE: 222

Arg Asn Ser Phe
1

<210> SEQ ID NO 223
<211> LENGTH: 3
<212> TYPE: PRT
<213> ORGANISM: Artificial sequence
<220> FEATURE:
<223> OTHER INFORMATION: Synthetic peptide

<400> SEQUENCE: 223

Gly Gln Asn
1

<210> SEQ ID NO 224
<211> LENGTH: 12
<212> TYPE: PRT
<213> ORGANISM: Artificial sequence
<220> FEATURE:
<223> OTHER INFORMATION: Synthetic peptide

<400> SEQUENCE: 224

Asn Ser Arg Asp Ser Ser Gly Asn His Phe Tyr Val
1               5                   10

<210> SEQ ID NO 225
<211> LENGTH: 9
<212> TYPE: PRT
<213> ORGANISM: Artificial sequence
<220> FEATURE:
<223> OTHER INFORMATION: Synthetic peptide
```

```
<400> SEQUENCE: 225

Ser Asn Asp Val Gly Arg Ser Asp Leu
1               5

<210> SEQ ID NO 226
<211> LENGTH: 3
<212> TYPE: PRT
<213> ORGANISM: Artificial sequence
<220> FEATURE:
<223> OTHER INFORMATION: Synthetic peptide

<400> SEQUENCE: 226

Glu Ser Ser
1

<210> SEQ ID NO 227
<211> LENGTH: 10
<212> TYPE: PRT
<213> ORGANISM: Artificial sequence
<220> FEATURE:
<223> OTHER INFORMATION: Synthetic peptide

<400> SEQUENCE: 227

Cys Ser Tyr Ala Gly Gly Asn Thr Tyr Val
1               5                   10

<210> SEQ ID NO 228
<211> LENGTH: 6
<212> TYPE: PRT
<213> ORGANISM: Artificial sequence
<220> FEATURE:
<223> OTHER INFORMATION: Synthetic peptide

<400> SEQUENCE: 228

His Ser Leu Ser Ser His
1               5

<210> SEQ ID NO 229
<211> LENGTH: 3
<212> TYPE: PRT
<213> ORGANISM: Artificial sequence
<220> FEATURE:
<223> OTHER INFORMATION: Synthetic peptide

<400> SEQUENCE: 229

Asp Ala Ser
1

<210> SEQ ID NO 230
<211> LENGTH: 9
<212> TYPE: PRT
<213> ORGANISM: Artificial sequence
<220> FEATURE:
<223> OTHER INFORMATION: Synthetic peptide

<400> SEQUENCE: 230

Gln Gln Tyr Asn Asn Trp Pro Leu Thr
1               5

<210> SEQ ID NO 231
<211> LENGTH: 6
<212> TYPE: PRT
<213> ORGANISM: Artificial sequence
<220> FEATURE:
<223> OTHER INFORMATION: Synthetic peptide

<400> SEQUENCE: 231
```

```
Asn Ile Gly Ser Lys Ser
1               5
```

<210> SEQ ID NO 232
<211> LENGTH: 3
<212> TYPE: PRT
<213> ORGANISM: Artificial sequence
<220> FEATURE:
<223> OTHER INFORMATION: Synthetic peptide

<400> SEQUENCE: 232

```
Tyr Asp Ser
1
```

<210> SEQ ID NO 233
<211> LENGTH: 13
<212> TYPE: PRT
<213> ORGANISM: Artificial sequence
<220> FEATURE:
<223> OTHER INFORMATION: Synthetic peptide

<400> SEQUENCE: 233

```
Gln Val Trp Asp Asn Thr Asn Asp His Pro Ser Tyr Val
1               5                   10
```

<210> SEQ ID NO 234
<211> LENGTH: 6
<212> TYPE: PRT
<213> ORGANISM: Artificial sequence
<220> FEATURE:
<223> OTHER INFORMATION: Synthetic peptide

<400> SEQUENCE: 234

```
Gln Asp Val Gly Lys Tyr
1               5
```

<210> SEQ ID NO 235
<211> LENGTH: 3
<212> TYPE: PRT
<213> ORGANISM: Artificial sequence
<220> FEATURE:
<223> OTHER INFORMATION: Synthetic peptide

<400> SEQUENCE: 235

```
Ala Ala Ser
1
```

<210> SEQ ID NO 236
<211> LENGTH: 10
<212> TYPE: PRT
<213> ORGANISM: Artificial sequence
<220> FEATURE:
<223> OTHER INFORMATION: Synthetic peptide

<400> SEQUENCE: 236

```
Gln Gln Ser Ser Ser Thr Ala Ala Trp Thr
1               5                   10
```

<210> SEQ ID NO 237
<211> LENGTH: 6
<212> TYPE: PRT
<213> ORGANISM: Artificial sequence
<220> FEATURE:
<223> OTHER INFORMATION: Synthetic peptide

<400> SEQUENCE: 237

```
Lys Leu Gly Asp Lys Ser
1               5

<210> SEQ ID NO 238
<211> LENGTH: 3
<212> TYPE: PRT
<213> ORGANISM: Artificial sequence
<220> FEATURE:
<223> OTHER INFORMATION: Synthetic peptide

<400> SEQUENCE: 238

Gln Asp Tyr
1

<210> SEQ ID NO 239
<211> LENGTH: 9
<212> TYPE: PRT
<213> ORGANISM: Artificial sequence
<220> FEATURE:
<223> OTHER INFORMATION: Synthetic peptide

<400> SEQUENCE: 239

Gln Ala Trp Asp Arg Lys Ile Gly Gln
1               5

<210> SEQ ID NO 240
<211> LENGTH: 6
<212> TYPE: PRT
<213> ORGANISM: Artificial sequence
<220> FEATURE:
<223> OTHER INFORMATION: Synthetic peptide

<400> SEQUENCE: 240

Lys Leu Gly Glu Arg Tyr
1               5

<210> SEQ ID NO 241
<211> LENGTH: 3
<212> TYPE: PRT
<213> ORGANISM: Artificial sequence
<220> FEATURE:
<223> OTHER INFORMATION: Synthetic peptide

<400> SEQUENCE: 241

Gln Thr Asn
1

<210> SEQ ID NO 242
<211> LENGTH: 9
<212> TYPE: PRT
<213> ORGANISM: Artificial sequence
<220> FEATURE:
<223> OTHER INFORMATION: Synthetic peptide

<400> SEQUENCE: 242

Leu Thr Trp Asp Arg Gly Thr Pro Val
1               5

<210> SEQ ID NO 243
<211> LENGTH: 6
<212> TYPE: PRT
<213> ORGANISM: Artificial sequence
<220> FEATURE:
<223> OTHER INFORMATION: Synthetic peptide

<400> SEQUENCE: 243

Pro Ser Ala Gly Arg Phe
```

```
<210> SEQ ID NO 244
<211> LENGTH: 3
<212> TYPE: PRT
<213> ORGANISM: Artificial sequence
<220> FEATURE:
<223> OTHER INFORMATION: Synthetic peptide

<400> SEQUENCE: 244

Asp Ala Ser
1

<210> SEQ ID NO 245
<211> LENGTH: 9
<212> TYPE: PRT
<213> ORGANISM: Artificial sequence
<220> FEATURE:
<223> OTHER INFORMATION: Synthetic peptide

<400> SEQUENCE: 245

Gln His Arg Ser Asn Trp Pro Leu Thr
1               5

<210> SEQ ID NO 246
<211> LENGTH: 6
<212> TYPE: PRT
<213> ORGANISM: Artificial sequence
<220> FEATURE:
<223> OTHER INFORMATION: Synthetic peptide

<400> SEQUENCE: 246

Pro Ser Val Gly Arg Phe
1               5

<210> SEQ ID NO 247
<211> LENGTH: 3
<212> TYPE: PRT
<213> ORGANISM: Artificial sequence
<220> FEATURE:
<223> OTHER INFORMATION: Synthetic peptide

<400> SEQUENCE: 247

Asp Ala Ser
1

<210> SEQ ID NO 248
<211> LENGTH: 9
<212> TYPE: PRT
<213> ORGANISM: Artificial sequence
<220> FEATURE:
<223> OTHER INFORMATION: Synthetic peptide

<400> SEQUENCE: 248

Gln His Arg Ser Asn Trp Pro Val Thr
1               5

<210> SEQ ID NO 249
<211> LENGTH: 6
<212> TYPE: PRT
<213> ORGANISM: Artificial sequence
<220> FEATURE:
<223> OTHER INFORMATION: Synthetic peptide

<400> SEQUENCE: 249

Gln Ser Ile Ser Asn Tyr
1               5
```

```
<210> SEQ ID NO 250
<211> LENGTH: 3
<212> TYPE: PRT
<213> ORGANISM: Artificial sequence
<220> FEATURE:
<223> OTHER INFORMATION: Synthetic peptide

<400> SEQUENCE: 250

Ala Ala Ser
1

<210> SEQ ID NO 251
<211> LENGTH: 9
<212> TYPE: PRT
<213> ORGANISM: Artificial sequence
<220> FEATURE:
<223> OTHER INFORMATION: Synthetic peptide

<400> SEQUENCE: 251

Gln Gln Ser Tyr Asn Thr Pro Tyr Ser
1               5

<210> SEQ ID NO 252
<211> LENGTH: 8
<212> TYPE: PRT
<213> ORGANISM: Artificial sequence
<220> FEATURE:
<223> OTHER INFORMATION: Synthetic peptide

<400> SEQUENCE: 252

Ser Ser Asn Ile Gly Arg Asn Thr
1               5

<210> SEQ ID NO 253
<211> LENGTH: 3
<212> TYPE: PRT
<213> ORGANISM: Artificial sequence
<220> FEATURE:
<223> OTHER INFORMATION: Synthetic peptide

<400> SEQUENCE: 253

Ser Asn Asp
1

<210> SEQ ID NO 254
<211> LENGTH: 11
<212> TYPE: PRT
<213> ORGANISM: Artificial sequence
<220> FEATURE:
<223> OTHER INFORMATION: Synthetic peptide

<400> SEQUENCE: 254

Ala Ala Trp Asp Asp Arg Leu Asn Gly Trp Val
1               5                   10

<210> SEQ ID NO 255
<211> LENGTH: 6
<212> TYPE: PRT
<213> ORGANISM: Artificial sequence
<220> FEATURE:
<223> OTHER INFORMATION: Synthetic peptide

<400> SEQUENCE: 255

Lys Leu Gly Asp Lys Tyr
1               5
```

```
<210> SEQ ID NO 256
<211> LENGTH: 3
<212> TYPE: PRT
<213> ORGANISM: Artificial sequence
<220> FEATURE:
<223> OTHER INFORMATION: Synthetic peptide

<400> SEQUENCE: 256

Gln Asp Thr
1

<210> SEQ ID NO 257
<211> LENGTH: 9
<212> TYPE: PRT
<213> ORGANISM: Artificial sequence
<220> FEATURE:
<223> OTHER INFORMATION: Synthetic peptide

<400> SEQUENCE: 257

Gln Ala Trp Asp Ser Thr Ile Gly Val
1               5

<210> SEQ ID NO 258
<211> LENGTH: 17
<212> TYPE: PRT
<213> ORGANISM: Artificial sequence
<220> FEATURE:
<223> OTHER INFORMATION: Synthetic peptide

<400> SEQUENCE: 258

Cys Ala Lys Thr Met Asp Asp Ser Ser Gly Tyr Tyr Cys Pro Asp Tyr
1               5                   10                  15

Trp

<210> SEQ ID NO 259
<211> LENGTH: 15
<212> TYPE: PRT
<213> ORGANISM: Artificial sequence
<220> FEATURE:
<223> OTHER INFORMATION: Synthetic peptide

<400> SEQUENCE: 259

Cys Ala Arg Trp Met Val Gly Asn Ile Asn Pro Gly Asp His Trp
1               5                   10                  15

<210> SEQ ID NO 260
<211> LENGTH: 15
<212> TYPE: PRT
<213> ORGANISM: Artificial sequence
<220> FEATURE:
<223> OTHER INFORMATION: Synthetic peptide

<400> SEQUENCE: 260

Cys Ala Arg Asp Trp Gly Thr Thr Leu Val Thr Phe Asp Leu Trp
1               5                   10                  15

<210> SEQ ID NO 261
<211> LENGTH: 15
<212> TYPE: PRT
<213> ORGANISM: Artificial sequence
<220> FEATURE:
<223> OTHER INFORMATION: Synthetic peptide

<400> SEQUENCE: 261

Cys Val Arg His Gly Asp Gly Trp Asn Tyr Val Asp Ser Leu Trp
1               5                   10                  15
```

<210> SEQ ID NO 262
<211> LENGTH: 11
<212> TYPE: PRT
<213> ORGANISM: Artificial sequence
<220> FEATURE:
<223> OTHER INFORMATION: Synthetic peptide

<400> SEQUENCE: 262

Cys Ala Arg Gly Arg Asp Ser Pro Asp His Trp
1               5                   10

<210> SEQ ID NO 263
<211> LENGTH: 20
<212> TYPE: PRT
<213> ORGANISM: Artificial sequence
<220> FEATURE:
<223> OTHER INFORMATION: Synthetic peptide

<400> SEQUENCE: 263

Cys Ala Arg Glu Val Tyr Val Ala Ser Thr Asp Ser Asp Tyr Tyr Gly
1               5                   10                  15

Met Asp Val Trp
            20

<210> SEQ ID NO 264
<211> LENGTH: 15
<212> TYPE: PRT
<213> ORGANISM: Artificial sequence
<220> FEATURE:
<223> OTHER INFORMATION: Synthetic peptide

<400> SEQUENCE: 264

Cys Ala Arg Asp Val Leu Tyr Ser Gly Ser Tyr Phe Asp Tyr Trp
1               5                   10                  15

<210> SEQ ID NO 265
<211> LENGTH: 22
<212> TYPE: PRT
<213> ORGANISM: Artificial sequence
<220> FEATURE:
<223> OTHER INFORMATION: Synthetic peptide

<400> SEQUENCE: 265

Cys Ala Lys Asp Tyr Cys Gly Ser Gly Ala Cys Tyr Thr Ala Asp Pro
1               5                   10                  15

Gly Phe Phe His Gln Trp
            20

<210> SEQ ID NO 266
<211> LENGTH: 15
<212> TYPE: PRT
<213> ORGANISM: Artificial sequence
<220> FEATURE:
<223> OTHER INFORMATION: Synthetic peptide

<400> SEQUENCE: 266

Cys Ala Arg Thr Pro Val Leu Arg Tyr Leu Thr Val Gly Pro Trp
1               5                   10                  15

<210> SEQ ID NO 267
<211> LENGTH: 15
<212> TYPE: PRT
<213> ORGANISM: Artificial sequence
<220> FEATURE:
<223> OTHER INFORMATION: Synthetic peptide

```
<400> SEQUENCE: 267

Cys Ala Lys Glu Asp Tyr Asp Asp Arg Gly Phe Phe Asp Phe Trp
1               5                   10                  15

<210> SEQ ID NO 268
<211> LENGTH: 10
<212> TYPE: PRT
<213> ORGANISM: Artificial sequence
<220> FEATURE:
<223> OTHER INFORMATION: Synthetic peptide

<400> SEQUENCE: 268

Cys Ala Thr Asp Gly Ser Glu Gly Ser Trp
1               5                   10

<210> SEQ ID NO 269
<211> LENGTH: 19
<212> TYPE: PRT
<213> ORGANISM: Artificial sequence
<220> FEATURE:
<223> OTHER INFORMATION: Synthetic peptide

<400> SEQUENCE: 269

Cys Ala Arg Asp Val Val Val Ala Ala Phe Asp Phe Ser Tyr Gly Met
1               5                   10                  15

Asp Val Trp

<210> SEQ ID NO 270
<211> LENGTH: 15
<212> TYPE: PRT
<213> ORGANISM: Artificial sequence
<220> FEATURE:
<223> OTHER INFORMATION: Synthetic peptide

<400> SEQUENCE: 270

Cys Ala Arg Asp Val Leu Tyr Ser Gly Ser Tyr Phe Asp Tyr Trp
1               5                   10                  15

<210> SEQ ID NO 271
<211> LENGTH: 14
<212> TYPE: PRT
<213> ORGANISM: Artificial sequence
<220> FEATURE:
<223> OTHER INFORMATION: Synthetic peptide

<400> SEQUENCE: 271

Cys Ala Arg Glu Asn Pro Ala Gln Asp Ala Phe Asp Ile Trp
1               5                   10

<210> SEQ ID NO 272
<211> LENGTH: 19
<212> TYPE: PRT
<213> ORGANISM: Artificial sequence
<220> FEATURE:
<223> OTHER INFORMATION: Synthetic peptide

<400> SEQUENCE: 272

Cys Ala Lys Val Arg Leu Asp Phe Trp Thr Gly Pro Met Gly Tyr Phe
1               5                   10                  15

Gln His Trp

<210> SEQ ID NO 273
<211> LENGTH: 17
<212> TYPE: PRT
```

```
<213> ORGANISM: Artificial sequence
<220> FEATURE:
<223> OTHER INFORMATION: Synthetic peptide

<400> SEQUENCE: 273

Cys Ala Arg Val Asp Ile Thr Ala Thr Gly Thr Gly Gly Phe Asp Ile
1               5                   10                  15

Trp

<210> SEQ ID NO 274
<211> LENGTH: 21
<212> TYPE: PRT
<213> ORGANISM: Artificial sequence
<220> FEATURE:
<223> OTHER INFORMATION: Synthetic peptide

<400> SEQUENCE: 274

Cys Val Arg Asp Phe Asn Gln Phe Val Lys Arg Phe Val Asp Gly Pro
1               5                   10                  15

Ala Phe Asp Leu Trp
            20

<210> SEQ ID NO 275
<211> LENGTH: 21
<212> TYPE: DNA
<213> ORGANISM: Artificial sequence
<220> FEATURE:
<223> OTHER INFORMATION: Synthetic oligonucleotide
<220> FEATURE:
<221> NAME/KEY: modified_base
<222> LOCATION: (1)..(20)
<223> OTHER INFORMATION: phosphorothioate-modified oligodeoxynucleotide

<400> SEQUENCE: 275
tcgtcgtttt tcggtcgttt t                                         21
```